(12) United States Patent
Sha et al.

(10) Patent No.: US 7,303,890 B2
(45) Date of Patent: *Dec. 4, 2007

(54) PROTEINS, GENES ENCODING THEM AND METHOD OF USING THE SAME

(75) Inventors: Shiken Sha, Kanagawa (JP); Hidehito Mukai, Kanagawa (JP); Yoshiko Aoki, Kanagawa (JP); Yoshisuke Nishi, Kanagawa (JP)

(73) Assignee: Japan Tobacco Inc., Tokyo (JP)

( * ) Notice: Subject to any disclaimer, the term of this patent is extended or adjusted under 35 U.S.C. 154(b) by 398 days.

This patent is subject to a terminal disclaimer.

(21) Appl. No.: 10/381,710

(22) PCT Filed: Sep. 27, 2001

(86) PCT No.: PCT/JP01/08446

§ 371 (c)(1),
(2), (4) Date: Jul. 17, 2003

(87) PCT Pub. No.: WO02/26978

PCT Pub. Date: Apr. 4, 2002

(65) Prior Publication Data

US 2004/0052789 A1   Mar. 18, 2004

(30) Foreign Application Priority Data

Sep. 27, 2000 (JP) ............................. 2000-294191

(51) Int. Cl.
*G01N 33/567* (2006.01)
(52) U.S. Cl. .................. 435/7.21; 435/7.2; 435/7.1; 435/69.1; 435/320.1; 435/325; 435/252.3; 435/254.11; 530/350; 530/300; 436/501; 536/23.1; 536/23.5
(58) Field of Classification Search ................. None
See application file for complete search history.

(56) References Cited

FOREIGN PATENT DOCUMENTS

| CA | 2365397 A1 | 10/2000 |
|---|---|---|
| CA | 2401670 A1 | 9/2001 |
| EP | 892050 A2 | 1/1999 |
| EP | 1 174 503 A1 | 1/2002 |
| JP | 11-106400 | 4/1999 |
| WO | WO 00/60075 A1 | 10/2000 |
| WO | WO 01/64896 A2 | 9/2001 |

OTHER PUBLICATIONS

McGuiness et al. (1991, The Lancet 337:514-7).*
Daniel et al. (1994, Virology 202 :540-9).*
Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Genbank, Accession No. AF132963, Lai, C.H. et al., Apr. 26, 1999.
Genbank, Accession No. AB028863, Sha S. et al., Jun. 19, 1999.
DATABASE EMBL 'Online! (Jun. 18, 1999) "*Mus musculus* mRNA for MMRP19, complete cds." XP002307155 retrieved from EBI accession No. EM_PRO:AB028863 Database accession No. AB028863.
DATABASE UniProt 'Online! (Nov. 1, 1999) "MMRP19 (CDNA sequence AB028863)." XP002307156 retrieved from EBI accession No. UNIPROT:Q9WVQ5 Database accession No. Q9WVQ5.
DATABASE EMBL 'Online! (Apr. 27, 1999) "*Homo sapiens* CGI-29 protein mRNA, complete cds." XP002307157 retrieved from EBI accession No. EM_PRO:AF132963 Database accession No. AF132963.
Nishi, Y. et al., Proceedings of Biotechnology Symposium, vol. 15, pp. 159-0164 (1997).
Nishi, Y. et al., Proceedings of Biotechnology Symposium, vol. 16, pp. 161-166 (1998).
Aoki, Y. et al, J. Leukoc. Biol. vol. 68, No. 5, pp. 757-764, (2000).
Nishi, Yoshisuke et al., Bio-Technology Symposium Yokoushuu, vol. 16, pp. 161-166, (1998).
Nishi, Yoshisuke et al., Bio-Technology Symposium Yokoushuu, vol. 15, pp. 159-164, (1997).

* cited by examiner

*Primary Examiner*—Elizabeth C. Kemmerer
(74) *Attorney, Agent, or Firm*—Birch, Stewart, Kolasch & Birch, LLP

(57) ABSTRACT

The present invention provides, as a gene encoding an antigen recognized by a G-CSF inducing antibody, a gene encoding any one of the following proteins: (a) a protein having an amino acid sequence shown in SEQ ID NO: 2; (b) a protein having an amino acid sequence comprising a deletion, substitution, addition or insertion of one or several amino acids with respect to the amino acid sequence shown in SEQ ID NO: 2, and having a binding ability for an antibody which induces and secretes a granulocyte colony-stimulating factor or a fragment thereof: or (c) a protein having at least 50% or more homology with the amino acid sequence shown in SEQ ID NO: 2, and having a binding ability for an antibody capable of inducing and secreting a granulocyte colony-stimulating factor or a fragment thereof.

15 Claims, 18 Drawing Sheets

(A) 3-4H7 STIMULATION (B) LPS STIMULATION

SEQUENCE LISTING

<160> NUMBER OF SEQ ID NOS: 17

<210> SEQ ID NO 1
<211> LENGTH: 840
<212> TYPE: DNA
<213> ORGANISM: Mouse macrophage cell RAW 264.7

<400> SEQUENCE: 1

```
gaacc atg tct ggc tgt caa gct caa gga gac tgt tgc tcg cgg ccg tgt         50
      Met Ser Gly Cys Gln Ala Gln Gly Asp Cys Cys Ser Arg Pro Cys
      1               5                   10                  15 ggc gcg cag gac aag gag cac ccc cga ttc ctg atc cca gaa ctt tgc           98
Gly Ala Gln Asp Lys Glu His Pro Arg Phe Leu Ile Pro Glu Leu Cys
                20                  25                  30 aaa cag ttt tac cat ctg ggc tgg gtc act ggc act gga ggg gga atc          146
Lys Gln Phe Tyr His Leu Gly Trp Val Thr Gly Thr Gly Gly Gly Ile
        35                  40                  45 agc ttg aag cat ggc aat gaa atc tac att gct ccc tca ggc gtg caa          194
Ser Leu Lys His Gly Asn Glu Ile Tyr Ile Ala Pro Ser Gly Val Gln
    50                  55                  60 aag gag cgc att cag cca gaa gac atg ttt gtg tgt gac att aat gag          242
Lys Glu Arg Ile Gln Pro Glu Asp Met Phe Val Cys Asp Ile Asn Glu
65                  70                  75 cag gac ata agc ggg cct cca gca tct aag aag ctg aaa aaa agc cag          290
Gln Asp Ile Ser Gly Pro Pro Ala Ser Lys Lys Leu Lys Lys Ser Gln
80                  85                  90                  95 tgc act cct ctt ttc atg aat gct tat acc atg aga gga gct ggc gca          338
Cys Thr Pro Leu Phe Met Asn Ala Tyr Thr Met Arg Gly Ala Gly Ala
                100                 105                 110 gtg att cat acc cac tct aaa gct gct gtg atg gct acc ctt ctg ttt          386
Val Ile His Thr His Ser Lys Ala Ala Val Met Ala Thr Leu Leu Phe
            115                 120                 125 cca gga cag gag ttt aaa att aca cat caa gag atg atc aaa gga ata          434
Pro Gly Gln Glu Phe Lys Ile Thr His Gln Glu Met Ile Lys Gly Ile
        130                 135                 140 agg aaa tgt acc tca gga ggc tat tac aga tac gat gat atg tta gtg          482
Arg Lys Cys Thr Ser Gly Gly Tyr Tyr Arg Tyr Asp Asp Met Leu Val
    145                 150                 155 gta cct att att gag aac act cct gaa gag aag gat ctc aaa gaa agg          530
Val Pro Ile Ile Glu Asn Thr Pro Glu Glu Lys Asp Leu Lys Glu Arg
160                 165                 170                 175 atg gct cat gcc atg aat gag tac cca gac tcc tgt gcg gtt ctt gtc          578
Met Ala His Ala Met Asn Glu Tyr Pro Asp Ser Cys Ala Val Leu Val
                180                 185                 190 cgg cgt cat ggg gtg tac gtg tgg gga gaa aca tgg gag aaa gca aaa          626
Arg Arg His Gly Val Tyr Val Trp Gly Glu Thr Trp Glu Lys Ala Lys
            195                 200                 205 acc atg tgt gag tgt tat gac tac ctg ttt gac att gct gtc tcc atg          674
Thr Met Cys Glu Cys Tyr Asp Tyr Leu Phe Asp Ile Ala Val Ser Met
        210                 215                 220 aag aag atg gga ctc gat cca aca cag ctc cca gtt gga gaa aat gga          722
Lys Lys Met Gly Leu Asp Pro Thr Gln Leu Pro Val Gly Glu Asn Gly
225                 230                 235 att gtg taa gccaagtgga tgcctaagca tctccaacaa taaacaaac tcaattatgc        781
Ile Val
240 cttaaataaa actcagctgc ttttaaaaaa aaaaaaaaaa aaaaaaaaaa aaaaaaaa          840
```

```
<210> SEQ ID NO 2
<211> LENGTH: 241
<212> TYPE: PRT
<213> ORGANISM: Mouse macrophage cell RAW 264.7

<400> SEQUENCE: 2

Met Ser Gly Cys Gln Ala Gln Gly Asp Cys Cys Ser Arg Pro Cys
 1               5                  10                  15

Gly Ala Gln Asp Lys Glu His Pro Arg Phe Leu Ile Pro Glu Leu Cys
                 20                  25                  30

Lys Gln Phe Tyr His Leu Gly Trp Val Thr Gly Thr Gly Gly Ile
                 35                  40                  45

Ser Leu Lys His Gly Asn Glu Ile Tyr Ile Ala Pro Ser Gly Val Gln
                 50                  55                  60

Lys Glu Arg Ile Gln Pro Glu Asp Met Phe Val Cys Asp Ile Asn Glu
 65                  70                  75

Gln Asp Ile Ser Gly Pro Pro Ala Ser Lys Lys Leu Lys Lys Ser Gln
 80                  85                  90                  95

Cys Thr Pro Leu Phe Met Asn Ala Tyr Thr Met Arg Gly Ala Gly Ala
                100                 105                 110

Val Ile His Thr His Ser Lys Ala Ala Val Met Ala Thr Leu Leu Phe
                115                 120                 125

Pro Gly Gln Glu Phe Lys Ile Thr His Gln Glu Met Ile Lys Gly Ile
                130                 135                 140

Arg Lys Cys Thr Ser Gly Gly Tyr Tyr Arg Tyr Asp Asp Met Leu Val
145                 150                 155

Val Pro Ile Ile Glu Asn Thr Pro Glu Glu Lys Asp Leu Lys Glu Arg
160                 165                 170                 175

Met Ala His Ala Met Asn Glu Tyr Pro Asp Ser Cys Ala Val Leu Val
                180                 185                 190

Arg Arg His Gly Val Tyr Val Trp Gly Glu Thr Trp Glu Lys Ala Lys
                195                 200                 205

Thr Met Cys Glu Cys Tyr Asp Tyr Leu Phe Asp Ile Ala Val Ser Met
                210                 215                 220

Lys Lys Met Gly Leu Asp Pro Thr Gln Leu Pro Val Gly Glu Asn Gly
225                 230                 235

Ile Val
240

<210> SEQ ID NO 3
<211> LENGTH: 1136
<212> TYPE: DNA
<213> ORGANISM: Homo sapiens

<400> SEQUENCE: 3
aagccgtgcg gagattggag gccgcgcggg tccctggtct gggcc                45 atg tct ggc tgt gat gct tgg gag gga gac tgt tgt tcc cgg aga tgc    93
Met Ser Gly Cys Asp Ala Trp Glu Gly Asp Cys Cys Ser Arg Arg Cys
 1               5                  10                  15 ggc gcg cag gac aag gag cat cca aga tac ctg atc cca gaa ctt tgc   141
Gly Ala Gln Asp Lys Glu His Pro Arg Tyr Leu Ile Pro Glu Leu Cys
                 20                  25                  30 aaa cag ttt tac cat tta ggc tgg gtc act ggg act gga gga att        189
Lys Gln Phe Tyr His Leu Gly Trp Val Thr Gly Thr Gly Gly Ile
                 35                  40                  45 agc ttg aag cat ggc gat gaa atc tac att gct cct tca gga gtg caa   237
Ser Leu Lys His Gly Asp Glu Ile Tyr Ile Ala Pro Ser Gly Val Gln
```

```
                50                      55                      60
aag gaa cga att cag cct gaa gac atg ttt gtt tat gat ata aat gaa        285
Lys Glu Arg Ile Gln Pro Glu Asp Met Phe Val Tyr Asp Ile Asn Glu
 65              70                  75                  80 aag gac ata agt gga cct tcg cca tcg aag aag cta aaa aaa agc cag        333
Lys Asp Ile Ser Gly Pro Ser Pro Ser Lys Lys Leu Lys Lys Ser Gln
             85                  90                  95 tgt act cct ctt ttc atg aat gct tac aca atg aga gga gca ggt gca        381
Cys Thr Pro Leu Phe Met Asn Ala Tyr Thr Met Arg Gly Ala Gly Ala
        100                 105                 110 gtg att cat acc cac tct aaa gct gct gtg atg gcc acc ctt ctc ttt        429
Val Ile His Thr His Ser Lys Ala Ala Val Met Ala Thr Leu Leu Phe
    115                 120                 125 cca gga cgg gag ttt aaa att aca cat caa gag atg ata aaa gga ata        477
Pro Gly Arg Glu Phe Lys Ile Thr His Gln Glu Met Ile Lys Gly Ile
130                 135                 140 aag aaa tgt act tcc gga ggg tat tat aga tat gat gat atg tta gtg        525
Lys Lys Cys Thr Ser Gly Gly Tyr Tyr Arg Tyr Asp Asp Met Leu Val
145                 150                 155                 160 gta ccc att att gag aat aca cct gag gag aaa gac ctc aaa gat aga        573
Val Pro Ile Ile Glu Asn Thr Pro Glu Glu Lys Asp Leu Lys Asp Arg
             165                 170                 175 atg gct cat gca atg aat gaa tac cca gac tcc tgt gca gta ctg gtc        621
Met Ala His Ala Met Asn Glu Tyr Pro Asp Ser Cys Ala Val Leu Val
         180                 185                 190 aga cgt cat gga gta tat gtg tgg ggg gaa aca tgg gag aag gcc aaa        669
Arg Arg His Gly Val Tyr Val Trp Gly Glu Thr Trp Glu Lys Ala Lys
     195                 200                 205 acc atg tgt gag tgt tat gac tat tta ttt gat att gcc gta tca atg        717
Thr Met Cys Glu Cys Tyr Asp Tyr Leu Phe Asp Ile Ala Val Ser Met
210                 215                 220 aag aaa gta gga ctt gat cct tca cag ctc cca gtt gga gaa aat gga        765
Lys Lys Val Gly Leu Asp Pro Ser Gln Leu Pro Val Gly Glu Asn Gly
225                 230                 235                 240 att gtc taa gccaaaagaa agtctaatta tatacagaga taaagctaaa               814
Ile Val cgtaattatt atttaaatga aagctatttt tttaaatgaa ttgaaatttt tcatgatgct      874
actaatttgc cactaaatac tgcaaatggt caccctgaat ctcttctgac attggatgtt      934
atttgcttat attcttataa ttttaaatga gggcacagtg aaatgaaaat tttatactct      994
atgtttctgt ttatttttaa atccttaaca gcaaatatt tgcctttaat ttcttttta     1054 tatatactct cagagaattc ctcttaattt ttaaagatgc tggtgataat aaaattcatt     1114
agaaaataaa aaaaaaaaa aa                                               1136

<210> SEQ ID NO 4
<211> LENGTH: 242
<212> TYPE: PRT
<213> ORGANISM: Homo sapiens

<400> SEQUENCE: 4

Met Ser Gly Cys Asp Ala Trp Glu Gly Asp Cys Cys Ser Arg Arg Cys
 1                5                  10                  15

Gly Ala Gln Asp Lys Glu His Pro Arg Tyr Leu Ile Pro Glu Leu Cys
             20                  25                  30

Lys Gln Phe Tyr His Leu Gly Trp Val Thr Gly Thr Gly Gly Gly Ile
         35                  40                  45

Ser Leu Lys His Gly Asp Glu Ile Tyr Ile Ala Pro Ser Gly Val Gln
```

```
            50                  55                  60
Lys Glu Arg Ile Gln Pro Glu Asp Met Phe Val Tyr Asp Ile Asn Glu
 65                  70                  75                  80

Lys Asp Ile Ser Gly Pro Ser Pro Ser Lys Lys Leu Lys Lys Ser Gln
                 85                  90                  95

Cys Thr Pro Leu Phe Met Asn Ala Tyr Thr Met Arg Gly Ala Gly Ala
                100                 105                 110

Val Ile His Thr His Ser Lys Ala Ala Val Met Ala Thr Leu Leu Phe
                115                 120                 125

Pro Gly Arg Glu Phe Lys Ile Thr His Gln Glu Met Ile Lys Gly Ile
130                 135                 140

Lys Lys Cys Thr Ser Gly Gly Tyr Tyr Arg Tyr Asp Asp Met Leu Val
145                 150                 155                 160

Val Pro Ile Ile Glu Asn Thr Pro Glu Glu Lys Asp Leu Lys Asp Arg
                165                 170                 175

Met Ala His Ala Met Asn Glu Tyr Pro Asp Ser Cys Ala Val Leu Val
                180                 185                 190

Arg Arg His Gly Val Tyr Val Trp Gly Glu Thr Trp Glu Lys Ala Lys
                195                 200                 205

Thr Met Cys Glu Cys Tyr Asp Tyr Leu Phe Asp Ile Ala Val Ser Met
210                 215                 220

Lys Lys Val Gly Leu Asp Pro Ser Gln Leu Pro Val Gly Glu Asn Gly
225                 230                 235                 240

Ile Val
```

<210> SEQ ID NO 5
<211> LENGTH: 19
<212> TYPE: DNA
<213> ORGANISM: Artificial Sequence
<220> FEATURE:
<223> OTHER INFORMATION: PCR sense primer

<400> SEQUENCE: 5
ccatgtctgg ctgtcaagc                                            19

<210> SEQ ID NO 6
<211> LENGTH: 21
<212> TYPE: DNA
<213> ORGANISM: Artificial Sequence
<220> FEATURE:
<223> OTHER INFORMATION: PCR antisense primer

<400> SEQUENCE: 6
ccattttctc caactgggag c                                         21

<210> SEQ ID NO 7
<211> LENGTH: 23
<212> TYPE: DNA
<213> ORGANISM: Artificial Sequence
<220> FEATURE:
<223> OTHER INFORMATION: PCR antisense primer

<400> SEQUENCE: 7
aattcctcct ccagtcccag tga                                       23

<210> SEQ ID NO 8
<211> LENGTH: 24
<212> TYPE: DNA
<213> ORGANISM: Artificial Sequence
<220> FEATURE:

```
<223> OTHER INFORMATION: PCR sense primer

<400> SEQUENCE: 8
tggagtatat gtgtgggggg aaac                                          24

<210> SEQ ID NO 9
<211> LENGTH: 21
<212> TYPE: DNA
<213> ORGANISM: Artificial Sequence
<220> FEATURE:
<223> OTHER INFORMATION: PCR sense primer

<400> SEQUENCE: 9
aagccgtgcg gagattggag g                                             21

<210> SEQ ID NO 10
<211> LENGTH: 23
<212> TYPE: DNA
<213> ORGANISM: Artificial Sequence
<220> FEATURE:
<223> OTHER INFORMATION: PCR antisense primer

<400> SEQUENCE: 10
gtcagaagag attcagggtg acc                                           23

<210> SEQ ID NO 11
<211> LENGTH: 18
<212> TYPE: DNA
<213> ORGANISM: Artificial Sequence
<220> FEATURE:
<223> OTHER INFORMATION: PCR sense primer

<400> SEQUENCE: 11
gctgtggcaa agtgcact                                                 18

<210> SEQ ID NO 12
<211> LENGTH: 18
<212> TYPE: DNA
<213> ORGANISM: Artificial Sequence
<220> FEATURE:
<223> OTHER INFORMATION: PCR antisense primer

<400> SEQUENCE: 12
atctgctgcc agatggtg                                                 18

<210> SEQ ID NO 13
<211> LENGTH: 21
<212> TYPE: DNA
<213> ORGANISM: Artificial Sequence
<220> FEATURE:
<223> OTHER INFORMATION: mG-CSF forward primer

<400> SEQUENCE: 13
cagcagacac agtgcctaag c                                             21

<210> SEQ ID NO 14
<211> LENGTH: 21
<212> TYPE: DNA
<213> ORGANISM: Artificial Sequence
<220> FEATURE:
<223> OTHER INFORMATION: mG-CSF reverse primer

<400> SEQUENCE: 14
agttggcaac atccagctga a                                             21
```

```
<210> SEQ ID NO 15
<211> LENGTH: 19
<212> TYPE: DNA
<213> ORGANISM: Artificial Sequence
<220> FEATURE:
<223> OTHER INFORMATION: mGAPDH forward primer

<400> SEQUENCE: 15
tgcaccacca actgcttag                                                19

<210> SEQ ID NO 16
<211> LENGTH: 19
<212> TYPE: DNA
<213> ORGANISM: Artificial Sequence
<220> FEATURE:
<223> OTHER INFORMATION: mGAPDH reverse primer

<400> SEQUENCE: 16
ggatgcaggg atgatgttc                                                19

<210> SEQ ID NO 17
<211> LENGTH: 23
<212> TYPE: DNA
<213> ORGANISM: Artificial Sequence
<220> FEATURE:
<223> OTHER INFORMATION: probe used for mGAPDH

<400> SEQUENCE: 17
cagaagactg tggatggccc ctc                                           23
```

PROTEINS, GENES ENCODING THEM AND METHOD OF USING THE SAME

This application is the national phase under 35 U.S.C. § 371 of PCT International Application No. PCT/JP01/08446 which has an International filing date of Sep. 27, 2001, which designated the United States of America.

TECHNICAL FIELD

The present invention relates to a protein having reactivity with an antibody capable of inducing and secreting a granulocyte colony-stimulating factor, a gene encoding the protein, and using method thereof.

BACKGROUND ART

Granulocyte colony-stimulating factor (G-CSF) has a molecular weight of approximately 18,000 to 22,000. This factor is a glycoprotein, which induces the differentiation and proliferation of one type of a blood component leukocyte, neutrophil. This glycoprotein is comprised of 174 amino acids (occasionally 178 amino acids) in the case of human, and it is composed of 178 amino acids in the case of mouse.

G-CSF affects to enhance the survival and function of mature neutrophils, the formation of erythroblasts by an erythropoietin, and the formation of blast cell colonies by interleukin-3. Moreover, G-CSF promotes (reinforces the function and increases the numbers of) blood cells such as leukocytes, erythrocytes or thrombocytes. Examples of the cells generating G-CSF include macrophages, stromal cells, monocytes, T lymphocytes, fibroblasts, vascular endothelial cells and others.

Administration of G-CSF as a therapuetic agent has an effect for treatment of neutropenia as a side effect of an anticancer agent, neutropenia occurring after bone marrow transplantation, and aplastic anemia. However, when G-CSF is administered, it requires frequent administration because of its low stability in the blood, and further, the administration route is limited to intravenous or subcutaneous administration. Therefore, the use of G-CSF as a therapeutic agent is painful for patients and imposing the burden to doctors. Moreover, it has been reported that bone ache occurs as a side effect when G-CSF is therapeutically administered. Direct administration of macrophages or stroma cells, which produce G-CSF, has not been carried out, since these cells happen to contain various types of proteins or substances and so unexpected side effects might occur.

As stated above, a method of differentiating and growing neutrophils by the direct administration of G-CSF elicits bone ache as a side effect and requires frequent administration, thereby giving a certain pain and burden to both patients and doctors. Accordingly, the development of another treatment method is strongly required, but it has not been established up till now.

Thus, the present inventors have intended that G-CSF is not directly administered but G-CSF is allowed to be produced and as a result neutrophils are differentiated and grown, and they have previously succeeded in providing a G-CSF-inducing antibody (Japanese Patent Application No. 9-266591 (Sep. 30, 1997) and Japanese Patent Laid-Open No. 11-106400 (Apr. 20, 1999). However, an antigen recognized by the G-CSF inducing antibody has not been clarified.

SUMMARY OF THE INVENTION

The present invention provides, as a gene encoding an antigen recognized by an antibody capable of inducing and secreting G-CSF, a gene encoding a protein (a), (b) or (c) described as follows: (a) a protein having an amino acid sequence shown in SEQ. ID NO: 2; (b) a protein having an amino acid sequence comprising a deletion, substitution, addition or insertion of one or several amino acids with respect to the amino acid sequence shown in SEQ ID NO: 2, and having a binding ability for an antibody capable of inducing and secreting a G-CSF or a fragment thereof; or (c) a protein having at least 50% or more homology with the amino acid sequence shown in SEQ ID NO: 2, and having a binding ability for an antibody capable of inducing and secreting a G-CSF or a fragment thereof.

DISCLOSURE OF THE INVENTION

Figure 1:
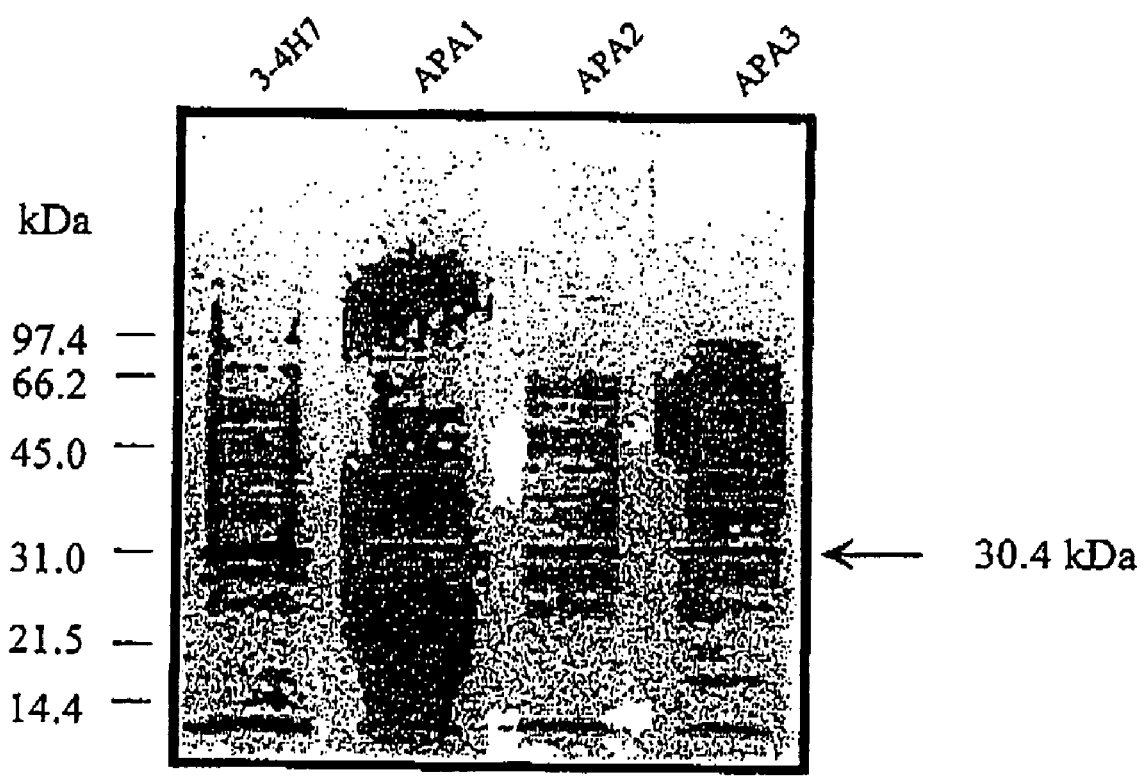
FIG. 1: Western Blot Analysis of a 3-4H7 antibody and anti-MMRP19 partial peptide antibodies (APAs).

It is an object of the present invention to specify an antigen recognized by a G-CSF inducing antibody. It is another object of the present invention to clone and identify a gene encoding the antigen recognized by the G-CSF inducing antibody.

Further, it is another object of the present invention to analyze in detail such an antigen protein and to clarify that the protein is associated with the induction of G-CSF gene expression and/or G-CSF protein secretion. Furthermore, it is another object of the present invention to provide a series of procedures for screening a compound which changes the generation of G-CSF gene expression and/or G-CSF protein induction, using the above protein.

During intensive studies directed towards the above objects, the present inventors have carried out the immunoscreening of a cDNA library derived from macrophage cells, using a monoclonal antibody with ability to induce G-CSF as a probe, As a result, the present inventors have succeeded in the isolation of a positive clone and they have determined its nucleotide sequence, thereby providing the present invention. Moreover, the present inventors have also determined the nucleotide sequence of a human counterpart antigen gene.

That is to say, the present invention provides a gene encoding a protein (a), (b) or (c) described as follows; (a) a protein having an amino acid sequence shown in SEQ ID NO: 2; (b) a protein having an amino acid sequence comprising a deletion, substitution, addition or insertion of one or several amino acids with respect to the amino acid sequence shown in SEQ ID NO: 2, and having a binding ability for an antibody capable of inducing and secreting a G-CSF or a fragment thereof; or (c) a protein having at least 50% or more homology with the amino acid sequence shown in SEQ ID NO: 2, and having a binding ability for an antibody capable of inducing and secreting a G-CSF or a fragment thereof.

Moreover, the present invention provides a gene encoding a protein (a), (b) or (c) described as follows: (a) a protein having an amino acid sequence shown in SEQ ID NO: 4; (b) a protein having an amino acid sequence comprising a deletion, substitution, addition or insertion of one or several amino acids with respect to the amino acid sequence shown in SEQ ID NO: 4, and having a binding ability for an antibody capable of inducing and secreting a G-CSF or a fragment thereof; or (c) a protein having at least 50% or more homology with the amino acid sequence shown in SEQ ID NO: 4, and having a binding ability for an antibody capable of inducing and secreting a G-CSF or a fragment thereof.

Further, the present invention provides a gene having a nucleotide sequence (a), (b) or (c) described as follows: (a) a nucleotide sequence shown in SEQ ID NO: 1; (b) a nucleotide sequence comprising a deletion, substitution, addition or insertion of one or several nucleotides with respect to the nucleotide sequence shown in SEQ ID NO: 1, and encoding a protein having a binding ability for an antibody capable of inducing and secreting a G-CSF or a fragment thereof; or (c) a nucleotide sequence which hybridizes with DNA having the nucleotide sequence shown in SEQ ID NO: 1 under stringent conditions, and encoding a protein having a binding ability for an antibody capable of inducing and secreting a G-CSF or a fragment thereof.

Furthermore, the present invention provides a gene having a nucleotide sequence (a). (b) or (c) described as follows: (a) a nucleotide sequence shown in SEQ ID NO: 3; (b) a nucleotide sequence comprising a deletion, substitution, addition or insertion of one or several nucleotides with respect to the nucleotide sequence shown in SEQ ID NO: 3, and encoding a protein having a binding ability for an antibody capable of inducing and secreting a G-CSF or a fragment thereof; or (c) a nucleotide sequence which hybridizes with DNA having the nucleotide sequence shown in SEQ ID NO; 3 under stringent conditions and encoding a protein having a binding ability for an antibody capable of inducing and secreting a G-CSF or a fragment thereof.

In the above description, the antibody capable of inducing and secreting a G-CSF is, for example, a monoclonal antibody produced from hybridoma cells deposited under accession No. FERM BP-6103.

The gene of the present invention is, for example, a gene derived from mouse or human.

The present invention provides a DNA fragment comprising any of the following nucleotide sequences: (1) a nucleotide sequence consisting of nucleotides 519 to 736, nucleotides 666 to 689, nucleotides 381 to 403, or nucleotides 709 to 727 with respect to the nucleotide sequence shown in SEQ ID NO: 1: (2) a nucleotide sequence comprising a deletion, substitution, addition or insertion of one or several nucleotides with respect to the nucleotide sequence of (1) above; and (3) a nucleotide sequence having at least 80% homology with any one of the nucleotide sequences of (1) above.

Moreover, the present invention provides a gene having any one of the following nucleotide sequences: (1) a nucleotide sequence consisting of nucleotides 519 to 736, nucleotides 666 to 689. nucleotides 381 to 403, or nucleotides 709 to 727 with respect to the nucleotide sequence shown in SEQ ID NO: 1: (2) a nucleotide sequence comprising a deletion, substitution, addition or insertion of one or several nucleotides with respect to the nucleotide sequence of (1) above: and (3) a nucleotide sequence having homology of at least 80% with any one of the nucleotide sequences of (1) above, and encoding a protein having a binding ability for an antibody capable of inducing and secreting a G-CSF or a fragment thereof.

Further, the present invention provides a protein (a), (b), (c) or (d) described as follows: (a) a protein having an amino acid sequence shown in SEQ ID NO: 2; (b) a protein having an amino acid sequence comprising a deletion, substitution, addition or insertion of one or several amino acids with respect to the amino acid sequence shown in SEQ ID NO: 2, and having a binding ability for an antibody capable of inducing and secreting a G-CSF or a fragment thereof: (c) a protein having at least 50% or more homology with the amino acid sequence shown in SEQ ID NO: 2, and having a binding ability for an antibody capable of inducing and secreting a G-CSF or a fragment thereof: or (d) a protein encoded by DNA which hybridizes with DNA having the nucleotide sequence shown in SEQ ID NO: 1 under stringent conditions, and having a binding ability for an antibody capable of inducing and secreting a G-CSF or a fragment thereof.

Furthermore, the present invention provides a protein (a), (b), (c) or (d) described as follows: (a) a protein having an amino acid sequence shown in SEQ ID NO: 4; (b) a protein having an amino acid sequence comprising a deletion, substitution, addition or insertion of one or several amino acids with respect to the amino acid sequence shown in SEQ ID NO: 4, and having a binding ability for an antibody capable of inducing and secreting a G-CSF or a fragment thereof: (c) a protein having at least 50% or more homology with the amino acid sequence shown in SEQ ID NO: 4, and having a binding ability for an antibody capable of inducing and secreting a G-CSF or a fragment thereof; or (d) a protein encoded by DNA which hybridizes with DNA having the nucleotide sequence shown in SEQ ID NO: 3 under stringent conditions, and having a binding ability for an antibody capable of inducing and secreting a G-CSF or a fragment thereof.

In the above description, the antibody capable of inducing and secreting a G-CSF is, for example, a monoclonal antibody produced from hybridoma cells deposited under accession No. FERM BP-6103.

The protein of the present invention is derived preferably from mammal and particularly preferably from mouse or human.

The present invention provides a protein having any one of the following amino acid sequences: (1) an amino acid sequence consisting of amino acids 1 to 91, amino acids 50 to 146, amino acids 1 to 78, amino acids 200 to 241, amino acids 172 to 241, amino acids 103 to 150, or amino acids 169 to 241 with respect to the amino acid sequence shown in SEQ ID NO: 2; (2) an amino acid sequence comprising a deletion, substitution, addition or insertion of one or several amino acids with respect to the amino acid sequence of (1)

above; and (3) an amino acid sequence having at least 70% homology with any one of the amino acid sequences of (1) above.

Moreover, the present invention provides a protein having any one of the following amino acid sequences; (1) an amino acid sequence consisting of amino acids 1 to 91, amino acids 50 to 146, amino acids 1 to 78, amino acids 200 to 241, amino acids 172 to 241, amino acids 103 to 150, or amino acids 169 to 241 with respect to the amino acid sequence shown in SEQ ID NO: 2: (2) an amino acid sequence comprising a deletion, substitution, addition or insertion of one or several amino acids with respect to the amino acid sequence of (1) above: and (3) an amino acid sequence having at least 70% homology with any one of the amino acid sequences of (1) above, and having a binding ability for an antibody capable of inducing and secreting a G-CSF or a fragment thereof.

Further, the present invention provides an antibody against the abovedescribed protein of the present invention or a fragment thereof. The antibody is preferably a monoclonal antibody, and particularly preferably a human-type monoclonal antibody or human monoclonal antibody.

Furthermore, the present invention provides a recombinant vector comprising the gene of the present invention or a DNA fragment thereof.

Furthermore, the present invention provides a transformant comprising a recombinant vector comprising the gene of the present invention or a DNA fragment thereof.

Furthermore, the present invention provides a novel receptor or a portion thereof (the protein of the present invention) which is capable of inducing or promoting the secretion of a G-CSF.

Furthermore, the present invention provides a method of screening a useful substance (e.g. an agonist or antagonist of the protein of the present invention) by using the protein of the present invention, a substance obtained by the screening method and a useful substance capable of binding to a receptor (e.g. an agonist or antagonist of the receptor.)

Furthermore, the present invention provides a pharmaceutical composition comprising the gene, DNA fragment, protein (including a fragment of the protein) antibody (including a fragment thereof), receptor, or substance (including a low molecular compound) of the present invention (the pharmaceutical composition particularly used for diagnosis, prevention or treatment of infectious diseases, neutropenia, or cytopenia regarding the reduction of the number of erythrocytes, leukocytes or thrombocytes); and a treatment method of using the pharmaceutical composition.

The embodiments and methods for carrying out the present invention will be explained in detail below.

Prior to the present invention, the present inventors obtained an antibody by the immunization of a macrophage itself, and they succeeded in isolating an antibody which induces G-CSF from the obtained antibody (Japanese Patent Application No. 9-266591; the disclosure of this application is incorporated herein by reference in its entirety). The gene of the present invention was isolated by screening a cDNA library derived from the mouse macrophage, using this antibody as a probe. The protein encoded by the gene of the present invention is characterized in that it has a binding ability to an antibody capable of inducing and secreting a G-CSF or a fragment thereof.

<Antibody which Induces or Promotes Secretion of G-CSF, or Fragment Thereof>

First, with regard to "an antibody which induces or promotes secretion of G-CSF or a fragment thereof" of the present specification (hereinafter referred to also as "antibody used in the present invention"), a method of obtaining the same or the like will be explained.

First, the present inventors administered cells of the mouse macrophage cell line as an antigen to MRL/lpr mice (autoimmune-disease mouse) and isolated a monoclonal antibody. Then they treated the obtained moloclonal antibodies to the immunized cell, a mouse macrophage cell line, in order to study the effect of the antibody to the immunized cell. As a result, they found that one of the obtained antibodies has a property to concentration-dependently induce G-CSF from the immunized cell line, the mouse macrophage cell line (a hybridoma producing this antibody is deposited under international accession No. FERM BP-6103).

The term "monoclonal antibody" is used in the present specification to mean a monoclonal antibody having reactivity with a macrophage cell line, and specifically, it is a monoclonal antibody having an activity which promotes the generation of G-CSF.

The antibody used in the present invention has a property to substantially bind to a macrophage cell line. The antibody used in the present invention includes both a polyclonal antibody and a monoclonal antibody, which have the above-described property. Moreover, the "monoclonal antibody" includes monoclonal antibodies belonging to any immunoglobulin class such as IgG, IgM, IgA, IgD and IgE, and it is preferably an IgG or IgM immunoglobulin class monoclonal antibody.

The macrophage cell line can be prepared from spontaneous leukemic cells, or it can be also prepared by cellular transformation by leukemic viruses.

The antibody used in the present invention can be obtained according to the conventional methods (e.g. a method described in the publication "Zoku Seikagaku Jikken Koza 5, Meneki Seikagaku Kenkyu Ho, edited by The Japanese Biochemical Society, published by Tokyo Kagaku Dojin Co. Ltd.).

The monoclonal antibody used in the present invention can be produced from a hybridoma (a hybrid cell) which is produced by what is called cell fusion. That is to say, a hybridoma is obtained from an antibody generating cell and a myeloma cell, the obtained hybridoma is cloned, and using all or a part of macrophage cell lines as an antigen, a clone generating an antibody showing a specific affinity toward the antigen is selected as the monoclonal antibody used in the present invention. To produce the monoclonal antibody, previously known methods can be applied with the exception that all or a part of macrophage cell lines is used as an immunogen.

The immunogen is obtained by, for example, the direct use of a macrophage cell line, or it is prepared by mixing the whole or a portion of the membrane fraction or soluble extract of a macrophage cell line with e.g. a complete Freund's adjuvant as necessary. Examples of animals used as the target of immunization include mammals such as mouse, rat, guinea pig, hamster or rabbit, preferably mouse or rat, and particularly preferably mouse. Immunization is carried out by injection one to several times into the subcutis, muscle, vein, footpad or peritoneal cavity of the above described mammals.

Generally, the subsequent immunization is carried out once to four times about every one to two weeks after the initial immunization, and then about one to four weeks later, the final immunization is carried out. About three to five days after the final immunization, antibody producing cells are collected from the immunized aminal.

The monoclonal antibody used in the present invention includes a monoclonal antibody (3-4H7 antibody) produced from hybridoma cells deposited under "international accession No. FERN BP-6103", a fragment thereof, and an antibody having substantially the same properties as the above antibody. The "3-4H7 antibody" has an ability to generate G-CSF from the cells.

The hybridoma producing the monoclonal antibody used in the present invention can be prepared by known methods. Such known methods include, for example, Köhler and Milstein's method (Nature, Vol. 256, pp. 495-497, 1975) and other modified methods equivalent thereto, for a preparation of a hydridoma which secretes a monoclonal antibody. That is, a monoclonal antibody can be prepared by culturing the hybrid cells (hybridomas), which are obtained by fusion between an antibody producing cells in the spleen, lymph node, bone marrow or tonsilla, preferably the spleen from the animal immunized as above, and myeloma cells (myelomas) obtained from preferably the same kind of mammal such as mouse, rat, guinea pig, hamster, rabbit or human, and more preferably from mouse, rat or human. Cultures can be carried out in vitro, or cells are grown in vivo, for example, in the ascites of mammals such as mouse, rat, guinea pig, hamster or rabbit, preferably of mouse or rat, and more preferably of mouse, and the antibody can be obtained from the culture supernatant or the ascites of the mammals.

Examples of myeloma cells used in a cell fusion include myelomas "P3/X63-AG8", "P3/NS1/1-Ag4-1", "P3/X63-Ag8.U1", "SP2/0-Ag14", "PAI", "FO" and "BW5147", which are derived from mouse, a myeloma "21ORCY3-Ag1.2.3", which is derived from rat, and myelomas "U-266AR1", "GM1500-6TG-A1-2", "UC729-6", "CEM-AGR", "D1R11" and "CEM-T15", which are derived from human.

Screening of a hybrid cell clone producing the monoclonal antibody used in the present invention can be carried out by culturing a hybrid cell, for example, in a microtiter plate, and determining the reactivity of an antigen of the culture supernatant in the well where proliferation of the cells is observed, for example, by flow cytometry or by enzymatic techniques such as RIA or ELISA.

Examples of a basal medium include low calcium-medium such as Ham's F12 medium, MCDB153 medium or low calcium-MEM medium: high calcium-medium such as MCDB104 medium, MEM medium, D-MEM medium, RPM11640 medium, ASF104 medium or RD medium; and others. Depending on purposes, to the above basal medium, sera, hormones, cytokines, and/or various inorganic or organic substances can be added. Isolation and purification of a monoclonal antibody can be carried out by subjecting the above described culture supernatant or ascites to collect antibodies by ammonium sulfate precipitation, euglobulin precipitation, caproic acid method, caprylic acid method, ion-exchange chromatography (DEAE, DE52 or the like), affinity column chromatography, which uses an anti-immunoglobulin column or a protein A or G column, hydrophobic chromatography, and others.

The monoclonal antibody used in the present invention can be obtained by any of the method, which are not limited to the above production methods. Generally, a "monoclonal antibody" has a sugar chain, the structure of which is different depending on the types of a mammal to be immunized. However, the "monoclonal antibody" used in the present invention is not limited by the structural difference of the sugar chain, but it includes monoclonal antibodies derived from any type of mammals. The "monoclonal antibody" used in the present invention includes: a monoclonal antibody produced by phage display; a human-type monoclonal antibody obtained by, for example, using a transgenic mouse, which is produced by introducing a human immunoglobulin gene through gene engineering so as to generate a human-type antibody; a chimeric monoclonal antibody obtained by substituting the constant region (Fc region) of a monoclonal antibody derived from a certain mammal with the Fe region of a human monoclonal antibody by genetic engineering techniques: and a humanized monoclonal antibody obtained by substituting the entire region other than complementarity-determining regions (CDRs), which have complementarily and directly binding to an antigen, with a corresponding region of human monoclonal antibody.

In the present invention, the "fragment of an antibody" may also be used. The term "the fragment of an antibody" is used herein to mean an antibody fragment comprising at least one variable region, and the term is the same definition as a "portion of an antibody" described in Japanese Patent Application No. 9-266591. Specifically, the antibody fragment refers to Fv, F(ab')2, Fab' or Fab. Each of the terms "F(ab')2" and "Fab" are used herein to mean an antibody fragment obtained by treating immunoglobulin (monoclonal antibody) with protease such as pepsin or papain and digesting before or after the disulfide bonds between two H chains in a hinge region. For example, when IgG is treated with papain, it is cleaved upstream of the disulfide bond between the two H chains in the hinge region, thereby producing two homologous antibody fragments in which an L chain fragment consisting of VL (an L chain variable region) and CL (an L chain constant region) and an H chain fragment consisting of VH (an H chain variable region) and CHγ1 (a γ1 region in an H chain constant region) are bound in a C-terminal region by a disulfide bond. Each of the two homologous antibody fragments is called Fab'. When IgG is treated with pepsin, it is cleaved downstream of the disulfide bonds between the two H chains in the hinge region, thereby producing an antibody fragment which is slightly larger than the above described two Fab's which are bound with each other in the hinge region. This antibody fragment is called F(ab')2.

The protein encoded by the gene of the present invention is characterized in that it has a binding ability to the antibody capable of inducing and secreting a G-CSF or a fragment thereof, as described in detail above. The term "affinity" is used in the present specification to mean an ordinary affinity between a protein and an antibody, and it can be determined by commonly used immunological analyses (e.g. immunoprecipitation method, ELISA, immunoblotting, etc.).

<Gene of the Present Invention>

The present invention provides a gene encoding a protein having an amino acid sequence shown in SEQ ID NO: 1 or a protein homologous to the above protein. The present invention further provides a gene having a nucleotide sequence shown in SEQ ID NO: 1 or a nucleotide sequence homologous to the above nucleotide sequence.

The type of the gene of the present invention is not particular limited. Any of native DNA, recombinant DNA and chemically synthesized DNA may be used, and further, a genomic DNA clone and a cDNA clone may also be used.

The gene of the present invention typically has a nucleotide sequence shown in SEQ ID NO: 1. This is the nucleotide sequence of a clone (MMR19) obtained in the examples as described later, which are provided for illustrative purposes only. It is well known to a person skilled in the art that native genes include a few mutants caused by the difference of the species of an organism which produces the genes, a few mutants caused by difference in the ecosystem, or by the presence of a very similar isozyme. Accordingly, the gene of the present invention is not limited to the gene having the nucleotide sequence shown in SEQ ID NO: 1, but it includes all the genes encoding the proteins having features described in the present specification.

The description "comprising a deletion, substitution, addition or insertion of one or several nucleotides" is used in the present specification to mean that a certain number of nucleotides are substituted by known techniques such as a site-directed mutagenesis, or these are spontaneously substituted. The number of nucleotides substituted is, for example, 10 or less, and preferably 3 to 5 or less.

If the amino acid sequence of the protein of the present invention and a DNA sequence encoding the same are disclosed in the present specification, using these sequences or portions thereof, a gene encoding a protein having similar physiological activity as the inventive protein can easily be isolated from other organisms by basic gene engineering techniques such as hybridization and PCR. In such a case, the thus obtained gene is also included in the scope of the present invention.

Hybridization conditions for screening homologous genes are not particularly limited. A person skilled in the art can appropriately select hybridization conditions, considering the level of homology between a homologous gene of interest and a probe. However, in general, stringent conditions are preferable, and an example includes hybridization conditions of 6×SSC [0.9 M NaCl, 0.09 M sodium citrate (pH 7.0)], 5× Denhardt's solution [1 g of ficoll. 1 g of polyvinylpyrrolidone and 1 g of BSA in 1,000 mL], 0.5% SDS, and 25° C. to 68° C. (for example, 37° C., 42° C. or 68° C.), or hybridization conditions of 0% to 50% formamide, 6×SSC, 0.5% SDS, and 25° C. to 68° C. (for example, 37° C., 42° C. or 68° C.). It is well known to those skilled in the art that DNA having a nucleotide sequence with more than a certain level of homology can be cloned by appropriately setting hybridization conditions such as formamide concentration, Denhardt's solution concentration, salt concentration and temperature. All the thus cloned homologous genes are also included in the scope of the present invention.

Homologous genes cloned by the above described hybridization have at least 70% or more, preferably 80% or more, more preferably 90% or more, particularly preferably 95% or more, and most preferably 98% or more homology with the nucleotide sequence of SEQ ID NO: 1.

<Protein of the Present Invention>

The present invention provides a protein having an amino acid sequence shown in SEQ ID NO: 1 or a protein having homology with the protein.

The protein having the amino acid sequence shown in SEQ ID NO: 1 of the present invention can be obtained by integrating a gene encoding the protein into a suitable expression vector and then transfecting the vector into a suitable host so that a recombinant protein is allowed to express therein. However, the origin or production method of the protein of the present invention is not limited, as long as the protein has features described in the present specification. Accordingly, any of a native protein, a protein expressed from recombinant DNA by genetic engineering, and chemically synthesized protein may be used.

The protein of the present invention typically has an amino acid sequence consisting of 241 amino acids shown in SEQ ID NO: 1. However, it is well known that native proteins include mutant proteins comprising one to several amino acid mutants, which are caused by the differenc of the species of an organism which produces the proteins, gene mutation caused by difference in the ecosystem, or the presence of a very similar isozyme. The term "amino acid mutants" are used herein to mean a substitution, deletion, insertion and/or addition of one or more amino acids. When an assumption is made from the nucleotide sequence of the cloned gene, the protein of the present invention has the amino acid sequence shown in SEQ ID NO: 1. However, the protein of the present invention is not limited to a protein having that amino acid sequence, but it is intended to include all homologous proteins, as long as they have features described in the present specification. The level of homology is at least 50% or more, preferably 60% or more, more preferably 70% or more, further preferably 80% or more, further more preferably 90% or more, particularly preferably 95% or more, and most preferably 98% or more.

Generally, when amino acids having similar features are substituted (e.g. substitution of hydrophobic amino acids, substitution of hydrophilic amino acids, substitution of acidic amino acids, or substitution of basic amino acids), in many cases, the obtained mutant protein has the same features as those of the original protein. A method of producing a recombinant protein by genetic engineering having certain desired mutations is well known to a person skilled in the art, and such a mutant protein is also included in the scope of the present invention.

When the description "a deletion, substitution, addition or insertion of one or several amino acids" is used for an amino acid sequence in the present specification, it means that a certain number of amino acids are substituted by known techniques such as a site-directed mutagenesis, or these are spontaneously substituted. The number of amino acids substituted is, for example, 10 or less, and preferably 3 to 5 or less. The term "homology" regarding amino acid sequences is used herein to mean the level of the correspondence between amino acid residues which constitute amino acid sequences to be compared. This time, the presence of gaps and the properties of amino acids are taken into consideration (Wilbur, Proc. Natl. Acad. Sci. USA 80: 726-730 (1983), etc.) In order to calculate homology, commercially available software such as BLAST (Altschul: J. Mol. Biol. 215: 403-410 (1990)), FASTA (Peasron: Methods in Enzymology 183: 63-69 (1990)), Genetyx-Mac (Software Development Co., Ltd.) and others can be used.

In examples described later in the present specification, cloning of cDNA derived from the mouse macrophage is shown as an example of the present invention. Isolation of a gene encoding a protein having the same physiological activity as the inventive protein from other origins by genetic engineering such as hybridization and PCR, using the amino acid sequence of the protein disclosed in the present specification the sequence of a gene encoding the protein (d rived from mouse) or a portion thereof, is within the common technical knowledge of a person skilled in the art, and a protein encoded by the thus isolated gene is also included in the scope of the present invention.

<Human-type Gene and Protein>

An example of a method for obtaining a human-derived homolog with respect to the gene and protein of the present invention is as follows.

Total RNA is extracted from human macrophage cell lines (THP-1, U937, HL-60) by guanidium thiocyanate/phenol chloroform single step extraction (LaboManual Gene Engineering, 3$^{rd}$ edition, pages 83 and 84, 1996), and the total RNA is then purified using an oligo(dT) cellulose column to obtain poly A$^+$RNA. Using reverse transcriptase (MMLV- RTase) and DNA polymerase I, double stranded cDNA is synthesized. A cDNA library is constructed from the obtained double stranded cDNA according to Gubler-Hoffmann method (Gubler, U. and Hoffmann. B., J.: Gene, 25: 263-269, 1983), using a λZAPII phage vector. Using a DNA sequence as a probe, which is amplified using the cDNA library of human macrophage cells as a template and using primers capable of amplifying a sequence in the region which has high homology with human (e.g. a region corresponding to nucleotides 172 to 241 of the nucleotide sequence shown in SEQ ID NO: 1, which has 91% homology with human) in the nucleotide sequence (SEQ ID NO: 1) of mouse cDNA (MMR19 clone) disclosed in the present specification: or directly using such a region (e.g. a region corresponding to nucleotides 172 to 241 of the nucleotide sequence shown in SEQ ID NO: 1) as a probe, the EDNA library of human macrophage cells is screened to isolate cDNA encoding the full length amino acid sequence of a protein of interest. Thereafter, according to Primer Walking method, the nucleotide sequence of the obtained cDNA is analyzed. After confirming that the cDNA encodes the full length of the protein of interest, the cDNA is introduced into baculovirus so as to allow it to express itself as a protein. Thereafter, the protein is purified using an affinity column so that a human-type homologue protein can be obtained.

As stated above, the present invention relates to a gene having the nucleotide sequence shown in SEQ ID NO: 1, a protein having the amino acid sequence shown in SEQ ID NO: 2, and genes and proteins having homology with the above gene and protein. A search was made regarding whether or not a nucleotide sequence and an amino acid sequence having homology with the nucleotide sequence shown in SEQ ID NO: 1 and the amino acid sequence shown in SEQ ID NO: 2, which are provided by the present invention are present in other organisms. As a result, it was confirmed that a gene having high homology with the gene of the present Invention is present in human EST (expressed sequence tag) (refer to Example 3 described later). Accordingly, it is clear that a human-derived homologue gene can also be isolated by screening a human-derived gene library (cDNA library, etc.), using, as a probe, human-derived EST having high homology with the nucleotide sequence of the present invention.

As stated above, the search through the database clarified that a portion of the nucleotide sequence shown in SEQ ID NO: 1 of the present invention (that is, a DNA fragment) is also present in human with high homology. Such a DNA fragment, as stated above, is useful as a probe when a human-derived homologue gene is screened, and it forms an aspect of the present invention. Examples of such a DNA fragment include a DNA fragment having any one of a nucleotide sequence consisting of nucleotides 519 to 736, a nucleotide sequence consisting of nucleotides 666 to 689, a nucleotide sequence consisting of nucleotides 381 to 403, and a nucleotide sequence consisting of nucleotides 709 to 727 with respect to the nucleotide sequence shown in SEQ ID NO: 1. Further, a DNA fragment having a nucleotide sequence comprising a deletion, substitution, addition or insertion of one or several nucleotides with respect to any one of the above nucleotide sequences; or a DNA fragment having a nucleotide sequence having at least 80%, preferably 85% or more, more preferably 90% or more, further preferably 95% or more, and most preferably 98% or more homology with any one of the above nucleotide sequences, is also within the scope of the present invention.

Moreover, the search through the database also clarified that a portion of the amino acid sequence shown in SEQ ID NO: 2 of the present invention is present in human with high homology. As with the protein of the present invention, a protein fragment consisting of a portion of the protein of the present invention is useful as a reagent for analyzing or isolating an antibody capable of inducing and secreting G-CSF, and as with the protein of the present invention, the protein fragment is likely to be used as a pharmaceutical. Accordingly, the protein fragment forms an aspect of the present invention.

Examples of such a protein include a protein having any one of an amino acid sequence consisting of amino acids 1 to 91, an amino acid sequence consisting of amino acids 50 to 146, an amino acid sequence consisting of amino acids 1 to 78, an amino acid sequence consisting of amino acids 200 to 241, an amino acid sequence consisting of amino acids 172 to 241, an amino acid sequence consisting of amino acids 103 to 150, and an amino acid sequence consisting of amino acids 169 to 241 with respect to the amino acid sequence shown in SEQ ID NO: 2. Further, a protein having an amino acid sequence comprising a deletion, substitution, addition or insertion of one or several amino acids with respect to any one of the above amino acid sequences; or a protein having an amino acid sequence having at least 70%, preferably 80% or more, more preferably 85% or more, further preferably 90% or more, and further more preferably 95% or more, and most preferably 98% or more homology with any one of the above nucleotide sequences, is also included in the scope of the present invention.

The present inventors have determined the nucleotide sequence of a human-type antigen gene according to a method similar to the methods described above (refer to Example 5 described later). Accordingly, the present invention provides a gene having a nucleotide sequence shown in SEQ ID NO: 3 or nucleotide sequence having homology therewith. Moreover, the present invention provides a protein having an amino acid sequence shown in SEQ ID NO: 4 or protein having homology therewith. As described in the section "Gene of the present invention" or "Protein of the present invention" of the present specification, the meaning of homology used herein, that is, the scope of the present invention, is not limited to the gene having the nucleotide sequence shown in SEQ ID NO: 3 or the protein having the amino acid sequence shown in SEQ ID NO: 4.

<Antibody of the Present Invention>

The present invention provides an antibody against the above described protein of the present invention (hereinafter referred to also as "the monoclonal antibody of the present invention.") Embodiments and methods of obtaining the antibody of the present invention will be explained in detail below.

The antibody of the present invention may be a polyclonal antibody or monoclonal antibody. In the case of a monoclonal antibody, it may be a chimeric antibody, and a mouse/human chimeric antibody is particularly preferable. The "monoclonal antibody" includes monoclonal antibodies belonging to any immunoglobulin class such as IgG, IgM, IgA, IgD and IgE, and it is preferably an IgG or IgM immunoglobulin class monoclonal antibody.

The protein of the present invention, which is used as an antigen, can be obtained by integrating a gene encoding the protein into a suitable expression vector and then transfecting the vector into a suitable host so that a recombinant protein is allowed to be expressed therein. Examples of an immunogen used include a macrophage cell line itself and the membrane fraction of the macrophage cell line.

The antibody of the present invention such as a polyclonal antibody (antiserum) or monoclonal antibody can be obtained by conventional methods (e.g. a method described in the publication "Zoku Seikagaku Jikken Koza 5, Meneki Seikagaku Kenkyu Ho, edited by The Japanese Biochemical Society, published by Tokyo Kagaku Dojin Co. Ltd.)

That is to say, for example, a mammal that is preferably mouse, rat, hamster, guinea pig, rabbit, dog, cat, pig, goat, horse or cow, and more preferably mouse, rat, hamster, guinea pig or rabbit, is immunized with an antigen together with Freund's adjuvant if necessary. A polyclonal antibody can be obtained from serum obtained from the thus immunized mammal. A monoclonal antibody can be produced by preparing a hybridoma from an antibody producing cell obtained from the immunized mammal and a myeloma cell (myeloma) having no ability to produce an autoantibody, cloning the hybridoma, and selecting a clone producing a monoclonal antibody which has specific affinity toward the antigen used for immunizing the mammal.

Specifically, the monoclonal antibody can be produced as follows. That is, the protein of the present invention or a cell expressing the protein of the present invention or the like are used as an immunogen, mouse, rat, hamster, guinea pig or rabbit, or preferably mouse, rat or hamster (these animals also include transgenic animals such as a human antibody producing transgenic mouse, which are produced to generate antibodies derived from other animals) is immunized with the above immunogen by injecting the immunogen together with Freund's adjuvant as necessary into the subcutis, muscle, vein, footpad or peritoneal cavity of the above mammal one to several times, or by transplanting it therein for immunization. Generally, after the initial immunization, the subsequent immunizations are carried out one to four times every one to fourteen days, and about one to five days after the final immunization, an antibody producing cell is obtained from the immunized mammal.

The monoclonal antibody of the present invention can be produced from a hybridoma (hybrid cell), which is produced by what is called cell fusion.

Hybridoma producing the monoclonal antibody can be prepared by known methods. Examples of the known methods include Köhler and Milstein's method (Nature, Vol. 256, pp. 495-497. 1975) and other modified methods equivalent thereto. That is, the monoclonal antibody of the present invention can be prepared by culturing the hybrid cell (hybridoma), which is obtained by fusion between an antibody producing cell contained in the spleen, lymph node, bone marrow or tonsilla, preferably the spleen obtained from the animal immunized as above, and a myeloma cell (myeloma) derived preferably from the same kind of mammal such as mouse, rat, guinea pig, hamster, rabbit or human, and more preferably from mouse, rat or human.

Examples of the myeloma cell (myeloma) used in cell fusion include myelomas "P3/X63-AG8", "P3/NS1/1-Ag4-1", "P3/X63-Ag8.U1", "SP2/0-Ag14", "X63, 653", "PAI", "FO" and "BW5147", which are derived from mouse, a myeloma "210RCY3-Ag1.2.3", which is derived from rat, and myelomas "U-266AR1", "GM1500-6TG-A1-2". "UC729-6", "CEM-AGR", "D1R11" and "CEM-T15" which are derived from human.

Screening of a hybrid cell clone producing the monoclonal antibody of the present invention can be carried out by culturing a hybrid cell, for example, in a microtiter plate, and determining the reactivity with an antigen of the culture supernatant in a well where proliferation of the cell is observed, for example, by flow cytometry, RIA, ELISA or the like.

Production of the monoclonal antibody from hybridoma is carried out in vitro, or in vivo, for example, in the ascites of mouse, rat, guinea pig, hamster or rabbit, preferably of mouse or rat, and more preferably of mouse, and the monoclonal antibody can be then isolated from the culture supernatant or the ascites of mammals. In the case of in vitro culture, hybridoma is proliferated, maintained and preserved, depending on various conditions such as the properties of cells to be cultured, the purpose of the test and the culture method, and the culture can be carried out, using a known nutrient medium used to allow accumulation of the monoclonal antibody in the culture supernatant or any type of nutrient medium prepared from known basal media.

Examples of the basal medium include a low-calcium medium such as Ham's F12 medium, MCDB153 medium or a low-calcium MEM medium; high-calcium medium such as MCDB104 medium, MEM medium, D-MEM medium, RPMI1640 medium, ASF104 medium or RD medium; and others. Depending on purposes, to the above basal medium, sera, hormones, cytokines, and/or various inorganic or organic substances can be added. Isolation and purification of the monoclonal antibody can be carried out by subjecting the above described culture supernatant or ascites to ammonium sulfate precipitation, euglobulin precipitation, caproic acid method, caprylic acid method, ion exchange chromatography (DEAE, DE52 or the like), affinity column chromatography which uses an anti-immunoglobulin column or a protein A or G column, hydrophobic chromatography, and others.

The "chimeric antibody" of the present invention is a monoclonal antibody produced by genetic engineering, and it specifically means a chimeric monoclonal antibody such as a mouse/human chimeric monoclonal antibody, which is characterized by that its variable region is derived from mouse immunoglobulin and its constant region is derived from human immunoglobulin. The constant region derived from a human immunoglobulin has a specific amino acid sequence, depending on isotypes such as IgG, IgM, IgA, IgD and IgE. The recombinant chimeric monoclonal antibody of the present invention may comprise a constant region derived from a human immunoglobulin, which belongs to any of the isotypes. Preferably, it is a constant region derived from human IgG. The chimeric monoclonal antibody of the present invention can be produced, for example, as follows: However, needless to say, the production method is not limited to the following.

For example, a mouse/human chimeric monoclonal antibody can be produced, referring to Jikken Igaku (extra edition), Vol. 1.6, No. 10, 1988 and Japanese Patent Publication No. Hei3-73280, etc. That is to say, a $C_H$ gene (a gene encoding an H chain constant region) obtained from DNA encoding human immunoglobulin is placed downstream of an active $V_H$ gene (a rearranged VDJ gene encoding an H chain variable region) obtained from DNA encoding a mouse monoclonal antibody isolated from hybridoma producing the monoclonal antibody so that the gene can be expressed, and further, a $C_L$ gene (a gene encoding an L chain constant region) obtained from DNA encoding human immunoglobulin is placed downstream of an active $V_L$ gene (a rearranged VJ gene encoding an L chain variable region) obtained from DNA encoding a mouse monoclonal antibody isolated from the above hybridoma so that the gene can be expressed. Thereafter, these genes are then inserted into a single or two separate expression vectors, a host cell is transformed by the vector(s), and the obtained transformed cell is cultured so as to produce the mouse/human chimeric monoclonal antibody.

Specifically, first, DNA is extracted from a mouse monoclonal antibody producing hybridoma by a conventional method, and the purified DNA is then digested with suitable restriction enzymes (e.g. EcoRI, HindIII and others). Thereafter, the digested DNA is subjected to electrophoresis (e.g. using 0.7% agarose gel) and Southern blotting. After subjecting the gel to electrophoresis, the gel is stained with e.g. ethidium bromide. A photograph of the gel is taken, then a position of a marker is marked. Then the gel is washed twice with water, and immersed in a 0.25 M HCl solution for 15 minutes. Subsequently, the gel is immersed in a 0.4 N NaOH solution for 10 minutes while gently shaking. According to a conventional method, the gel is transferred to a filter, and after 4 hours, the filter is collected and washed with 2×SSC twice. After the filter is fully dried, baking (75° C., 3 hours) is carried out. After baking, the filter is immersed in a 0.1×SSC/0.1% SDS solution and treated at 65° C. for 30 minutes. Thereafter, the filter is immersed in a 3×SSC/0.1% SDS solution. The thus treated filter is placed in a plastic bag with a prehybridization solution. The mixture is treated at 65° C. for 3 to 4 hours.

Thereafter, $^{32}$P labeled probe DNA and a hybridization solution are placed in the plastic bag, and the mixture is reacted at 65° C. for about 12 hours. After completion of the hybridization, the filter is washed under conditions of a suitable salt concentration, reaction temperature and reaction time (e.g. 2×SSC, 0.1% SDS solution, room temperature, 10 minutes). The filter is placed in a plastic bag and a small amount of 2×SSC is added thereto. The plastic bag is hermetically sealed and autoradiography is carried out. The rearranged VDJ and VJ genes, which respectively encode the H chain and L chain of the mouse monoclonal antibody, are identified by the above described Southern blotting. A region comprising the DNA fragment identified by this method is fractionated by cesium chloride density-gradient centrifugation, and the obtained fraction is integrated into a phage vector (e.g. charon4A, charon28, λEMBL3, λEMBL4, etc.) Escherichia coli (e.g. LE392, NM539, etc.) is transformed with said phage vector so as to prepare a genome library. Using a suitable probe (e.g. an H chain J gene, an L chain (κ) J gene, etc.), according to, for example, Benton-Davis method (Science, Vol. 196. pages 180 to 182, (1977)), plaque hybridization is carried out on the genome library so as to obtain a positive clone comprising each of the arranged VDJ and VJ genes. The restriction enzyme map of the obtained clone is prepared, the nucleotide sequence is determined to confirm whether a gene of interest comprising a rearranged $V_H$ (VDJ) gene or $V_L$ (VJ) gene can be obtained.

On the other hand, a human $C_H$ gene and a human $C_L$ gene used in chimerization are isolated separately. For example, in the case of producing a chimeric antibody with human IgG1, a Cγ1 gene as a $C_H$ gene and a Cκ gene as a $C_L$ gene are isolated. Since a mouse immunoglobulin gene has high homology with a human immunoglobulin gene, the above two genes can be obtained by isolating from a human genome library, using, as probes, a mouse Cγ1 gene and a mouse Cκ1 gene which respectively correspond to a human Cγ1 gene and a human Cκ gene.

Specifically, for example, using a 3 kb of HindIII-BamHI fragment from a clone Ig146 (Proc. Natl. Acad. Sci. USA, Vol. 75, pages 4,709 to 4,713 (1978)) and a 6.8 kb of EcoRI fragment from a clone MEP10 (Proc. Natl. Acad. Sci. USA, Vol. 78, pages 474 to 478 (1981)) as probes, a DNA fragment comprising the human κ gene with an enhancer region is isolated from the HaeIII-AluI genomic library of a human λCharon4A (Cell, Vol. 15, pages 1,157 to 1,174 (1978)). In the case of the human Cγ1 gene, for example, human fetal liver cell DNA is cleaved with HindIII, and fractionated by agarose gel electrophoresis. Thereafter, 5.9 kb of the obtained band is inserted into λ788 followed by isolation with the above probes.

Using the thus obtained mouse $V_H$ gene and mouse $V_L$ gene, as well as human $C_H$ gene and human $C_L$ gene, taking a promoter region and an enhancer region into consideration, the human $C_H$ gene is placed downstream of the mouse $V_H$ gene and the human $C_L$ gene is placed downstream of mouse $V_L$ gene; and these genes are then integrated into an expression vector(s) such as pSV2gpt or pSV2neo, using suitable restriction enzymes and DNA ligase according to conventional methods. Herein, a chimeric gene of mouse $V_H$ gene/human $C_H$ gene and a chimeric gene of mouse $V_L$ gene/human $C_L$ gene may be simultaneously integrated into a single expression vector, or may be integrated into two separate expression vectors.

The thus produced expression vector, into which the chimeric gene is inserted, is introduced into a myeloma cell such as P3X63.Ag8.653 cell or SP2/0 cell, which does not produce an antibody by itself, by spheroplast fusion. DEAE-dextran method, calcium phosphate method, electroporation or the others. The obtained cells are cultured in a medium which contains an agent for an agent-resistant gene introduced in the expression vector so as to select a transformed cell, thereby obtaining a chimeric monoclonal antibody producing cells of interest. Then, a chimeric monoclonal antibody of interest is obtained from the culture supernatant of the thus selected antibody producing cell.

The "humanized antibody (CDR-grafted antibody)" of the present invention is a monoclonal antibody produced by genetic engineering, and it specifically means a humanized antibody characterized in that a part or the entire CDRs of the hypervariable region is derived from a mouse monoclonal antibody, the framework region in the variable region is derived from human immunoglobulin, and the constant region is a human immunoglobulin region.

Herein, the CDRs of the hypervariable region means three regions (CDR1, CDR2 and CDR3) which exist in the hypervariable region of the variable region of an antibody and complementarily bind to an antigen, and the framework region (FR) in the variable region means four regions (FR1, FR2, FR3 and FR4) which are located before and after the above three CDRs and are relatively well conserved. In other words, it is a mouse monoclonal antibody, in which all the regions other than a part or the entire CDR of the hypervariable region are substituted by the corresponding human immunoglobulin regions. The constant region derived from the corresponding human immunoglobulin region has a specific amino acid sequence depending on isotypes such as IgG, IgM, IgA, IgD and IgE. However, the constant region of humanized antibody of the present invention may be the constant region of human immunoglobulin which belongs to any type of the isotypes. Preferably, it is the constant region of human IgG. Moreover, there is not a limit as to the FR in the variable region derived from human immunoglobulin.

The humanized antibody of the present invention can be produced, for example, as follows. However, needless to say, the production method is not limited to the followings: For example, a recombinant humanized antibody derived from a mouse monoclonal antibody can be produced by genetic engineering, referring to Domestic Announcement No. Hei4-506458, Japanese Patent Laid-Open No. Sho62-296890, and others. The production of a humanized antibody involves, first, selecting human $V_H$ and $V_L$ having high homology with the amino acid sequence in the V region of a monoclonal antibody of interest: searching for and selecting the amino acid residues in FR region having an effect on the higher-order structure of CDR by computer modeling, and designing all amino acid sequences in $V_H$ and $V_L$ regions which consist of mouse-derived CDR (including a small amount of FR sequence) and a human-derived PR region sequence. As a C region, the desired class or sub-class of a human antibody is selected. The $V_H$ and $V_L$ genes are produced by chemical synthesis, PCR or site-directed mutagenesis. Taking a promoter region and an enhancer region into consideration, the V region genes of the H chain and L chain of the thus designed mouse antibody are ligated to the C region genes of the H chain and L chain of a human antibody, respectively. The obtained genes are integrated into expression vectors separately, and the vectors are then introduced into cells for expression. As an expression vector, such as pSV2gpt or pSB2neo, is often used. Expression may also be carried out using a single vector. Subsequently, the expression vector is then introduced into a cell line, such as mouse myeloma Sp2/0, which does not produce expression and secretion of immunoglobulin. The Antibody may be generated not only in a myeloma but also in animal cells. insect cells, yeast or *Escherichia coli*.

The "human antibody" of the present invention is immunoglobulin, in which all the constructed regions including the variable and constant regions of the H chain as well as the variable and constant regions of the L chain are derived from a gene encoding human immunoglobulin. By the same method as described above for the production of a polyclonal or monoclonal antibody, the human antibody can be produced by the antigenic or immunogenic stimulation of a transgenic animal, which is produced by integrating, for example, at least a human immunoglobulin gene into the gene locus of mammals other than human such as mouse according to conventional methods. For example, a transgenic mouse which produces a human antibody can be produced by methods described in Nature Genetics, Vol. 7, pages 13 to 21, 1994; Domestic Announcement No. 4-504365; International Publication WO94/25585; Nikkei Science, June, pages 40 to 50, 1995: Nature, Vol. 368, pages 856 to 859, 1994: and Domestic Announcement No. Hei6-500233.

The term "portion of an antibody" or "fragment of an antibody" is used herein to mean an antibody fragment comprising at least one variable region, and means a partial region of the above described antibody, preferably the monoclonal antibody of the present invention. Specifically, it refers to Fv, F(ab')$_2$, Fab' or Fab. Each of the terms "F(ab')$_2$" and "Fab'" is used herein to mean an antibody fragment obtained by treating immunoglobulin (monoclonal antibody) with protease such as pepsin or papain and digesting before or after a disulfide bond existing between two H chains in a hinge region. For example, when IgG is treated with papain, it is cleaved upstream of the disulfide bonds between the two H chains in the hinge region, thereby producing two homologous antibody fragments in which an L chain fragment consisting of VL (an L chain variable region) and CL (an L chain constant region) and an H chain fragment consisting of VH (an H chain variable region) and CHγ1 (a γ1 region in an H chain constant region) are bound in a C-terminal region by a disulfide bond. Each of the two identical antibody fragments is called Fab'. When IgG is treated with pepsin, it is cleaved downstream of the disulfide bonds between the two H chains in the hinge region, thereby producing an antibody fragment which is slightly larger than the above described two Fab's which are bound each other in the hinge region. This antibody fragment is called F(ab')$_2$.

<Recombinant Vector and Transformant>

The present invention further provides a recombinant vector comprising the gene of the present invention or the DNA fragment thereof.

The recombinant vector can be simply produced by ligating a desired gene to a vector for cloning (e.g. plasmid DNA, etc.) available in the present field of the art according to conventional methods. Examples of the vector used include a plasmid derived from *Escherichia coli* such as pBluescript, pUC18, pUC19 or pBR322, but are not limited thereto.

For the purpose of producing a desired protein, an expression vector is particularly useful. The type of the expression vector is not particularly limited, as long as it has functions to express a desired gene in various types of host cells such as procaryotic cells and/or eucaryotic cells so as to produce a desired protein. Examples of a preferred expression vector include expression vectors for *Escherichia coli* such as pQE-30, pQE-60, pMAL-C2, pMAL-p2 and pSE420, expression vectors for yeast such as pYES2 (Saccharomyces), pPIC3.5K, pPIC9K and pAO815 (supra; genus *pichia*), and expression vectors for insects such as pBacPAK8/9, pBK283, pVL1392 and pBlueBac4.5.

Examples of a method of inserting a DNA fragment of the gene of the present invention into a vector such as a plasmid include a method described in Sambrook, J. et al., Molecular Cloning, A Laboratory Manual, (second edition), Cold Spring Harbor Laboratory, 1.53 (1989) and the like. Simply, a commercially available ligation kit (e.g. Takara Shuzo Co., Ltd.) can be used. The thus obtained recombinant vector (e.g. a recombinant plasmid) can be introduced into a host cell according to a method as described below.

The recombinant vector of the present invention can be introduced (transformed or transfected) into a host cell according to previously known methods. Examples of such a method include calcium chloride method described in Sambrook, J. et al., Molecular Cloning, A Laboratory Manual. (second edition), Cold Spring Harbor Laboratory, 1.74 (1989), calcium chloride/rubidium chloride method electroporation, electroinjection, a chemical treatment method such as PEG, a method of using gene gun and others. Otherwise, in a case where the host cell is bacterium (*E. coli, Bacillus subtilis*, etc.), methods such as Cohen et al.'s method (Proc. Natl. Acad. Sci. USA, 69, 2110 (1972)), protoplast method (Mol. Gen. Genet., 168, 111 (1979)) or competent method (J. Mol. Biol., 56, 209 (1971)) can be applied to introduce a recombinant vector into the host cell. In a case where the host cell is *Saccharomyces cerevisiae*, methods such as Hinnen et al.'s method (Proc. Natl. Acad. Sci. USA, 75, 1927 (1978)) or lithium method (J. Bacteriol., 153, 163 (1983)) can be applied, and in a case where the host cell is a plant cell, methods such as leaf disk method (Science, 227, 129 (1985)) or electroporation (Nature, 319, 791 (1986)) can be applied. In the case of an animal cell, methods such as Graham's method (Virology, 52, 456 (1973)) can be applied, and in the case of an insect cell, methods such as Summers et al.'s method (Mol. Cell. Biol., 3, 2156-2165 (1983)) can be applied.

A host cell used to produce a tranformant is not particularly limited, as long as it is suitable for the recombinant vector of the present invention and can be transformed, and various cells such as native cells commonly used in the technical field of the present invention or artificially established recombinant cells can be used. Examples of the host cell used include procaryotic cells such as bacteria (*Escherichia, Bacillus*, etc.); lower eucaryotic cells including a unicellular host such as yeast (*Saccharomyces*, genus *pichia*, etc.): higher eucaryotic cells such as silk worm; and others. Examples of a preferred host cell include *Escherichia coli*, yeast, an insect cell and others. Specific examples of such a host cell include *Escherichia coli* (M15, JM109, BL21, etc.), yeast (INVScl (*Saccharomyces*), GS115 and KM71 (supra; genus *pichia*), etc.), insect cells (BmN4, silk worm larva, etc.), and others. Examples of an animal cell include a mouse-derived, Xenopus-derived, rat-derived, hamster-derived, monkey-derived or human-derived cell, a culture cell line established from these cells, and others.

When bacteria, especially *Escherichia coli*, is used as a host cell, the corresponding expression vector is generally comprised of at least a promoter/operator region, an initiation codon, a gene encoding a desired protein, a termination codon, a terminator and a replicable unit. When yeast, a plant cell, animal cell or insect cell is used as a host cell, generally, the corresponding expression vector preferably comprises at least a promoter, an initiation codon, a gene encoding a desired protein, a termination codon and a terminator. Moreover, a host cell may also comprise DNA encoding a signal peptide, an enhancer sequence, the non-translation regions of the 5'-side and 3'-side of a desired gene, a selective marker region, a replicable unit and others, as appropriate.

An example of a preferred initiation codon for the vector of the present invention includes a methionine codon (ATG). An example of a termination codon includes a commonly used termination codon (e.g. TAG, TGA, TAA. etc.) The replicable unit means DNA capable of replicating all the DNA sequences thereof in a host cell, and examples include a native plasmid, an artificially modified plasmid (which is pr pared from a native plasmid), a synthetic plasmid and others. Examples of a preferred plasmid include a plasmid pQE30, pET, pCAL or an artificially modified product of these plasmid (i.e. a DNA fragment obtained by treating pQE30, pET or pCAL with suitable restriction enzymes) for *Escherichia coli*; a plasmid pYES2 or pPIC9K for yeast; and a plasmid pBacPAK8/9 or the others for an insect cell.

As an enhancer sequence and a terminator sequence, products such as one derived from SV40, which are commonly used by a person skilled in the art, can be used. As a selective marker, commonly used products can be used according-to conventional methods. Examples of such a selective marker include resistance genes to antibiotics such as tetracycline, ampicillin, kanamycin, neomycin, hygromycin, spectinomycin or chloramphenicol.

An expression vector can be prepared by continuously and circularly ligating at least the above promoter, initiation codon, gene encoding a desired protein termination codon and terminator region to a suitable replicable unit. This time, a suitable DNA fragment (e.g. a linker, another restriction site, etc.) can also be added, as desired, by applying conventional methods such as digestion with restriction enzymes or ligation-with T4DNA ligase.

<Receptor, Screening Method>

It is considered that the protein encoded by the gene of the present invention acts as an entrance to induce or stimulate the secretion of G-CSF (that is, as a possibility, a model can be speculated, in which an external ligand is bound to the protein of the present invention existing on the surface of a macrophage, a signal generated by the event is transmitted into the cell so that the macrophage releases G-CSF, but the present invention is not restricted to the above theory.) Accordingly, the protein of the present invention can be a receptor of a G-CSF secretion inducing or stimulating factor or a portion thereof. The term "a portion of a receptor" is used herein to include a receptor portion which is a part constituting the receptor modified with a sugar chain or the like. It is considered that this receptor has a binding ability (which is referred to also as affinities) for a substance capable of inducing the generation of G-CSF, such as a monoclonal antibody or a fragment thereof produced from hybridoma deposited under accession No. FERM BP-6103; and that the receptor exists in the cell membrane of a cell capable of generating G-CSF such as a macrophage. The present invention provides the above receptor.

The present invention further provides a method of screening a useful substance, which is characterized in that the protein or receptor of the present invention is used. The screening method of the present invention comprises the steps of (a) bringing a substance into contact with the protein according to any one of claims 9 to 12 or a cell comprising the receptor according to claim 20; and (b) determining the effect of the substance obtained through the contact with the protein or receptor. The present screening method further comprises the steps of determining the affinity of a substance in question (simply referred to as "a substance" or "a test compound" at times) for the protein of the present invention, the above described receptor, or a cell comprising the same (e.g. analysis of the affinity between a cell having the receptor of the present invention on a surface thereof and the substance in question using a flow cytometer); determining the effect of the substance in question obtained through the contact with the above receptor (e.g. the generation of G-CSF from a macrophage, the generation of a marker substance from a suitable transformed cell); or comparing the structure of the substance in question (e.g. when the substance in question is a protein, it is the amino acid sequence) with the structure of the protein of the present invention (e.g. the amino acid sequence).

Moreover, the screening method of the present invention includes means of designing a compound with a computer on the basis of the structural information of the protein or receptor of the present invention, synthesizing many types of the thus designed compounds and/or analogs thereof by a technique such as combinatorial chemistry, and selecting a useful substance from the synthesized compounds and/or analogs thereof using a suitable technique (e.g. HTS (high throughput screening, etc.); means of synthesizing and selecting more modified products, using such a substance as a lead compound; and others.

The protein or receptor of the present invention used in the screening is, preferably, (a) a protein having an amino acid sequence shown in SEQ ID NO: 4; (b) a protein having an amino acid sequence comprising a deletion, substitution, addition or insertion of one or several amino acids with respect to the amino acid sequence shown in SEQ ID NO: 4, and having a binding ability for an antibody capable of inducing and secreting a G-CSF or a fragment thereof: (c) a protein having 50% or more (preferably 60% or more, more preferably 70% or more, further preferably 80% or more, further more preferably 90% or more, particularly preferably 94% or more, and most preferably 98% or more) homology with the amino acid sequence shown in SEQ ID NO: 4, and having a binding ability for an antibody capable of inducing and secreting a G-CSF or a fragment thereof: (d) a protein being encoded by DNA which hybridizes with DNA having the nucleotide sequence shown in SEQ ID NO: 3 under stringent conditions, and having a binding ability for an antibody capable of inducing and secreting a G-CSF or a fragment thereof: or a receptor having any one of the above proteins.

A more specific example of the screening method is as follows: A vector into which a G-CSF promoter gene; a gene encoding a marker protein such as luciferase, β-galactosidase, a green fluorescence protein (GFP), β-lactamase or chloramphenicol acetyl transferase (CAT), which locates downstream of the above gene; and an agent resistance gene to agents such as tetracycline, ampicillin, kanamycin, neomycin, hygromycin or spectinomycin, which locates further downstream of the above gene, are inserted, is constructed. This vector is introduced into a cell having the receptor including the protein of the present invention (e.g. a macrophage cell line, preferably a human-derived macrophage cell line). The obtained cell is treated in a medium containing an agent to select a cell group which forms a colony. Thereafter, a clone expressing a marker protein is further selected using a G-CSF inducing agent such as lipopolysaccharide (LPS). Further, it is confirmed that the expression of the marker protein reflects the expression of G-CSF mRNA. The thus obtained transformed cell line is treated with various substances so that a substance inducing the expression of the marker protein is screened.

In the screening method of the present invention, a portion of the protein of the present invention, which is recognized by an antibody having induction or secretion promotion activity of G-CSF (e.g. a monoclonal antibody produced from hybridoma deposited under accession No. FERM BP-6103) or a fragment thereof, is particularly important in some cases. A method of determining such an important portion is well known to a person skilled in the art. For example, the present inventors have determined a portion recognized by a monoclonal antibody produced from hybridoma deposited under accession No. FERM BP-6103 in one protein of the present invention which has an amino acid sequence shown in SEQ ID NO: 2 (refer to Example 9).

<Novel Substance>

The useful substance obtained by screening is a substance capable of changing the production of G-CSF. This substance includes; (a) a substance having a binding ability to a receptor (it is predicted that, as a result of binding, the substance changes the receptor and transmits information into a cell through the receptor, and inducing the production of G-CSF (referred to also as an agonist or stimulant); (b) a substance having a binding ability to a receptor (It is predicted that, as a result of binding, the substance antagonizes the binding of a substance inducing the production of G-CSF to a receptor and inhibits the stimulation), and not inducing the production of G-CSF (referred to also as an antagonist or blocking agent); and (c) a substance having a binding ability to a receptor (it is predicted that as a result of the binding, the substance inhibits the binding of a substance inducing the production of G-CSF to a receptor), and inhibiting the activity of producing G-CSF-of a receptor itself (referred to also as an inverse agonist or counteragent).

This substance is novel. Therefore, the present invention provides: (a) a substance having a binding ability to a receptor (it is predicted that, as a result of binding, the substance changes the receptor and transmits information into a cell through the receptor), and inducing the production of G-CSF; (b) a substance having a binding ability for a receptor (it is predicted that, as a result of binding, the substance antagonizes the binding of a substance inducing the production of G-CSF to a receptor and inhibits the stimulation), and not inducing the production of G-CSF: or (c) a substance having a binding ability for a receptor (it is predicted that, as a result of the binding, the substance inhibits the binding of a substance inducing the production of G-CSF to a receptor) and inhibiting the activity of producing G-CSF of a receptor itself, wherein the above substance is obtained by the screening method of the present invention. Moreover, the present invention further provides a substance having a binding ability for the protein or receptor of the present invention, which is selected from a group consisting of: (a) a substance which induces the generation of G-CSF (it is predicted that, as a result of binding the substance changes the receptor and transmits information into a cell through the receptor); (b) a substance which does not induce the production of G-CSF (it is predicted that, as a result of binding, the substance antagonizes the binding of a substance inducing the production of G-CSF to a receptor and inhibits the stimulation): and (c) a substance which inhibits the activity of producing G-CSF of a receptor itself (it is predicted that, as a result of the binding, the substance inhibits the binding of a substance inducing the production of G-CSF to a receptor). Hereinafter, these substances may be called "the substance of the present invention" at times. The technical scope of the substance of the present invention does not include known substances.

Examples of the substance of the present invention include the antibody of the present invention; a fragment thereof; or other low molecular compounds, which induce the production of G-CSF, which antagonize the binding of a substance inducing the production of G-CSF to a receptor and inhibit the stimulation, or which inhibit the action to produce G-CSF of a receptor itself and also inhibit the production of G-CSF.

With regard to the above "other low molecular compounds," many types of low molecular compounds can be synthesized by means well known to a person skilled in the art such as combinatorial chemical synthesis, or an established chemically synthetic library can also be used (M. J. Plunket et al., Development of New Drugs and Combinatorial Chemistry: Nikkei Science 7, 62-69 (1997); Combinatorial Chemistry, edited by Japan Combinatorial Chemistry Focus Group, Kagaku Dojin Publishing Co., Inc. (1998)).

When a substance in question is an antibody, the affinity for (or inhibition of the binding to) the above receptor can be determined by analyzing a macrophage cell line binding to the antibody by flow cytometry or ELISA, or by equivalent methods.

An action to induce (or inhibit) the production of a G-CSF can be determined by a method described in Japanese Patent Laid-Open No. Hei11-106400. The outline of the method will be described below.

A G-CSF promoter gene is inserted into the restriction sites between XhoI and NcoI of a PicaGene Enhancer Vector 2 (Wako Pure Chemical Industries, Ltd.), a luciferage gene is ligated downstream of it-instead of the G-CSF gene, and further a neomycin-resistance gene cut from pMC1Neo Poly A is inserted into the SalI site which is located downstream of SV40, so that a PicaGCSFneo vector is produced. This vector is introduced in the RAW264.7 cell by electroporation. The obtained gene is treated with a medium containing geneticin, and cells forming a colony are selected. Thereafter, a clone showing luciferase activity is selected among the geneticin-resistant clones using a G-CSF inducing agent such as LSP. It is confirmed that the luciferase activity reflects the expression of G-CSF mRNA, by Northern blotting analysis, using $^{32}P$ labeled mouse G-CSF cDNA as a probe. The thus obtained transformed macrophage cell line is inoculated in an amount of $5\times10^4$ cells per well of a 96-well microplate followed by culture at 37° C. for 24 hours. Thereafter, the cells are treated with the previously obtained agonist or antagonist as necessary, and a substance in question is then added thereto in a concentration of 0, 3.75, 7.5, 15, 30 and/or 60 μg/ml. After culture at 37° C. for 18 hours, luciferase activity is determined.

Otherwise, the action to induce (or inhibit) the production of G-CSF can also be determined by bioassay for G-CSF, which is described in Example 14 hereafter.

Whether or not it is the substance of the present invention can be determined by various criteria. For example, (1) a system capable of producing G-CSF, or a system showing a parameter capable of reflecting the production of G-CSF is constructed, then, a group with the addition of a test compound and a suitable control group (e.g. a system using a known substance instead of the test compound, or a system using neither the test compound nor the alternative) are prepared, and determination can be made using the value obtained in the control group as a standard. Herein, a group comprising both the test compound and an agonist or antagonist, which has previously been obtained, may also be prepared. Moreover, (2) determination can also be made on the basis of the binding ability between the receptor or the protein of the present invention and the test compound (e.g. the affinity constant (referred to also as Km, association constant) between the receptor or protein and the test compound, which is determined by appropriate means). In this case, the value obtained using a known substance instead of the test compound can be used as a standard. Otherwise, (3) determination can also be made by combination of (1) and (2).

More specifically, when a cell having the protein of the present invention on a surface thereof and is transformed so that the luciferase activity can reflect the actual expression of G-CSF mRNA is stimulated with a test compound, and the maximum luciferase activity obtained under appropriate conditions is higher than the control group, preferably it is about 1.01-fold or more, more preferably it is about 2-fold or more, further preferably about 20-fold or more, and most preferably about 60-fold or more, the test compound can be defined as "a substance having a binding ability for the protein or receptor of the present invention, and (a) inducing the production of G-CSF" in the present invention (see Examples). Moreover, a system which comprises a group allowing the previously obtained agonist or antagonist to co-exist with the test compound can be used to determine whether or not it is "a substance having a binding ability for the protein or receptor of the present invention, and (b) not inducing the production of G-CSF: or (c) inducing the production of G-CSF" in the present invention.

The substance of the present invention may also induce cytokines other than G-CSF such as interleukin (IL), interferon (INF), tumor necrosis factor (TNF) or various colony-stimulating factors (CSFs). A substance inducing G-CSF more selectively than other cytokines is one preferred embodiment of the substance of the present invention. An example of such a substance includes a substance, which induces other cytokines at a level of less than about 10-fold of the control, but induces G-CSF cytokine at a level of about 10-fold or more, preferably about 20-fold or more, and more preferably about 40-fold or more of the control, when it is used in an appropriate concentration. The induction of other cytokines can be determined by a method well known to a person skilled in the art.

<Use of the Gene and others of the Present Invention as a Pharmaceutical>

The gene of the present invention can be used for diagnosis, prevention and treatment (e.g. gene therapy, etc.) of diseases with which one type of the leukocytes, neutrophils, is associated (e.g. neutropenia, etc.), or diseases relating to blood cells such as erythrocyte, leukocyte or thrombocyte. Moreover, the inventive protein or a partial peptide thereof, antibody or a fragment thereof, ligand, receptor, or substance (hereinafter, these may be generically referred to as "the protein and others of the present invention") can be used as a pharmaceutical which controls the number of neutrophils in the blood or bone marrows, or more widely, controls the number of blood cells such as erythrocytes, leukocytes or thrombocytes. That is to say, the gene, protein and others of the present invention can be used for the treatment of neutropenia as a side effect of an anticancer agent or neutropenia occurring after operation of bone marrow transplantation, or cytopenia regarding the reduction of the number of erythrocytes, leukocytes, thrombocytes and others, and the diagnosis, prevention and treatment of aplastic anemia.

Moreover, the present inventors have found that the protein or receptor of the present invention is associated with the induction of the production of G-CSF. Accordingly, a substance having a binding ability to the protein or receptor of the present invention can be used as a pharmaceutical promoting the production of G-CSF or controlling biological activity regarding G-CSF. This substance can be used especially for the treatment of neutropenia as a side effect of an anticancer agent, neutropenia occurring after operation of bone marrow transplantation, the cytopenia regarding the reduction of the number of erythrocytes, leukocytes, thrombocytes and others, or neutropenia occurring after bone marrow transplantation, and the diagnosis, prevention and the treatment of aplastic anemia.

Usually, the protein and others of the present invention can be administered systemically or locally, generally in a parenteral form. Of parenteral administrations, an intravenous administration is particularly preferable.

The gene of the present invention can be administered systemically or locally by what is called gene therapy in which a gene is introduced into a cell in vivo or in vitro. The gene transfer can be carried out by, for example, the method described in Blomanual UP Series, Basic Techniques of Gene Therapy, edited by Takashi Shimada, Izumi Saito and Takaya Ozawa, published by Yodosha Co., Ltd., 1996. When a gene is introduced into a cell in vitro, methods of using a retrovirus vector, an adenovirus vector, an adeno-associated virus (AAV) vector, cationic liposome or HVJ liposome; calcium phosphate method; DEAE dextran method; and others can be used. When a gene is introduced into a cell An vivo, methods of using a retrovirus vector, an adenovirus vector, an adeno-associated virus (AAV) vector, cationic liposome or HVJ liposome can be used.

Dosage is different depending on age, sex, body weight, symptom conditions, treatment effect, administration route, treatment time or an agent to be administered (the type of a protein or gene), but the agent can be administered in a range of 1 μg to 100 g, preferably 10 μg to 1000 mg per adult per time, one to several times per day by parenteral administration. Since the dosage is changed by various conditions, in some cases, an amount smaller than the above range of dosage may be sufficient, but in other cases, a dosage over the above range may be required. Examples of injections for parenteral administration of the present invention include aseptic aqueous or non-aqueous solution, suspension, emulsion and others. The aqueous or non-aqueous solution or suspension is obtained by mixing one or more active substances with at least one inactive diluent. Examples of the aqueous diluent include distilled water for injection, physiological salt solution and others. Examples of the non-aqueous diluent include propylene glycol, polyethylene glycol, vegetable oil such as olive oil, alcohols such as ethanol, and others.

This composition may also comprise an adjuvant, such as an antiseptic, wetting agent, emulsifier, dispersing agent or stabilizer (e.g. arginine, aspartic acid, etc.)

The injections are sterilized by filtration through a bacteria retaining filter, with mixing of germicide, or irradiation. Moreover, it is also possible to produce an aseptic solid composition, for example, by freeze-drying, and dissolve it in aseptic distilled water for injection or other solvents b fore use.

Examples of other compositions for parenteral administration include a liquid for external use prescribed by conventional methods, suppository and pessary for enteric administration, and others, which comprise one or more active substances.

The present invention is further described in the following examples. The examples are provided for illustrative purposes only, and are not intended to limit the scope of the invention.

EXAMPLES

Example 1

Production and Purification of 3-4H7 Antibody (Produced from Hybridoma Deposited Under Accession No. FERM BP-6103; Described in Japanese Patent Application No. 9-266591 Specification All the steps of the production and purification of 3-4H7 (IgM), a signaling antibody (agonist antibody), were carried out by aseptic manipulation to prevent contamination of microorganisms and endotoxin, such as lipopolysaccharide (LPS). Moreover, the treatment was carried out, while always measuring the endotoxin concentration of the culture solution and reagent used (described later) and checking that the concentration was within the tolerance (0.1 or less EU/ml). That is, in an Integra CL1000 culture flask, hybridoma cells were suspended in an ASF104 serum free medium at a density of $1\times10^8$ cells per ml, and culture was carried out for 5 days. The obtained supernatant was diluted with a 3-fold amount of 10 mM phosphate buffer (pH 6.8) containing 200 mM NaCl. It was loaded on an MGPP column which was previously equilibrated, and washed with a 10 mM phosphate buffer (Ph 6.8) containing 200 mM NaCl to eliminate contaminants. An antibody was eluted with a 300 mM phosphate buffer (pH 6.8), and the obtained antibody was dialyzed in a phosphate buffered saline (PBS, pH 7.4) to obtain an antibody solution. The purity of the purified antibody was determined by FPLC and SDS-PAGE, and then the antibody was subjected to the following experiment.

Example 2

Quantitation Assay for LPS Concentration

The concentration of LPS contaminated in the solutions used in the experiment was assayed by Limulus method using an Endospecy Toxicolor System (Seikagaku Kougyo Corporation). That is to say, 50 µl of the solutions were placed on an endotoxin free 96-well microplate, 50 µl of a lysate-synthetic reaction substrate solution was added thereto on ice, immediately followed by reaction at 37° C. for 30 minutes. Immediately after that, 50 µl each of a sodium nitrite solution, ammonium sulfamate solution, N-(1-naphtyl)ethylenediamine dihydrochloride-N-methyl-2-pyrrolidone solution were added thereto in this order, and then absorption at 550 nm was measured using Microplate Reader M-Tmax (Molecular Device Corp.). By subtracting the absorption value at 650 nm, a control value, LPS concentration was calculated by SoftMax 1.5 program. A USP standard product was used as standard concentrations of LPS, and the same LPS was used when cells were stimulated.

Example 3

Cloning of Antigen Gene Against 3-4H7 Antibody in the Macrophage Cell Lines (1) Preparation of Poly A$^+$ RNA From the Macrophage Culture Cell Line, RAW264.7

Approximately 0.3 mg of a total RNA was prepared from the RAW264.7 cells ($2\times10^8$ cells) by guanidium thiocyanate/phenol chloroform single step extraction (Labobanual Gene Engineering, $3^{rd}$ edition, 83-84, 1996). The obtained total RNA was further purified using an oligo(dT) cellulose column (Life Technologies) to obtain approximately 5 µg of poly A$^+$ RNA.

(2) Construction of cDNA Library

The synthesis of cDNA was carried out by linker-primer method (modification of Gubler-Hoffmann method: Gene, 25:263-269, 1983), using a ZAP-cDNA synthesis kit from STRATAGENE. That is, a linker-primer (2.8 µg) containing olido(dT)$_{18}$ and a XhoI recognition sequence and reverse transcriptase (MMLV-RTase; 70 units) were added to the poly A$^+$ RNA (5 µg) obtained in (1) as described above which was followed by reaction at 37° C. for 60 minutes to synthesize complementary single stranded DNA (ss-cDNA). At the time, 5-methyl dCTP was taken therein so as to protect cDNA from the subsequent restriction enzyme treatment. Thereafter, RNase H (2 units) was acted thereon, so that a nick was generated on a DNA-RNA hybrid. Using the generated RNA fragment as a primer, E. Coli DNA polymerase I (100 units) was added thereto followed by reaction at 16° C. for 150 minutes to synthesize ds (double stranded)-cDNA (8 µg). After carrying out phenol/chloroform extraction and ethanol precipitation, the thus prepared ds-cDNA was reacted at 72° C. for 30 minutes in a reaction solution comprising pfu DNA polymerase (5 units) for blunt-ending.

Phenol/chloroform extraction and ethanol precipitation were carried out again, an ScoRI adaptor (0.35 µg) which was previously annealed in a buffer containing T4 DNA ligase (4 units) was added thereto by reacting at 8° C. overnight, and then the EcoRI side of the cDNA was phosphorylated by reacting with T4 polynucleotidekinase (10 units) at 37° C. for 30 minutes. Thereafter, the linker-primer portion was cleaved by reaction with XnoI (120 units) at 37° C. for 90 minutes, the obtained cDNA was fractionated by size using a spin column, and it was confirmed by 1% agarose gel electrophoresis that the length of the DNA strand was 0.5 kbp or longer. Thereafter, the DNA was reacted in a buffer containing T4 DNA ligase (4 units) at 12° C. overnight so that it was inserted into a λZAP II vector (1 µg). The ligated λDNA was incubated at room temperature for 90 minutes using a Gigapack III Gold packaging extract from STRATAGENE for in vitro packaging, it was then used to infect Escherichia coli XL1-Blue MRF', then a plaque was formed on a plate at 37° C. for 8 hours in the presence of IPTG (isopropyl-β-D-thiogalactopyranoside; 2.5 HM) and X-Gal (4 mg/ml), and then titration was carried out. As a result, it was found that this cDNA library comprised $1.2 \times 10^6$ original clones. The cDNA library was amplified with *Escherichia coli* XL1-Blue MRF' to a size of $3.4 \times 10^9$ pfu, and then used in the following screening.

(3) Screening of Genes Encoding Protein Having Affinity for 3-4H7 Antibody

In the cDNA library constructed in (2) above, cDNA is introduced in the 3' side of the structural gene of β-galactosidase controlled by a lac promoter. Accordingly, the cDNA is expressed as a fusion protein with β-galactosidase. Thus, this fusion protein was blotted on the membrane, and immunoscreening was carried out using the 3-4H7 antibody as a probe for expression cloning by *Escherichia coli*. That is to say, $3.5 \times 10^4$ pfu each of phages were mixed with top agarose, and the mixture was inoculated on a plate with a diameter of 150 mm so as to prepare 20 plates in total. These plates were incubated at 42° C. for 4 hours so as to form a plaque with a diameter of approximately 0.5 mm, a nitrocellulose membrane in which sterile IPTG was previously immersed was placed on the plaque, and incubation was carried out at 37° C. for 3 hours to induce the expression. Thereafter, the membrane was removed, and blocking was carried out for 1 hour in a TBS-T solution (0.1% Tween 20, 20 mM Tris buffer physiological salt solution, pH 7.6) containing 5% skim milk. Thereafter, the membrane was washed with TBS-T, and the 3-4H7 antibody (1.6 μg/ml-1% BSA-TBS) as the first antibody was reacted therewith for 1 hour. After washing, alkaline phosphatase labeled antimouse IgM rabbit antibody (Zymed, 0.6 μg/ml) as the second antibody was reacted therewith for 1 hour. After the washing well again, incubation was carried out in a substrate solution (500 μg/ml NBT (nitroblue tetrazolium) containing 5 mM $MgCl_2$, 500 μg/ml BCIP(5-bromo-4-chloro-3-indolyl phosphate) TBS'solution, pH 9.5) in dark for 30 minutes so as to develop color. The filter was placed together with the master plate, so that a positive clone was collected from the top agarose and amplified. Thereafter, the second, third and fourth screenings were carried out in the same operations as described above. As a result, 22 positive clones were obtained from $7 \times 10^5$ phages by the first screening, and finally 3 positive clones (MMR10, MMR17 and MMR19) were obtained.

(4) Analysis of Gene Sequences of the Obtained Positive Clones

In the λZAP II phage vector, a plasmid vector Bluescript SK (−) as a whole is inserted between the initiator region and the terminator region of an f1 phage. Accordingly, a recombinant Bluescript is automatically cut out by infecting with a helper phage, and a cloned DNA fragment can be subcloned into the Bluescript. Thus, *Escherichia coli* XL1-Blue MRF' was infected with the three positive phages obtained in (3) above, and then the obtained product was infected with a helper phage for subcloning into pBluescript SK (−). This plasmid was transfected into *Escherichia coli* SOLR to obtain approximately 20 μg of plasmid DNA. The sequence of the plasmid DNA was analyzed by Primer Walking method. Using an ABI PRISM BigDye Primer Cycle Sequencing Core Kit (PE), the purified plasmid DNA was subjected to sequence reaction with an M13Rev primer and a −21M13 primer, and then using a long range gel, the DNA s quence was determined with an ABI 377 sequencer. As a result of the analysis, it was found that the MMR19 clone had a 840 bp full-length cDNA nucleotide sequence which comprised the open reading frame of the protein. In contrast, such an open reading frame was not confirmed in other clones. The nucleotide sequence of the MMR19 clone is shown in SEQ ID NO: 1.

(5) Primary Structure of Protein Predicted from Nucleotide Sequence of the cDNA Clone The primary structure (as shown in SEQ ID NOS: 1 and 2) of the protein (hereinafter referred to as "MMRP19 protein"), which was predicted from the nucleotide sequence of the gene (MMR19) analyzed in (4) above, was composed of 241 amino acid residues, and the predicted molecular weight was about 26.9 kDa.

Example 4

Comparison Between Mouse-derived MMR19 Gene and other Homologous Genes by Database Search With regard to the nucleotide sequence and the amino acid sequence shown in SEQ ID NO: 1, which were determined in Example 3, database search was carried out by the programs, such as BLAST, EMBC and PROSITE, and the presence or absence of homologous genes in human was analyzed both at amino acid residue level and at DNA level (GenBank, and DNA DATA BANK of JAPAN (DDBJ), Ministry of Education, Culture, Sports, Science and Technology. National Institute of Genetics, The Center for Information Biology). The obtained results are shown in the following Tables 1 and 2. As a result, it was shown that a gene highly homologous to the MMR19, the g ne of the present inv ntion, exists on human chromosome 9.

TABLE 1

| Homology at amino acid level | |
|---|---|
| Position in amino acid sequence shown in SEQ ID NO: 1 | Homology with human homologue |
| Amino acids 1 to 91 | 83/91 (91%) |
| Amino acids 50 to 146 | 83/97 (85%) |
| Amino acids 1 to 78 | 70/78 (89%) |
| Amino acids 200 to 241 | 40/42 (95%) |
| Amino acids 172 to 241 | 67/70 (95%) |
| Amino acids 103 to 150 | 46/48 (95%) |
| Amino acids 169 to 241 | 58/73 (79%) |

TABLE 2

| Homology at DNA level | |
|---|---|
| Position in nucleotide sequence shown in SEQ ID NO: 1 | Homology with human homologue |
| Nucleotides 519 to 736 | 189/218 (86%) |
| Nuoleotides 666 to 689 | 23/24 (95%) |
| Nucleotides 381 to 403 | 22/23 (95%) |
| Nucleotides 709 to 727 | 19/19 (100%) |

Example 5

Coning of MMR19 Human Homologous Counterpart

Total RNA derived from a human normal brain tissue (Invitrogen) was subjected to an oligo(dT) cellulose column to purify poly $A^+$ RNA. Thereafter, according to the method shown in Example 3 (2), cDNA was synthesized from the poly A+ RNA. With this cDNA as a template, PCR reaction was carried out using primers (a sense primer of positions 4 to 22; 5' CCATGTCTGGCTGTCAAGC-3' (SEQ ID NO: 5); an antisense primer of positions 721 to 701; 5'-CCATTTTCTCCAACTGGGAGC-3' (SEQ ID NO: 6)), which were prepared from a mouse antigen gene MMR19 sequence. As a result, a partial cDNA of an MMR19 human homologous counterpart was obtained. Subsequently, a full-length cDNA was obtained from the partial cDNA sequence of the obtained human homologous counterpart by a RACE method (using Marathon cDNA Amplification Kit from Clontech). That is, a cDNA library derived from human normal brain tissue was blunt-ended, and a Marathon cDNA Adaptor (including an AP1 primer sequence) was ligated hereto. Then, 5'-RACE PCR reaction was carried out using AP1 and GSP (Gene-Specific Primer) 1 (an antisense primer of positions 189 to 167: 5'-AATTCCTCCTCCAGTC-CCAGTGA-3' (SEQ ID NO: 7)), and 3'-RACE PCR reaction was carried out using GSP2 (a sense primer of positions 630 to 653: 5'-TGGAGTATATGTGTGGGGGAAAC-3' (SEQ ID NO: 8)) and AP1, so that the sequences on 5'- and 3'-terminal sides were amplified in both reactions. When these PCR products were subjected to agarose gel electrophoresis, a single band was observed regarding each PCR product. Accordingly, this was subjected to subcloning and then sequencing so as to decode the sequences of the 5'- and 3'-terminal sides. A sense primer (5'-AAGCCGTGCG-GAGATTGGAGG-3' (SEQ ID NO: 9); positions 1 to 21) was produced from the obtained 5'-RACE fragment, and an antisense primer (5'-GTCAGAAGAGATTCAGGGT-GACC-3' (SEQ ID NO: 10); positions 924 to 902) was produced from the obtained 3'-RACE fragment. With these primers, PCR reaction was carried out using the above used human normal brain tissue-derived cDNA library as a template, and the PCR product was subjected to T/A cloning using an AdvanTAge PCR Cloning Kit from Clontech so as to clarify the nucleotide sequence of the full-length cDNA of a human-type homolog comprising 1,136 bp open reading frame. The obtained nucleotide sequence is shown in SEQ ID NO: 3. Using Genetyx-Mac (Software Development Co., Ltd.), the homology between the human homologous counterpart cDNA and the mouse MMR19 cDNA (840 bp) was analyzed. As a result, it was found that these cDNAs have 85.0% homology with each other.

The primary structure of the protein predicted from the obtained nucleotide sequence of the MMR19 human homolog was comprised of 242 amino acid residues, which is shown in SEQ ID NOS: 3 and 4. The predicted amino acid sequence had 93.8% homology with that of mouse.

Example 6

Analysts of the MMRP19 Protein

Rabbit polyclonal antibodies APA1, APA2 and APA3 against three types of peptides consisting of the partial amino acid sequences of the MMRP19 protein were prepared as follows. That is to say, using a peptide synthesizer (Applied Biosystems 433 type), peptides corresponding to positions 12 to 25, 58 to 71, and 228 to 241 of the amino acid sequence of the protein predicted from the MMR19 were synthesized by 9-Fluorenylmethoxycarbonyl (FMOC) method, and the peptides were then purified by reverse phase chromatography (Shimadzu LC8A type), so that approximately 25 mg each of three types of peptides was finally obtained. The purified peptide was bound to a carrier protein hemocyanin (KLH) by an N-(6-maleimidocaproylxy)-succinimide crosslinking agent, each of the obtained product (1 mg) was mixed with Freund's complete adjuvant, and the obtained solution was immunized to a rabbit (female, 2 to 2.5 kg) by a subcutaneous injection into the dorsal subcutis about three times. After checking the antibody titer in the blood by ELISA, 100 ml of the blood was collected from each rabbit to prepare serum. Further, each anti-peptide antibody (APA1, APA2 and APA3) was obtained from the obtained serum using an IgG affinity column. APA1 is an antibody against a polypeptide having a sequence consisting of amino acids 12 to 25 of the amino acid sequence (SEQ ID NO: 2) of the MMRP19 protein. APA2 is an antibody against a polypeptide having a sequence consisting of amino acids 58 to 71 of the same sequence, and APA3 is an antibody against a polypeptide having a sequence consisting of amino acids 228 to 241 of the same sequence.

Using these anti-peptide antibodies and the 3-4H7 antibody, the RAW264.7 cell lysate was subjected to Western blot analysis. As a result, as shown in FIG. 1, all the bands recognized with any of these antibodies had a molecular weight of 30.4 kDa, and therefore it was confirmed that these antibodies are bound to the same protein, that is, the MMRP19 protein. It is considered that the difference between the thus obtained molecular weight (30.4 kDa) and the molecular weight calculated from the amino acid sequence (26.9 kDa) would be caused by sugar chain modification.

Figure 2:
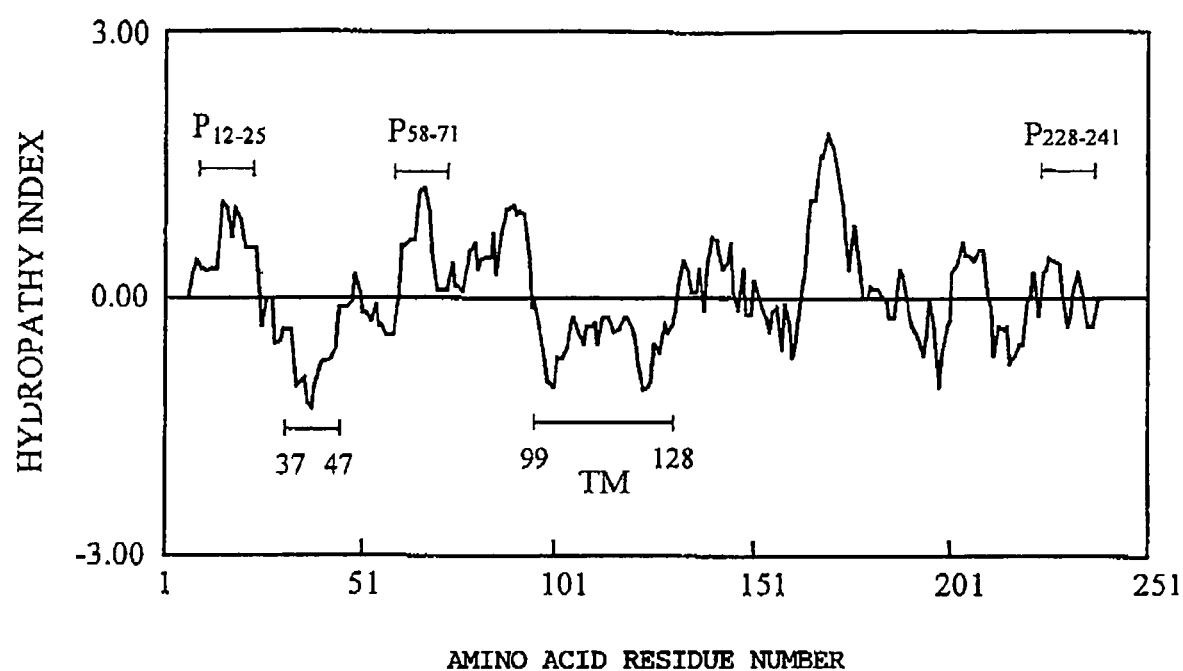
FIG. 2: Hydropathy plot of an MMRP19 protein. The horizontal axis, the number of amino acid residues; the longitudinal axis, hydropathy index. The amino acid sequence from Nos. 99 to 128 of the center portion seems to only represent the transmembrane (TM) domain of the MMRP19 protein.

Subsequently, the MMRP protein was subjected to hydropathy analysis according to Hoop and Woods method (Hoop, T. K. and Woods, K. P.: Mol. Immunol. 20, 483-489 (1983)). As a result, as shown in FIG. 2, the MMRP19 protein is likely to have two hydrophobic regions.

Figure 3:
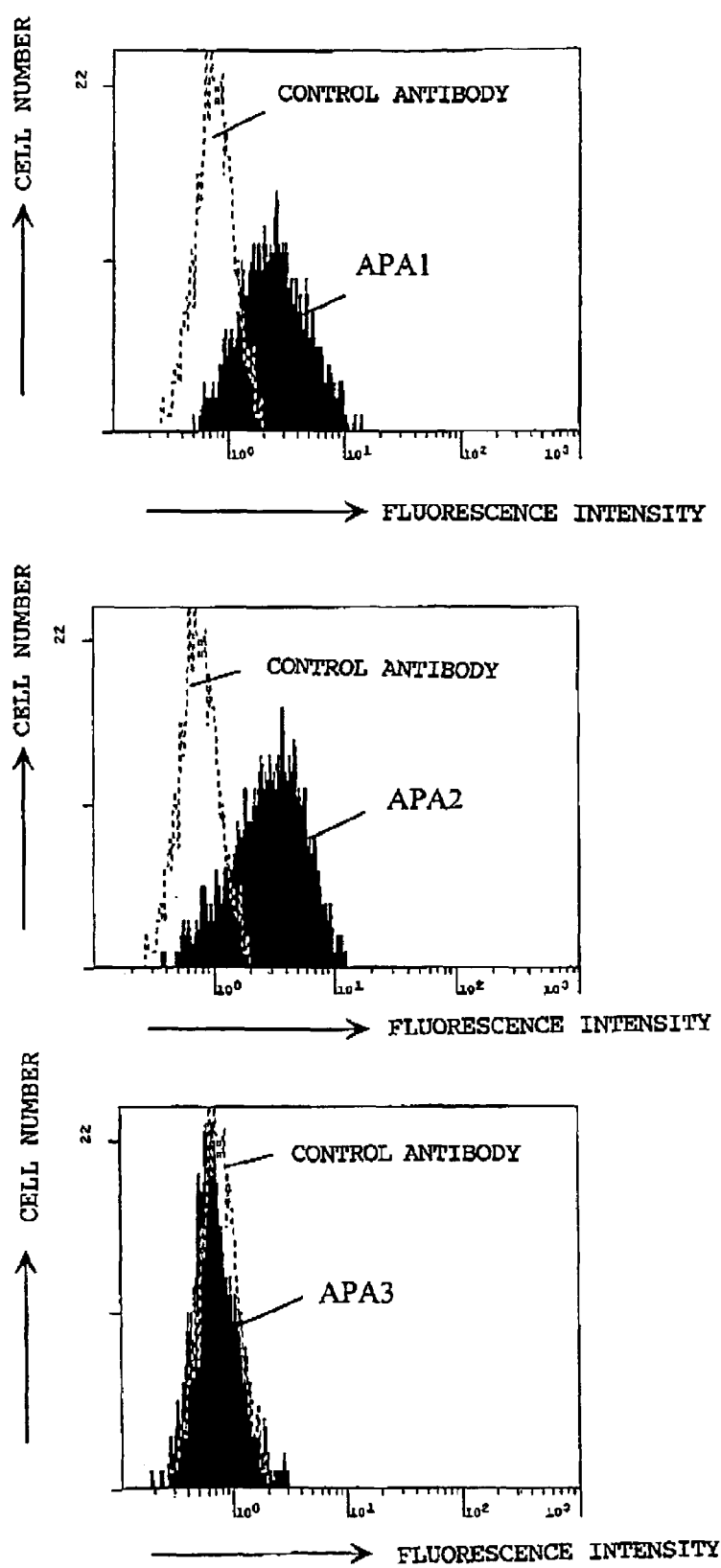
FIG. 3: Reactivity to the RAW264.7 cells of antibodies, each of which reacts against three types of partial peptide sequences of the MMRP19 protein. This figure shows the results obtained by analyzing the orientation of the MMRP19 protein in the cell membrane of the RAW264.7 cells by flow cytometry. The horizontal axis represents fluorescence intensity and the vertical axis represents the cell number. Each of APA1, APA2 and APA3 represents an anti-peptide antibody.

Thereafter, using the anti-peptide antibodies APA1, APA2 and APA3, the RAW264.7 cells were analyzed using a flow cytometer EPICS-ALTRA (Beckman Coulter). As a result, as shown in FIG. 3, the RAW264.7 cells were recognized by APA1 and APA2, but the cells were not recognized by APA3 that is an antibody against the C-terminal region of the MMRP19 protein.

These results suggest that the MMRP19 protein consists of an extracellular domain consisting of about 98 amino acid residues at the N-terminus, a transmembrane (TM) domain consisting of about 30 amino acid residues following the above domain, and an intracellular domain consisting of about 113 amino acid residues further following the above domain.

Example 7

Association of the MMRP19 Protein with Induction of G-CSF Gene Expression (1) Production of the Pica-RAW264.7 Cells A PicaGene System (Wako Pure Chemical Industries, Ltd.) was used, in which a luciferase gene was used as a reporter gene. A G-CSF promoter gene was inserted into the site from XboI to NcoI of a PicaGene Enhancer Vector 2 (Wako Pure Chemical Industries, Ltd.), a luciferage gene was ligated downstream of the site instead of the G-CSF gene, and further a neomycin-resistance gene cut from pMC1Neo Poly A was inserted into the SalI site located downstream of SV40, so that a PicaGCSFneo vector was constructed.

Subsequently, the above vector was introduced into the mouse macrophage cell line RAW264.7 using the following method. The RAW264.7 cell line, which was in the logarithmic growth phase, was collected and washed once with an Eagle medium (EMEM) containing 10% fetal bovine serum (FBS: Bio-Whittacker) and nonessential amino acid (NEAA). The cells were washed and resuspended in the same medium at a concentration of $2\times10^7$ cells/ml. The obtained cell suspension (250 μL, $5\times10^6$ cells) was placed in a 0.4 cm cuvette and then mixed with 10 μg of PicaGCSFneo plasmid DNA which was purified by cesium chloride method. Then, using a Gene Pulser (Bio-Rad), high voltage pulse of 300 V and 960 μF was applied on the mixture so as to introduce the vector into the cells.

Forty-eight hours after transformation, the obtained cells was treated with a medium containing 1 g/l geneticin (one type of neomycin), and 10 to 15 days later, cells forming a colony was selected. Forty-three out of the 50 geneticin resistant clones were stimulated with LPS, and as a result, significant increase of luciferase activity was observed. Of these clones, one clone showed extremely high luciferase activity, and this was called RAW264.7 clone 27-3 (referred to also as "Pica-RAW264.7 cell.")

Whether or not luciferase activity reflects the actual G-CSF mRNA expression was confirmed by the following experiment. That is to say, RAW264.7 clone 27-3 cells ($1.5\times10^7$) stimulated with LPS (10 μg/ml at a final concentration) for 18 hours were washed with PBS. The cells were dissolved, and the total RNA was extracted therefrom. The total RNA was electrophoresed on 1% formaldehyde agarose gel, and the total RNA was then transferred onto a nylon filter followed by Northern blot analysts using the $^{32}P$ labeled mouse G-CSF cDNA as a probe. As a control, β-actin was used. As a result, it was shown that the induction of the G-CSF mRNA correlates with the luciferase activity, and therefore it was confirmed that luciferase activity reflects the actual G-CSF mRNA expression.

(2) Detection of Induction of G-CSF Gene Expression

Figure 4:
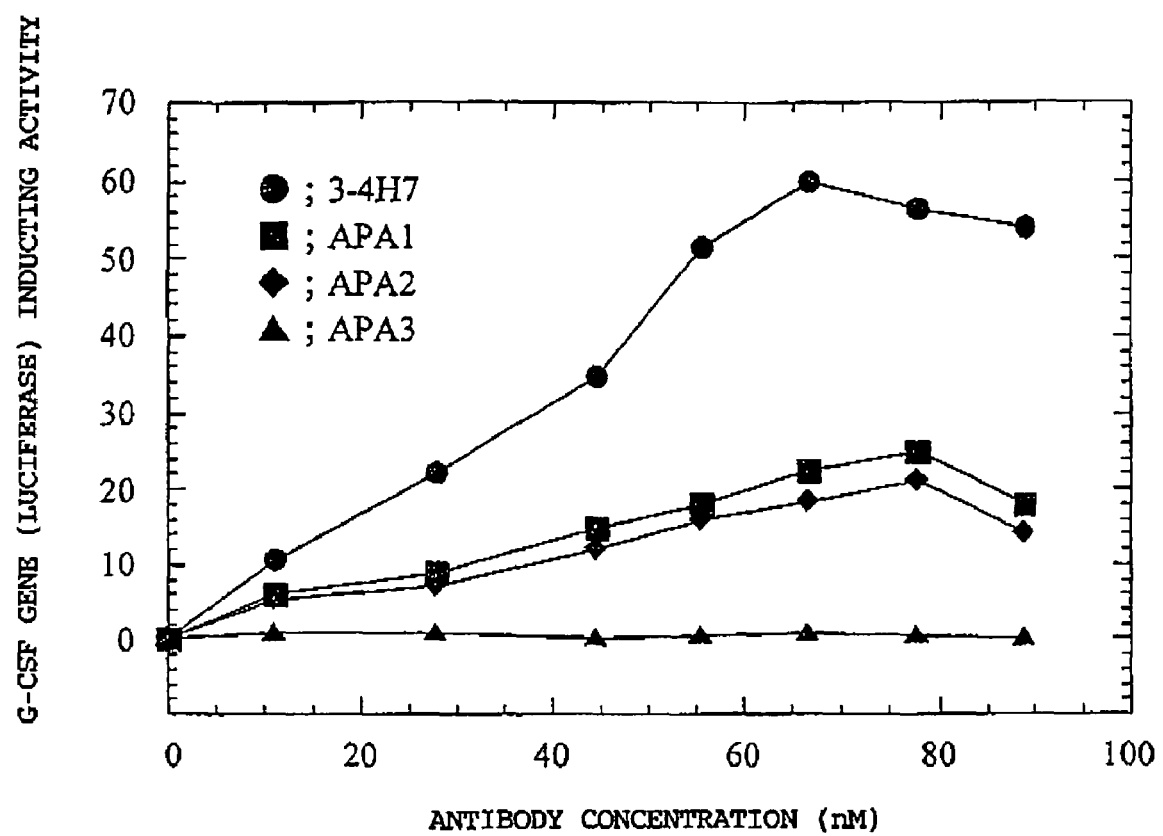
FIG. 4: Induction activity of G-CSF gene by the 3-4H7 antibody or by the anti-MMRP19 partial peptide antibodies (APAs). The figure shows that the MMRP19 protein is associated to function the induction of expression of a G-CSF gene. The horizontal axis represents the concentration of anti-MMRP19 protein antibodies added, and the vertical axis represents luciferase activity which corresponds to the induction of the G-CSF gene expression. The symbol ● represents the 3-4H7 antibody, the symbol ■ represents an anti-peptide antibody APA1, the symbol ♦ represents an anti-peptide antibody APA2, and the symbol ▲ represents an anti-peptide antibody APA3. Luciferase activity is shown as a relative value based on a respective control when a control value is defined as 1.
Figure 5:
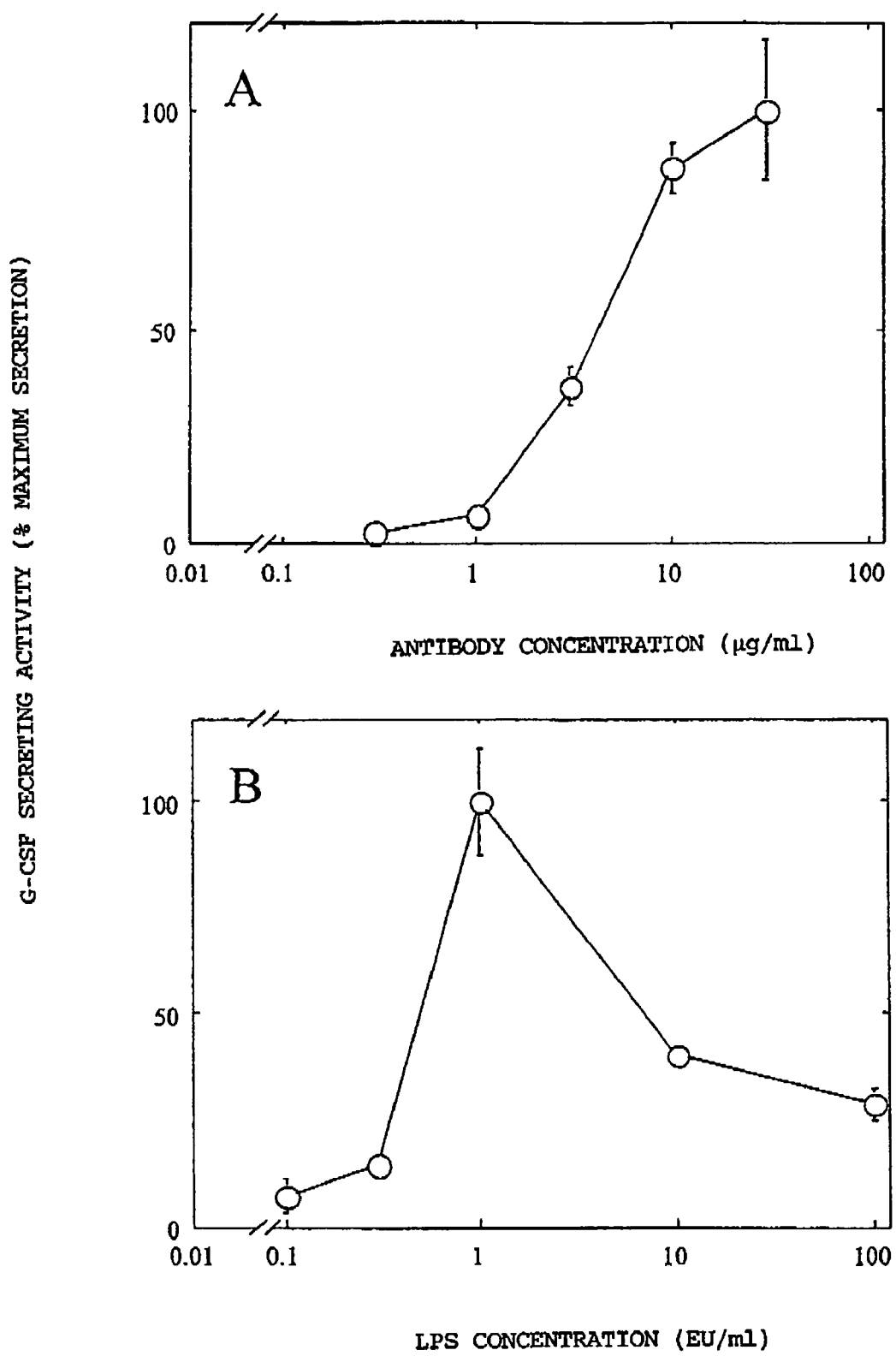
FIG. 5: Stimulating activity of G-CSF secretion by the 3-4H7 antibody (A) and LPS (B) in the RAW264.7 cells. The horizontal axis represents the concentration of the antibody (μg/ml) or the concentration of the LPS (EU/ml), and the vertical axis represents promoting activity of G-CSF secretion (%/maximum secretion).
Figure 6:
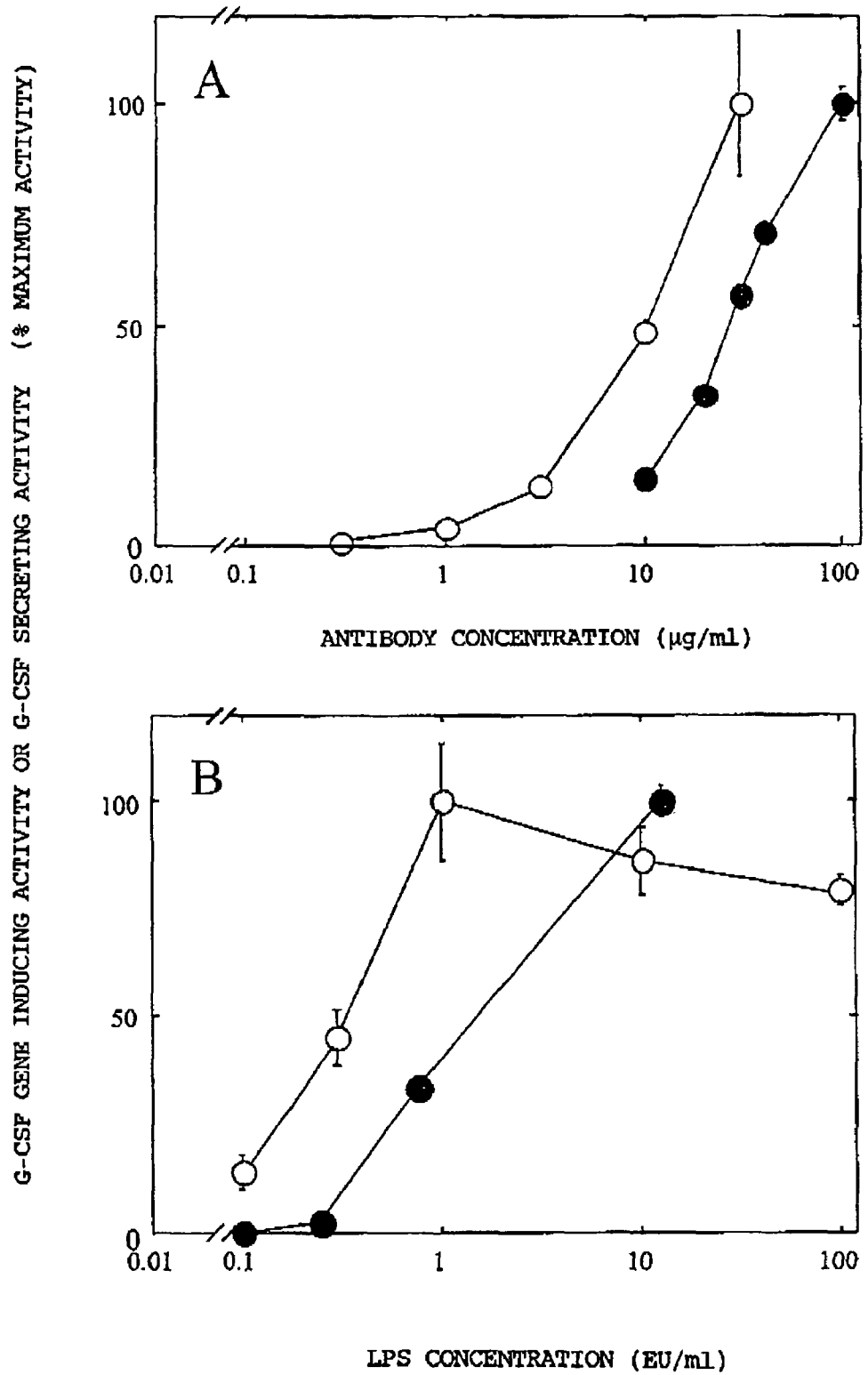
FIG. 6: Gene induction and secretion promotion activity of G-CSF by the 3-4H7 antibody (A) and LPS (B) in Pica-RAW264.7 cells. The horizontal axes represent the concentration of the antibody (μg/ml) and the concentration of the LPS (EU/ml), and the vertical axes represent the activity of G-CSF gene induction or the promoting activity of G-CSF secretion (%/maximum secretion). The symbol ● represents the activity of G-CSF gene induction, and the symbol ○ represents the promoting activity of G-CSF secretion.
Figure 7:
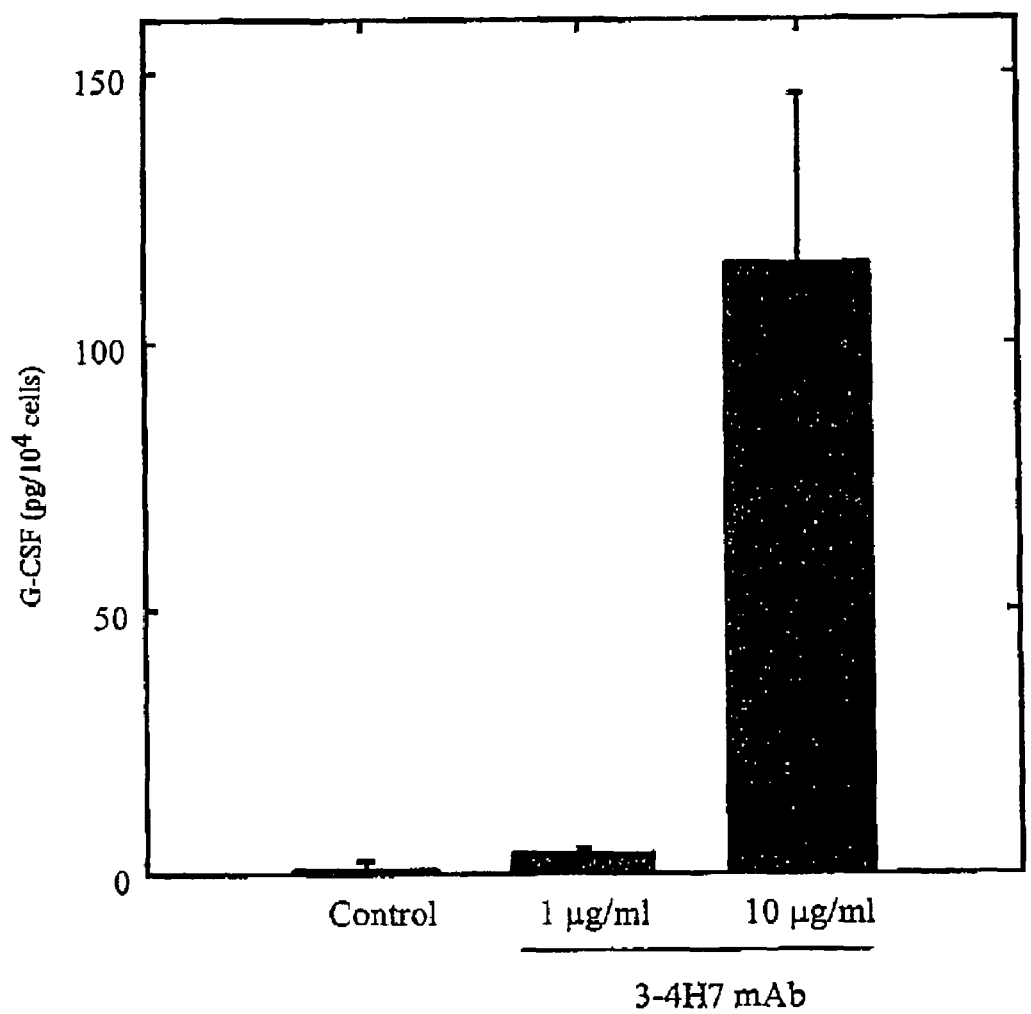
FIG. 7: Secretion amount of G-CSF by the 3-4H7 antibody in the RAW264.7 cells (n=6). The horizontal axis represents the concentrations of the 3-4H7 antibodies (0, 1 and 10 μg/ml). The vertical axis represents the secretion amount of G-CSF (pg/$10^4$ cells).
Figure 8:
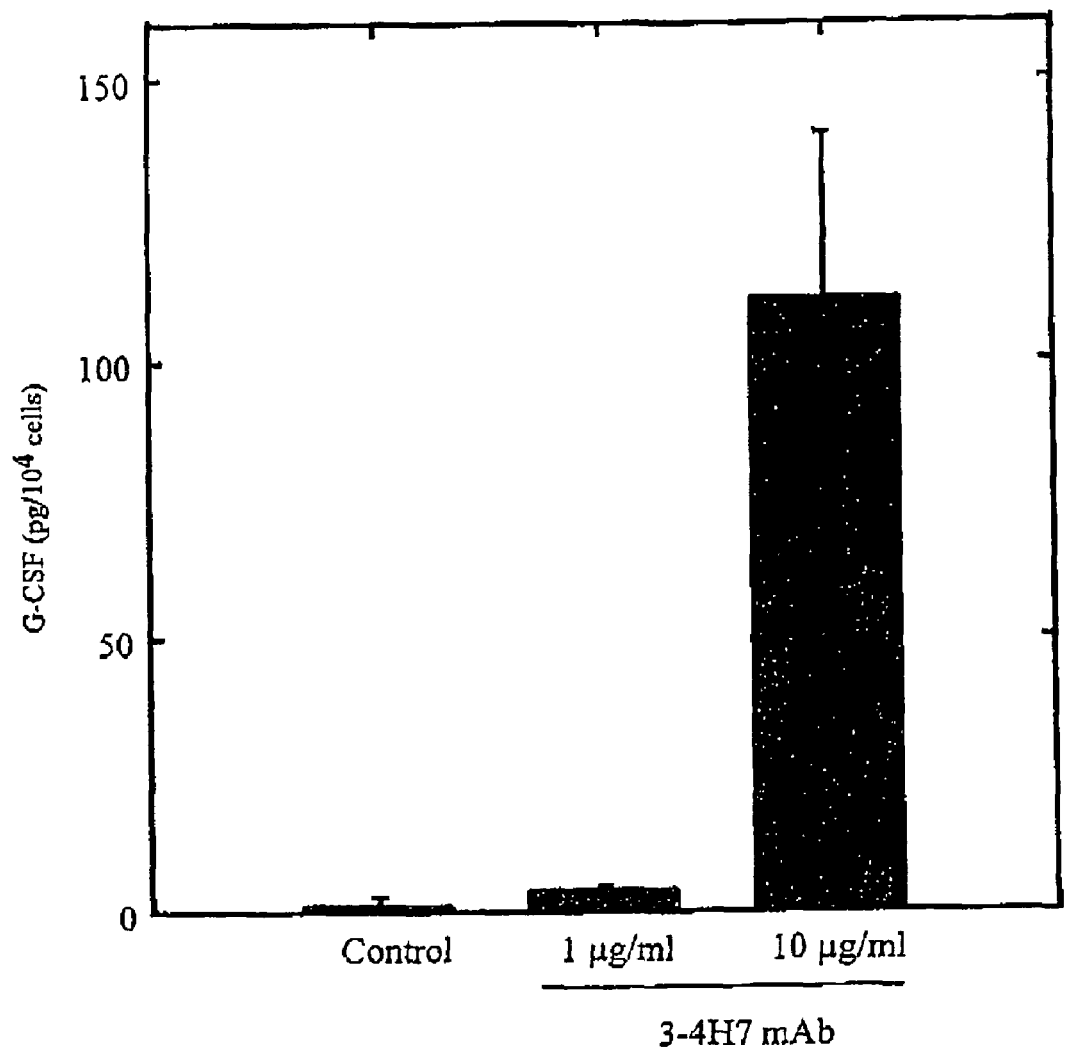
FIG. 8: Secretion amount of G-CSF by the 3-4H7 antibody in Pica-RAW264.7 cells (n=6). The horizontal axis represents the concentrations of the 3-4H7 antibodies (0, 1 and 10 μg/ml). The vertical axis represents the secretion amount of G-CSF (pg/$10^4$ cells).

The Pica-RAW264.7 cells were inoculated on a 96-well microplate so that the number of cells became $5\times10^4$ cells/100 μl per well, and the cells were cultured in an KMRM medium containing 10% FBS at 37° C. in the presence of 5% $CO_2$. The anti-peptide antibodies (APA1, APA2 and APA3) and the 3-4H7 antibody described in Example 6 were added to the plate at different concentrations, and the cells were stimulated overnight at 37° C. in the presence of 5% $CO_2$. These plates were washed three times with a PBS buffer, and the cells were dissolved with a PicaGene resolvent and then subjected to centrifugal separation. The luciferase activity of the obtained supernatant sample was determined with a Luminometer CT-9000D Chemoluminescence Determination Microplate Reader (Dia-Iatron Co., Ltd.). The results are shown in FIG. 4.

The 3-4H7 antibody at a concentration of 77 pmol/ml showed approximately 60-fold increase in G-CSF induction. As is the case with the 3-4H7 antibody, the anti-peptide antibodies (APA1 and APA2) recognizing the extracellular region also showed increase in G-CSF induction to the Pica-RAW264.7 cells (APA1: 24-fold, APA2: 21-fold). In contrast, the APA3 antibody recognizing the intracellular region showed no increase in G-CSF induction. From these results, it was shown that APA1 and APA2 are bound to the extracellular region of the MMRP19 protein and they are associated with the induction of G-CSF gene expression.

Example 8

Relationship Between Induction of G-CSF Gene Expression and Secretion by Stimulation by 3-4H7 Antibody in the Macrophage Cell Lines The RAW264.7 or Pica-RAW264.7 cells were suspended in an EMEM medium containing 10% FBS ($1.2\times10^5$ cells/ml), the cells of 90 μl per well ($1\times10^4$ cells/well) were inoculated on a 96-well microplate, and then they were subjected to preincubation overnight at 37° C. in the presence of 5% $CO_2$. Thereafter, 10 μl of the 3-4H7 antibody or LPS solution at various concentrations was added to the each well, and it was stimulated for 24 hours at 37° C. in the presence of 5% $CO_2$. Thereafter, the culture supernatant was placed in a sample tube and it was followed by centrifugal separation, and the supernatant was used for the following bioassay system detecting G-CSF using the NFS-60 cells. Detection of G-CSF by bioassay-was carried out as follows: That is, first, the NFS-60 cells were washed three times with PBS, and then the cells were suspended in an RPMI 1640 medium containing 5% FBS and 100 μM NEAA so that the density of cells became $3\times10^5$ cells/ml. Fifty μl each of the obtained NFS-60 cell suspension was inoculated on a 96-well microplate ($1.5\times10^4$ cells/well), preincubation was carried out overnight at 37° C. in the presence of 5% $CO_2$. Thereafter, a medium containing 50 μl of the culture supernatant of the RAW264.7 or Pica-RAW264.7 cells or a medium containing G-CSF was added to each well and it was followed by incubation for 24 hours at 37° C. in the presence of 5% $CO_2$. Thereafter, 10 μl of a WST solution (5 mM 2-(4-iodophenyl9-3-(4-nitrophenyl)-5-(2,4-disulfophenyl)-2H-tetrazolium-Na, 0.2 mM 1-methoxy-5-methylphenazinium methylsulfide, 20 mM Hepes, pH 7.4) was added to each well and it was followed by incubation at 37° C. for 4 hours. Growth of the NFS-60 cells was assayed by determining the absorbance at 450 nm, using 650 nm as a reference wave length, and the amount of G-CSF contained in the medium was assayed, using the calibration curve prepared using the cell growth induced by G-CSF as a reference. Moreover, as with in the case Example 7, the luciferase activity of the Pica-RAW264.7 cells was analyzed. As a result, as shown in FIGS. 5 to 8, it was shown that the 3-4H7 antibody, stimulates the RAW264.7 cells and the Pica-RAW264.7 cells, which is similar to LPS, and it conc ntration-dependently promotes the secretion of G-CSF. Since the secretion of G-CSF-required a lower concentration of the 3-4H7 antibody than that for the induction of the G-CSF gene, it was suggested that the biosynthesis and secretion of G-CSF requires only a small level of G-CSF gene induction.

Example 9

Epitopic Region of Antigen Molecule MMRP19 Recognized by 3-4H7 Antibody

Figure 9:
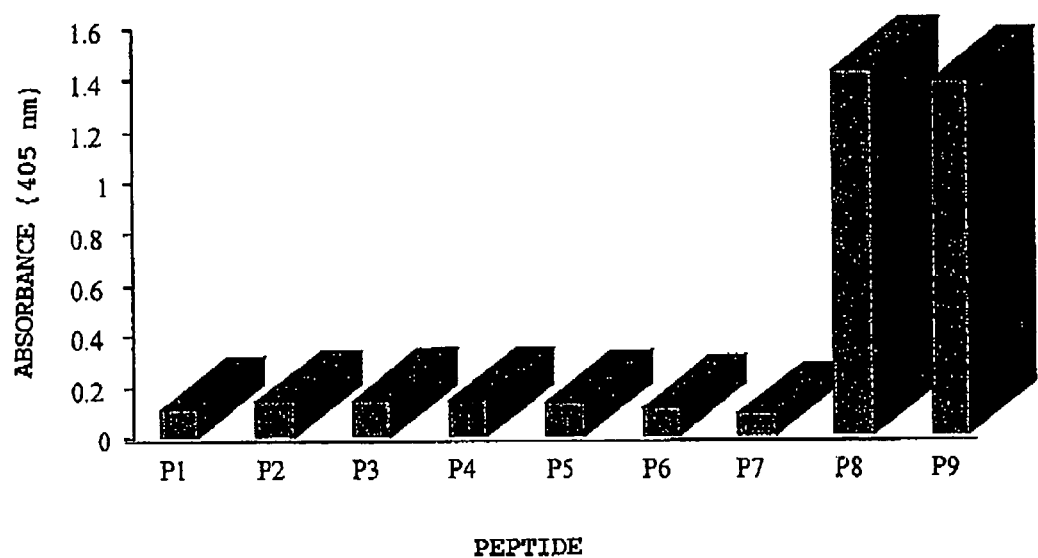
FIG. 9: Epitope mapping of the 3-4H7 antibody using the partial peptides from MMRP19. The horizontal axis represents the type of peptide fragments. The vertical axis represents adsorbancy at 405 nm.

Synthesis of peptides corresponding to the extracellular domains of the MMRP19 protein, MMRP19 (12-25, P1), MMRP19 (19-36, P2), MMRP19 (32-46, P3), MMRP19 (41-55, P4), MMRP19 (50-62, P5), MMRP19 (57-71, P6), MMRP19 (64-81, P7), MMRP19 (72-87, P8) and MMRP19 (81-98, P9) was carried out by 9-Fluorenylmethoxycarbonyl method, using a 433 Automated Peptide Synthesizer from Applied Biosystems. The synthesized peptide resin was treated with trifluoroacetic acid, and the treated product was purified using a reverse phase chromatography (Shimadzu LC8A) so as to obtain approximately 25 mg each of peptides. Each (0.5 µg) of the nine peptides (P1 to P9) corresponding to the MMRP19 extracellular domains was immobilized on a each well of a 96-well microplate, and then it was blocked with skim milk, and followed by washing three times with PBS. To this microplate, 50 µl of the 3-4H7 antibody solution was added (10 µg/ml at the final concentration), and the mixture was incubated at 37° C. for 1 hour. This was three times washed with PBS containing 0.05% Tween-20, and then a peroxidase labeled anti-mouse IgM rat antibody solution was added thereto and allowed to incubate them at 37° C. for 1 hour. The reaction product was further washed five times with PBS containing 0.05% Tween, and then a peroxidase substrate ABTS and hydrogen peroxide were added thereto and allowed to incubate them at 37° C. for 30 minutes. Thereafter, the absorption at 405 nm was determined using a Microplate Reader M-Tmax (Molecular Device). As a result, as shown in FIG. 9, only the peptides corresponding to positions 72 to 87 (P8) and 81 to 98 (P9) of the MMRP19 showed a binding ability to the 3-4H7 antibody, and the remaining peptides had almost no binding activity. These results show that the epitope of the MMRP19 to the 3-4H7 antibody exists in the positions 72 to 98 of the MMRP19 protein.

Example 10

Induction Pattern of Cytokine by 3-4H7 Antibody

Pica-RAW264.7 cells were inoculated on a 96-well microplate at $5 \times 10^4$ cells/100 µl per well. The cells were cultured in an EMEM medium containing 10% FBS at 37° C. in the presence of 5% $CO_2$. Thereafter, the cells were stimulated overnight with the 3-4H7 antibody (a final concentration at 60 µg/ml) or LPS (a final concentration at 100 ng/ml). After stimulation, the supernatant was collected and subjected to the measuring concentrations of various cytokines by ELISA. At the same time, the luciferase activity of the supernatant was determined so as to analyze the induction of G-CSF gene expression. As a control, a medium without neither the antibody nor LPS was used. Determination of IL-1α, IL-1β, IL-6, TNF-α and GM-CSF was carried out using a commercially available ELISA kit (Endogen). As a result, as shown in Table 3, the 3-4H7 antibody showed relatively high induction of G-CSF gene expression (approximately 60-fold). However, the level of inducing other cytokines was low (approximately 5.4-fold for IL-6, approximately 5.1-fold for TNF-α, significant change could not be detected for IL-1α, IL-1β and GM-CSF.) In contrast, LPS significantly induced not only G-CSF but also IL-1α, IL-β, IL-6, TNF-α and GM-CSF.

Example 11

Expression of the Human Counterpart of the MMR19 cDNA in Monkey-derived Cell Line COS7

A purified human counterpart of the MMR19 cDNA fragment was ligated to a plasmid vector (pCMV-Script), and the obtained recombinant vector (pCMV-Script MMR19) was transfected to the *Escherichia coli* XL10-Gold by heat shock. The recombinant vector produced from the *Escherichia coli* XL10-Gold was purified, and approximately 20 µg of the recombinant vector was transfected into monkey-derived cell line COS7 ($1 \times 10^7$ cells), which are the non-expression cells of the MMRP19 protein, by high voltage pulse method. Then, the cells into which the recombinant vector was introduced were cultured in a Dulbecco's modified Eagle's medium for two days and incubated with the antibody (3-4H7) at 4° C. for 1 hour. Thereafter, the reacted cells were stained with the FITC-labeled second antibody and then analyzed with a flow cytometer EPICS-ALTRA.(Beckman Coulter).

Figure 10:
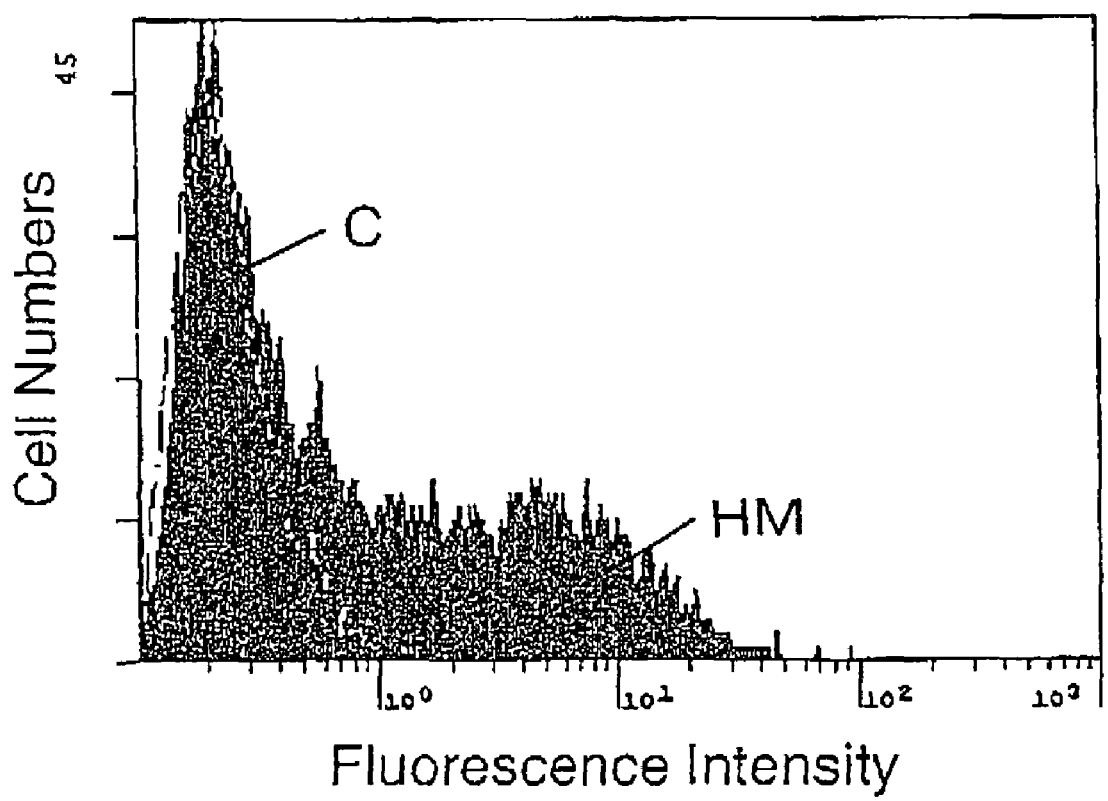
FIG. 10: Reactivity of the 3-4H7 antibody to COS7 cells. This figure shows the flow cytometric analysis of the expression in a monkey-derived cell line COS7 of a human counterpart of the MMR19 gene. The horizontal axis represents fluorescence intensity, and the vertical axis represents the cell number. C represents non-transformed control COS7 cells, and HM represents the COS7 cells, in which a human counterpart of the MMRP19 protein is expressed. Both the cells are stained with the 3-4H7 antibody.

As a result, as shown in FIG. 10, the 3-4H7 was bound to the cells in which the recombinant vector was introduced, and therefore it was found that as in the case of the mouse MMRP19 protein, a human counterpart of the MMRP19 protein expresses on the surface of cells.

Example 12

Excessive Expression of the MMRP19 Protein on the RAW264.7 Cell Membrane

First, purified MMR19 cDNA was integrated into the restriction enzyme ScaI site of an expression vector pCMV-Script (Stratagene) using DNA ligase, so that an MMR19 expression vector was prepared. The introduction of the expression vector into the RAW264.7 cell was carried out by high voltage pulse method (electroporation). That is to say, $2 \times 10^7$ of the RAW264.7 cells were suspended in 500 µl of potassium phosphate buffer, in which 10 µg of the vector was dissolved, and then the suspension was poured in a cuvette. A high voltage pulse of 500 µF and 300 V was applied thereon using Gene Pulser (Biorad), and thereby making a small pore on the cell membrane for a short time and introducing the vector into the cells. Subsequently, after applying the pulse, the cells were inoculated in a 250 ml flask and then cultured in a 10% FBS-EMEM medium at 37° C. for 72 hours. Thereafter, geneticin was added to the culture medium at a final concentration of 1 g/l, the cells were further cultured for two weeks, and the transformed

TABLE 3

| | Induction of G-CSF and other cytokines | | | | | |
|---|---|---|---|---|---|---|
| | G-CFS | IL-1α | IL-1β | IL-6 | TNF-α | GM-CSF |
| 3-4H7 mAb (60 µg/ml) | 57.8 ± 7.1 | 0.7 ± 0.2 | 2.2 ± 1.5 | 5.4 ± 0.5 | 5.1 ± 0.4 | 1.9 ± 0.4 |
| LPS (100 ng/ml) | 496.5 ± 13.7 | 93.6 ± 5.6 | 30.7 ± 8.7 | 1274.7 ± 410.0 | 475.7 ± 181.8 | 113.6 ± 21.8 |

All values are based on the control value which is defined as 1.

cells resistant to geneticin were selected. Further, cells reacting to the 3-4H7 antibody were selected twice from the obtained transformed cells by flow cytometry, so that the RAW264.7 (OE-RAW264.7) cells excessively expressing the MMRP19 protein were obtained.

Figure 11:
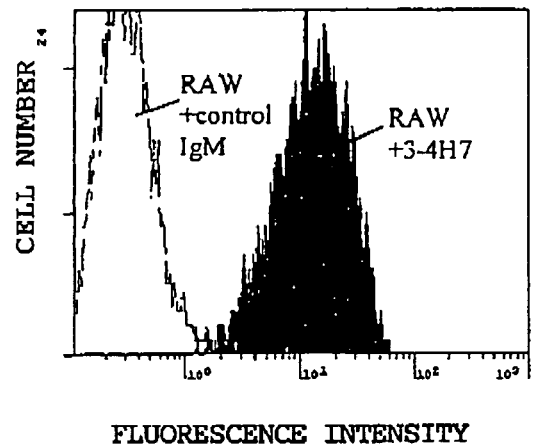
FIG. 11: Excessive expression of MMRP19 in RAW264.7 cells. This figure shows the flow cytometric analysis of which the expression in RAW264.7 cells (an non-transformed cell line) or in RAW264.7 cells where the MMR19 gene is excessively expressed (OE-RAW264.7; transformed cells) of a human counterpart of the MMR19 gene. The horizontal axis represents fluorescence intensity, and the vertical axis represents the cell number.
Figure 11:
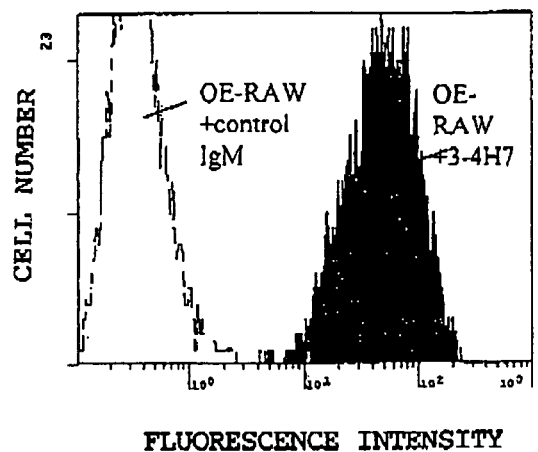
Figure 11:
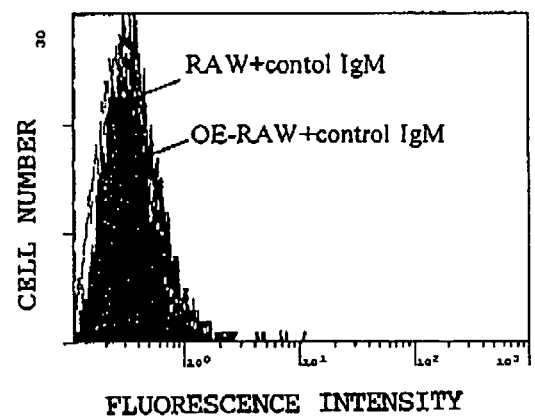
Figure 11:
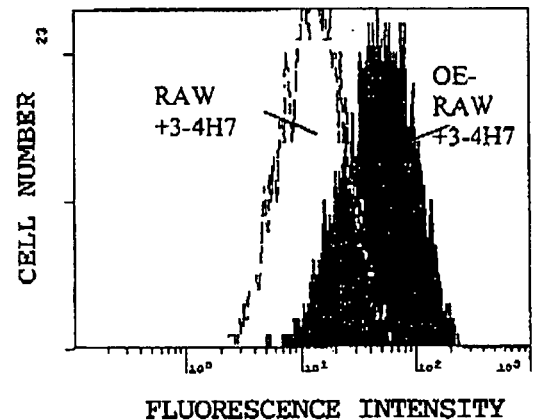

The flow cytometric analysis of the MMRP19 protein expressed on the cell membrane of the RAW264.7 or OE-RAW264.7 cells was carried out as follows: That is to say, the RAW264.7 or OE-RAW264.7 cells were prepared at $1.5 \times 10^6$ cells in 100 µl of PBS, and then the 3-4H7 antibody was added thereto (final concentration 5 µg/100 µl) followed by reaction at 4° C. for 1 hour. The reaction product was washed three times with PBS containing 5% FBS and 0.05% $NaN_3$ by centrifugal separation, then an FITC fluorescent labeled anti-mouse IgM antibody was added to the cell suspension at a final concentration of 3 µg/100 µl, and the mixture was further reacted at 4° C. for 1 hour in shade. Thereafter, the cells were washed five times with PBS containing 5% FBS and 0.05% $NaN_3$ by centrifugal separation, and the fluorescent labeled cells were detected and analyzed by flow cytometry (EPICS ALTRA, Beckman Coulter). As a result, as shown in FIG. 11, it was shown that when compared with the RAW264.7 cells, the OE-RAW264.7 cells express an excessive amount of the MMRP19 protein on the cell membrane, and it was found that the MMRP19 was expressed as a cell membrane prot in.

Example 13

Figure 12:
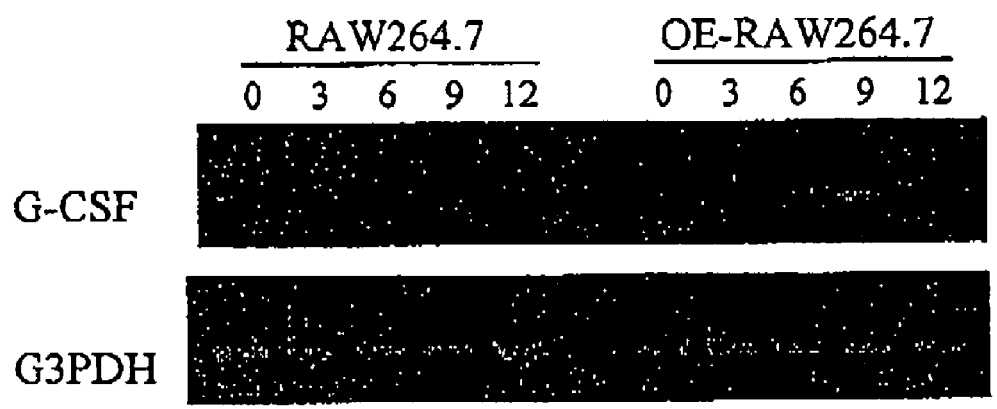
FIG. 12: Induction of G-CSF gene expression in OE-RAW264.7 cells where an excessive amount of the MMRP19 protein is expressed. Each number represents time after stimulation, and the upper case represents the band of G-CSF amplified by PCR whereas the lower case represents the band of a control G3PDH amplified by PCR.
Figure 12:
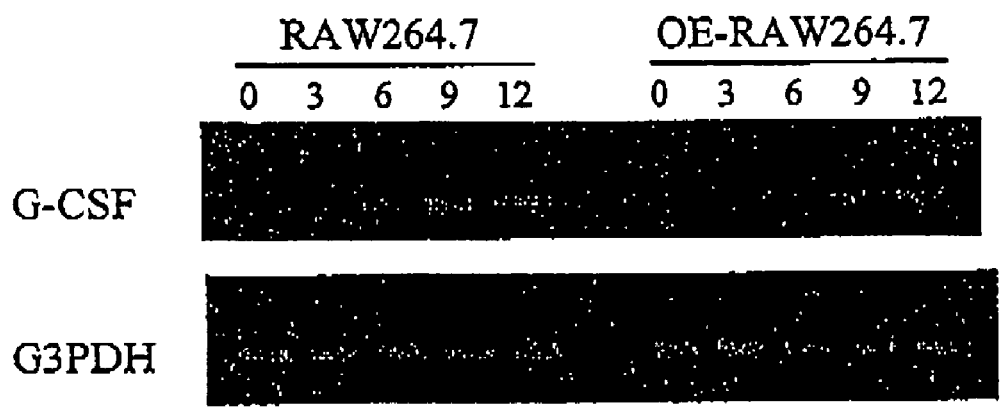

Study of the Effect of MMRP19 Protein for Excessive Expression of G-CSF Gene Induction by 3-4H7 Antibody Stimulation in Macrophage Cells The RAW264.7 cells, the OE-RAW264.7 cells of the MMRP19 protein excessive expression cells, were inoculated on a 6-well microplate, so that the number of cells for each well became $1.5 \times 10^6$ cells ($5 \times 10^5$ cells/ml), and the cells were cultured overnight at 37° C. in the presence of 5% $CO_2$. The 3-4H7 antibody (at final concentration of 50 µg/ml) or LPS (at final concentration of 100 ng/ml) was added to the culture and allowed to stimulate the G-CSF gene induction at 37° C. in the presence of 5% $CO_2$ for 3, 6, 9 or 12 hours. Then, the total RNA was extracted from the RAW264.7 cells or OERAW264.7 cells stimulated with the 3-4H7 antibody or LPS as described above by Guanidium Thiocyanate/Phenol Chloroform Extraction, and using reverse transcriptase (MMLV-RTase) and DNA polymerase, cONA was synthesized from the total RNA. Thereafter, using a sense primer (5'-GCTGTGGCAAAGTGCACT-3' (SEQ ID NO: 11)) corresponding to the positions 121 to 138 of the mouse GCSF gene sequence and an antisense primer (5'-ATCTGCTGCCAGATGGTG-3' (SEQ ID NO: 12)) corresponding to the positions 537 to 520 of the same sequence, RT-PCR reaction was carried out. As a result, as shown in FIG. 12, in the RAW264.7 cells, significant G-CSF mRNA-induction was observed at as many as 6 hours after stimulation with the 3-4H7 antibody, but in the OE-RAW264.7 cells, G-CSF mRNA induction had already been observed at 3 hours after the stimulation. In the case of stimulation by LPS, G-CSF mRNA was induced at as many as 6 hours after the stimulation both in the RAW264.7 cells and in the OE-RAW264.7 cells. Thus, it was shown that when stimulation with the same concentration of 3-4H7 antibody is given to both types of cells, G-CSF mRNA-induction occurs more quickly in the OE-RAW264.7 cells than in the RAW264.7 cells. However, in the case of stimulation with LPS, no significant difference was observed between the two types of cells regarding G-CSF mRNA induction. From the above results, it was suggested that the G-CSF gene is induced by the binding of the 3-4H7 antibody to the MMRP19 protein. Moreover, it was also suggested that in the RAW264.7 cells or OE-RAW264.7 cells, the signal transmitting route regarding G-CSF induction by stimulation with the 3-4H7 antibody might differ from the case of stimulation with LPS.

Example 14

Figure 13:
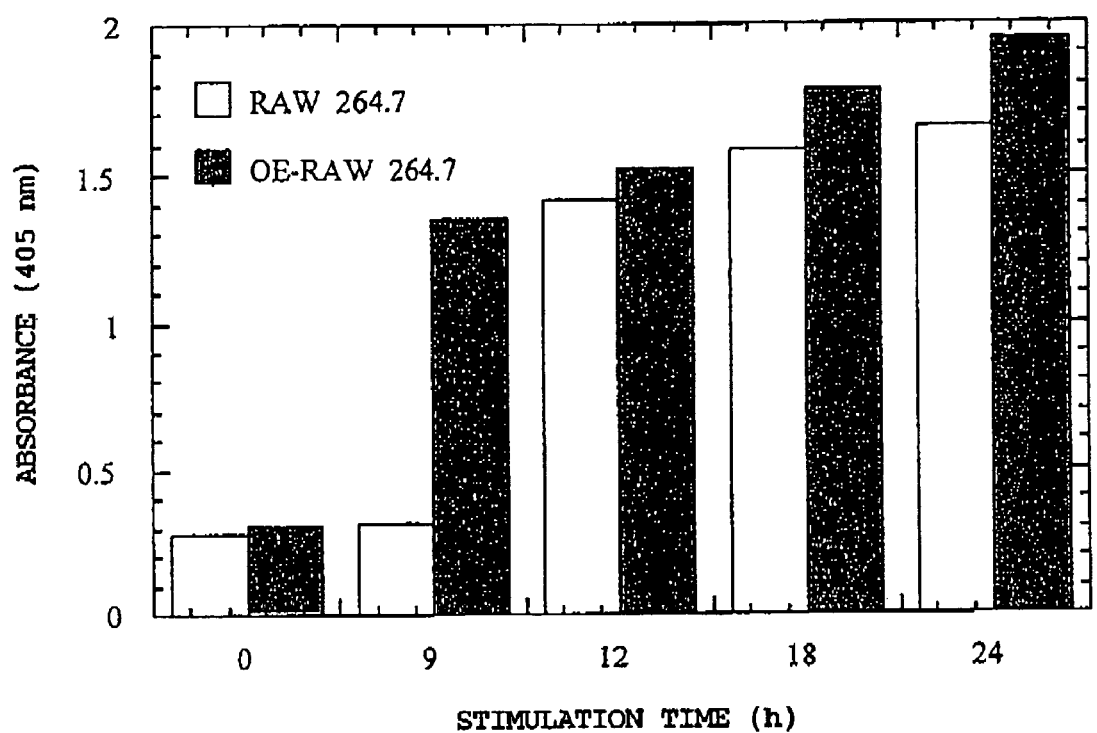
FIG. 13: Increase in the secreted amount of G-CSF upon stimulation with the 3-4H7 antibody to the cells where the MMRP19 is excessively expressed. The secreted amount of G-CSF upon stimulation with the 3-4H7 antibody to the RAW264.7 cells or OE-RAW264.7 cells is detected by ELISA. The horizontal axis represents the time course, and the vertical axis represents absorbance at 405 nm (the secreted amount of G-CSF).

Enzymatic Immunodetection of G-CSF Secretion by Stimulation with 3-4H7 Antibody in Macrophage Cells and Study of the Effect of the MMRP19 Protein Excessive Expression The RAW264.7 cells, or the OE-RAW264.7 cells with the MMRP19 protein excessive expression were inoculated in a 5 cm petri dish, so that the number of cells became $1.5 \times 10^6$ cells/5 ml ($3 \times 10^5$ cells/ml), and the cells were cultured overnight at 37° C. in the presence of 5% $CO_2$. The 3-4H7 antibody (final concentration at 50 µg/ml) was added to the culture that was followed by stimulation at 37° C. in the presence of 5% $CO_2$ for 9, 12, 18 or 24 hours, and 100 µl of the culture supernatant was collected after the above stimulation times. The culture supernatant was transferred onto a 96-well immunoplate (Nunc, MaxiSorp), and solidified at 4° C. overnight that was followed by washing three times with 400 µl of PBS containing 0.05% Tween 20. Thereafter, 100 µl of rabbit serum was added to each well, and the mixture was incubated at room temperature for 30 minutes so that the well was blocked, and then it was again washed three times with 400 µl of PBS containing 0.05% Tween 20. Thereafter, 100 µl of an anti-mouse G-CSF goat antibody (R&D) which was prepared at a concentration of 10 µg/ml was added thereto, and the mixture was incubated at 4° C. overnight that was followed by washing five times with 400 µl of PBS containing 0.05% Tween 20. Thereafter, 100 µl of a biotinated anti-goat Ig rabbit antibody solution was further added to each well of the plate, and the mixture was incubated at room temperature for 1 hour that was followed by washing three times with 400 µl of PBS containing 0.05% Tween 20. Thereafter, 100 µl of an avidin-peroxidase solution was further added thereto, and the mixture was incubated at room temperature for 30 minutes that was followed by washing five times with 400 µl of PBS containing 0.05% Tween 20. After that, 100 µl of a peroxidase substrate ABTS solution was added to each well and allowed to set at room temperature for 30 minutes, and thereafter the absorption at 405 nm was analyzed using a Microplate Reader M-Tmax (Molecular Device). As a result, as shown in FIG. 13, it was shown that the 3-4H7 antibody promotes the secretion of the G-CSF time-dependently in the RAW264.7 cells, or the OE-RAW264.7 cells with the MMRP19 protein excessive expression cells, and that the activity is significantly higher in the OE-RAW264.7 cells. From these results (including Examples 7, 8 and 13), it was suggested that the 3-4H7 antibody binds to the MMRP19 protein existing on the surface of the macrophage-like cell line, RAW264.7 cell, and activates the protein so as to allow the protein to induce or promote the secrection of G-CSF.

Example 15

Functional Analysis of MMRP19 Protein Homolog in Human Cells

Human-derived cultured cells, HL-60 cells (Riken, The Institute of Physical and Chemical Research) were placed in an RPMI 1640 medium containing 10% FBS so that the cell density became $1.5 \times 10^5$ to $1.5 \times 10^6$ cells/ml and cultured at 37° C. in the presence of 5% $CO_2$. Differentiation of the HL-60 cells into neutrophil-like cells was carried out by treating the cells with 500 μM dibutyryl cAMP (dbcAMP) for 3 days. Further, the differentiation of the HL-60 cells into macrophage-like cells was carried out by treating the cells with 100 μg/ml phorbol 12-myristate 13-acetate (PMA) for 3 days.

First, for undifferentiated HL-60 cells, the neutrophil-like differentiated HL-60 cells and the macrophage-like differentiated HL-60 cells, the presence of the cell membrane surface antigen recognized by the 3-4H7 antibody was examined by flow cytometry. As a result, it was shown that surface antigen for the 3-4H7 mAb antibody is present only in the macrophage-like differentiated HL-60 cells, but the antigen is not present in the undifferentiated or the neutrophil-like differentiated HL-60 cells. Moreover, when the lysates of undifferentiated, neutrophil-like differentiated and macrophage-like differentiated HL-60 cells were prepared, and the synthesis of a human counterpart of the MMRP19 protein was analyzed by Western blotting using the 3-4H7 antibody, or when the gene was detected by RT-PCR, the same results were obtained. From these results, it was shown that the human counterpart of the MMRP19 protein that is an antigen for a 3-4H7 antibody expresses, when the HL-60 cell that is a human cultured cell is differentiated into a macrophage-like cell by PMA.

Subsequently, the activity of the 3-4H7 antibody to induce or promote the secretion of G-CSF in the HL-60 cells was studied. That is, undifferentiated, neutrophil-like differentiated and macrophage-like differentiated HL-60 cells were stimulated with the 3-4H7 antibody at a final concentration of 60 μg/ml at 37° C. for 18 hours in the presence of 5% $CO_2$. Thereafter, G-CSF secreted in the culture supernatant was detected by G-CSF bioassay (Example 8) and enzyme immunoassay (Example 14). Further, G-CSF contained in the cells at this time was detected by Western blotting, and G-CSF mRNA was detected by RT-PCR (Example 13). As a result, it was shown that G-CSF is secreted again only in the culture supernatant from the macrophage-like diff rentiated HL-60 cells. From the above results, it was suggested that the 3-4H7 antibody binds to the human-type MMRP19 protein and activates the protein so as to allow the protein to induce or promote the secrection of G-CSF also in the macrophage-like differentiated HL-60 cells.

Example 16

Induction of G-CSF mRNA Expression by 3-4H7 Antibody (Anti-MMRP19 Antibody)

<Method>

(1) Action of 3-4H7 Antibody on Bone Marrow Cells and Peritoneal Macrophage Cells from the Normal Mice Using BALB/c mice (male, 7-week old), bone marrow cells from the femur and the shank as well as the peritoneal macrophage cells were collected. An appropriate amount of cold Hank's balanced salt solution was sucked in a 1 ml syringe with a 21G needle, and the tip of the needle was thrust into the bone cavity of the extirpated femur and shank to collect 2 mL of bone marrow cells into the tube. Moreover, an appropriate amount of cold Hank's balanced salt solution was sucked in a 1 ml syringe, the abdominal cavity was well washed, and cells suspended in PBS solution were collected. This operation was repeated twice, and peritoneal macrophages were collected. The thus collected bone marrow cells ($1.5 \times 10^6$ cells) and peritoneal macrophage cells ($5 \times 10^5$ cells) were incubated in an incubator at 37° C. in the presence of 5% $CO_2$ for 18 hours. After cells were incubated, the 3-4H7 antibody (1,2,5,10 and 20 μg/ml) was added thereto, and the mixture was further cultured in an incubator at 37° C. in the presence of 5% $CO_2$ for 6 hours. A group by adding only the solvent was used as a control.

Figure 14:
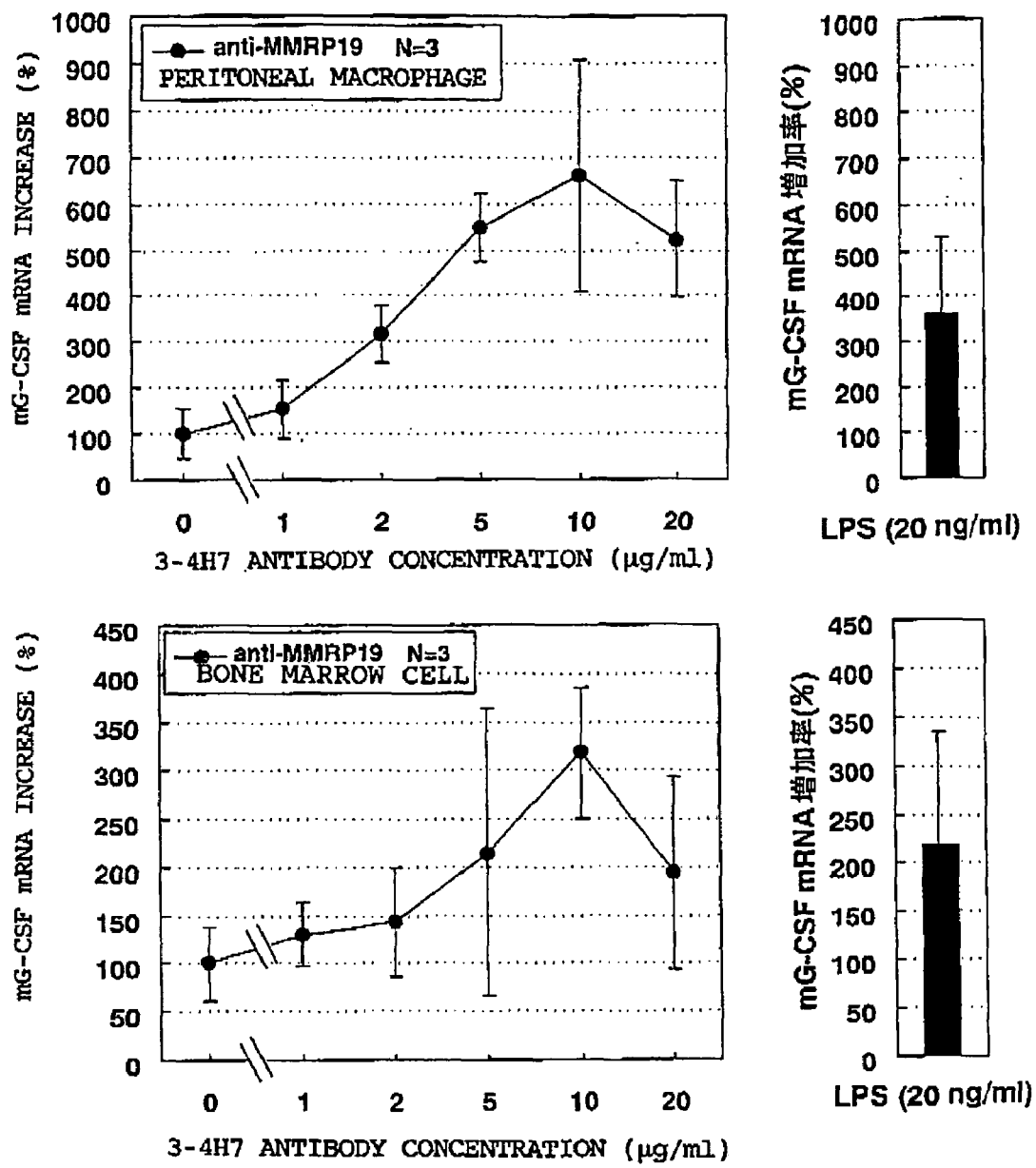
FIG. 14: The mouse G-CSF mRNA induction of the 3-4H7 antibody against the peritoneal macrophage cells and the bone marrow cells. Peritoneal macrophage cells (0.5× $10^6$) or bone marrow cells (1.5×$10^6$) are left in culture plates for 18 hours. The 3-4H7-antibody or LPS are then added there and further cultured for 6 hours. After the 6 hours culture, RNA is extracted using an RNeasy kit, and the amount of the mouse G-CSF mRNA is measured by quantitative RT-PCR (PRISM 7700). Moreover, the amount of GAPDH mRNA is measured as an internal standard so as to correct the amount of RNA.

As a result, the amount of G-CSF mRNA in the peritoneal macrophage cells increased by approximately 6.5-fold in the presence of the 3-4H7 antibody (10 μg/ml) (FIG. 14). The cells were simultaneously stimulated with 20 ng/ml LPS, and the amount of G-CSF mRNA in the peritoneal macrophage cells increased by approximately 3.6-fold (FIG. 14). Moreover, the amount of G-CSF mRNA in the bone marrow cells increased by approximately 3.2-fold in the presence of the 3-4H7 antibody (10 μg/ml) (FIG. 14). The cells were simultaneously stimulated with 20 ng/ml LPS, and the amount of G-CSF mRNA in the bone marrow cells increased by approximately 2.2-fold (FIG. 14).

(2) Action of the 3-4H7 Antibody on the Normal Mouse Liver-derived Kupffer Cell

A mouse was anesthetized with pentobarbital, and the abdomen was then incised while trying not to damage the liver. The bowel was placed to the right so as to expose the portal and the inferior vena cava, and a liver perfusion liquid was perfused from the portal vein by a perista pump so that the blood was removed from the liver. The liver was then treated with a collagenase solution. The liver was extirpated, and the extirpated liver was gently dissolved with a 10% FCS/RPMI 1640/penicillin-streptomycin medium followed by filtration with a mesh and the supernatant was collected in a 50 ml centrifugation tube. Centrifugal separation was carried out under conditions at 550 rpm for 2 minutes and at 4° C. to collect a supernatant. This operation was repeated twice. Centrifugal separation was carried out under conditions at 1,500 rpm for 10 minutes and at 4° C. to eliminate the supernatant, and then 10 ml of an RPMI 1640 medium was added to the remaining cell block to obtain a cell suspension solution. The cell suspension was incubated in an incubator at 37° C. in the presence of 5% $CO_2$ for 1 hour and then it was washed three times with an RPMI 1640 medium to eliminate non-adhesive cells other than Kupffer cells. The 3-4H7 antibody (10, 30 μg/ml) or lipopolysaccharide (LPS, 1 μg/ml) was added to the prepared Kupffer cells, and the mixture was cultured in an incubator at 37° C. in the presence of 5% $CO_2$ for 1, 3 and 6 hours. A group to which only the solvent was added was used as a control.

Figure 15:
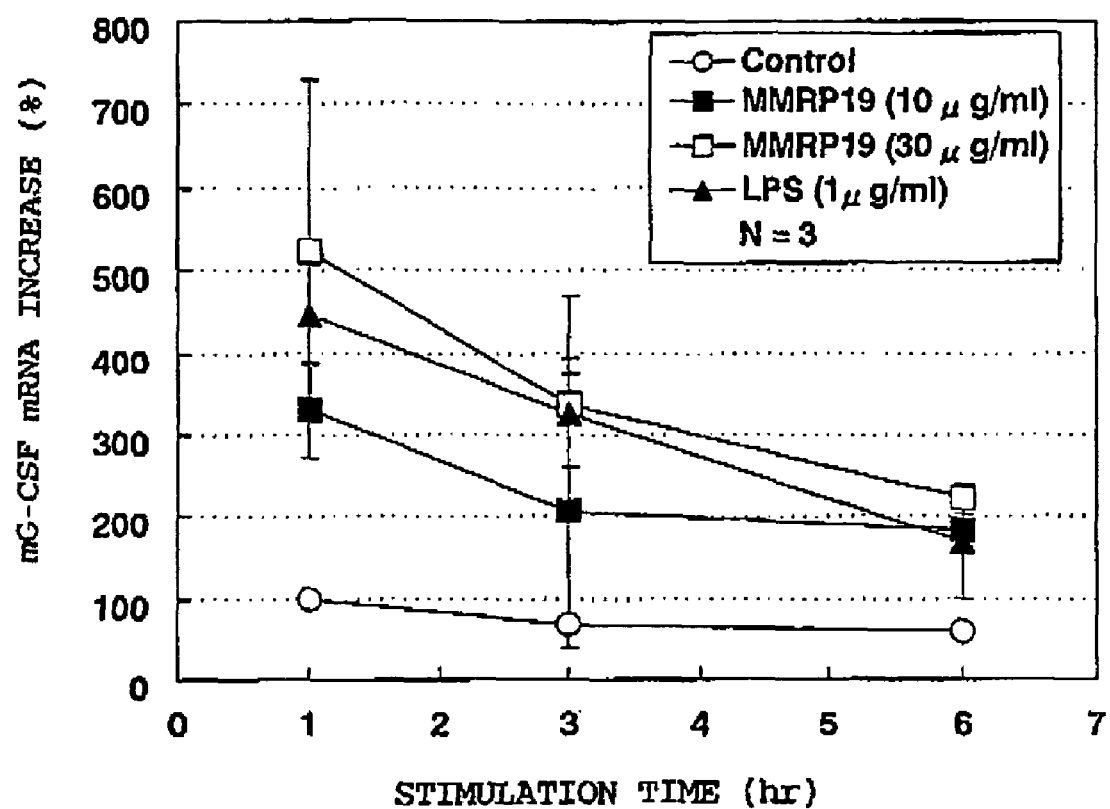
FIG. 15: The mouse G-CSF mRNA induction of the 3-4H7 antibody against the mouse liver-derived Kupffer cells. Kupffer cells are prepared from the mouse liver, and 3-4H7 antibodies (10, 30 μg/ml) or LPS (1 μg/ml) are added there. After 1, 3 and 6 hours, the Kupffer cells are collected and RNA is extracted using an RNeasy kit. The amount of the mouse G-CSF mRNA is measured by quantitative RT-PCR (PRISM 7700). Moreover, the amount of GAPDH mRNA is measured as an internal standard so as to correct the amount of RNA.

As a result, at 1 hour after stimulation by the 3-4H7 antibody (30 μg/ml), the amount of G-CSF mRNA in the liver-derived Kupffer cells increased by approximately 5.2-fold (FIG. 15). The liver-derived Kupffer cells were simultaneously stimulated with 1 μg/ml of LPS for 1 hour, and the amount of G-CSF mRNA in the cells increased by approximately 4.4-fold (FIG. 15).

(3) Action of 3-4H7 Antibody on the Normal Mouse Peripheral Blood-derived Macrophage Cells An equivalent amount of 10% FCS/RPMI 1640/penicillin-streptomycin medium was added to the blood collected from the mouse heart to prepare a cell suspension solution. Lymphoprep (Nycomed) was placed in a 15 ml centrifugation tube, the cell suspension solution was gently placed thereon and it was followed by centrifugal separation at 2,300 rpm for 20 minutes at 4° C. The intermediate layer was gently collected, and to the collected layer of cell suspension solution, the medium was added and fully mixed, followed by centrifugal separation at 2,500 rpm for 5 minutes at 4° C. The supernatant was eliminated, the remaining cells were dissolved, and an RPMI 1640 medium was added thereto, followed by centrifugal separation at 1,500 rpm for 5 minutes at 4° C. This operation was repeated twice, and the cells were well washed. The viable cell was counted after staining them with a trypan blue solution. The cell suspension solution ($2 \times 10^6$ cells) was inoculated on a 24-hole plate, and the plate was incubated in an incubator at 37° C. in the presence of 5% $CO_2$ for 1 hour. Thereafter, it was washed three times with a medium to eliminate non-adhesive cells. M-CSF (30 ng/ml) was added to each well and the mixture was cultured in an incubator at 37° C. in the presence of 5% $CO_2$ for 4 days. The 3-4H7 antibody (10, 30 μg/ml) or LPS (1 μg/ml) was added to the prepared macrophage cells, and the mixture was cultured in an incubator at 37° C. in the presence of 5% $CO_2$ for 15 minutes and 1 hour. A group to which only the solvent was added was used as a control.

Figure 16:
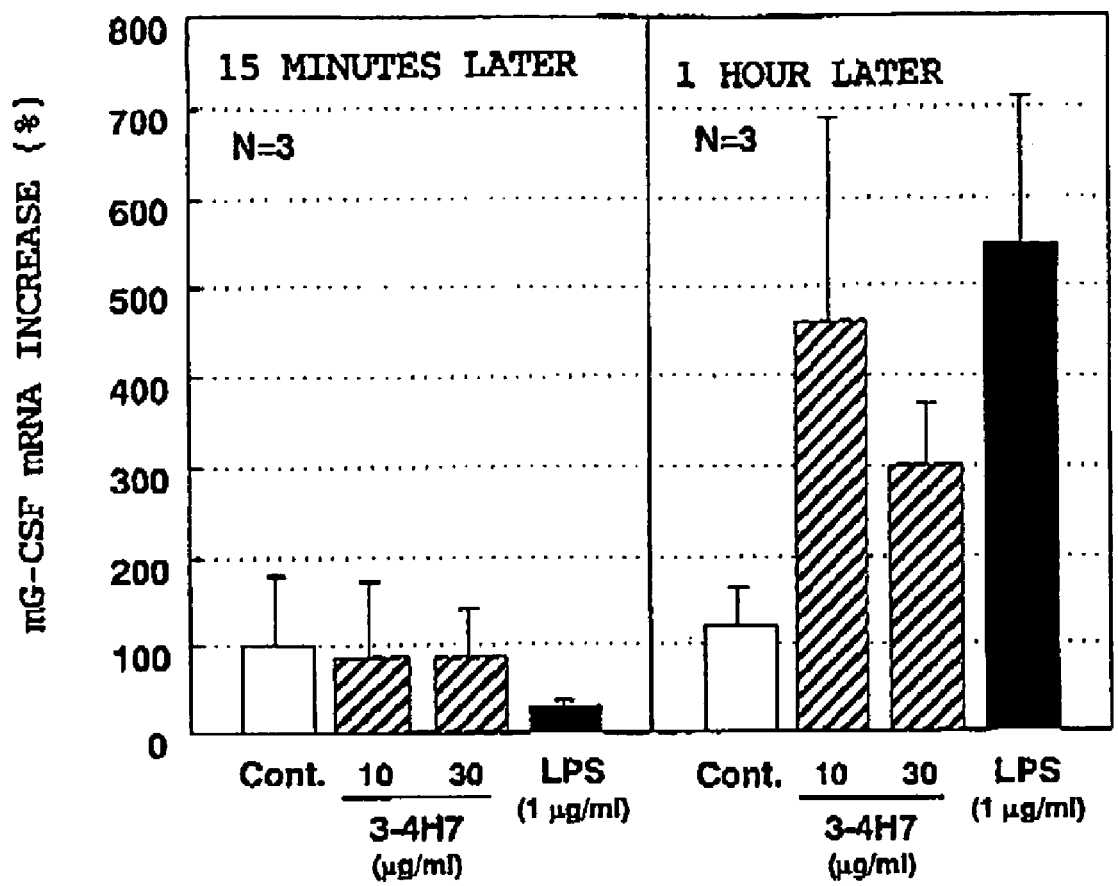
FIG. 16: The mouse G-CSF mRNA induction of the 3-4H7 antibody in macrophage cells. Mouse adherent peripheral monocytes are cultured in a medium containing a macrophage colony-stimulating factor (30 ng/ml) for 4 days so that the cells are differ ntiated into macrophage cells. 3-4H7 antibodies (10, 30 μg/ml) or LPS (1 μg/ml) are added to the macrophage cells. After 15 minutes and 1 hour, the macrophage cells are collected and then the m-RNA is extracted using an RNeasy kit. The amount of the mouse G-CSF RMA is measured by quantitative RT-PCR (PRISM 7700). Moreover, the amount of GAPDH mRNA is measured as an internal standard so as to correct the amount of RNA.

As a result, the 3-4H7 antibody (10 μg/ml) increased the amount of G-CSF mRNA in the macrophage cells by approximately 4.6-fold (FIG. 16). The macrophage cells were simultaneously stimulated with 1 μg/ml LPS for 1 hour, and the amount of G-CSF mRNA in the cells increased by approximately 5.4-fold (FIG. 16).

(4) Preparation of the Total RNA

Using an RNeasy Mini Kit (QIAGEN), the total RNA was extracted from the collected cells. This operation was carried out at room temperature. The extracted total RNA (200 μl) was incubated at 65° C. for 10 minutes, followed by cooling on ice.

(5) Determination of the Mouse G-CSF mRNA Amount

The above prepared mRNA (10 μl) and Taq Man EZ RT-PCR CORE REAGENTS (Perkin Elmer) were mixed on a 96-well reaction Plate (Perkin Elmer), and using ABI Prism 7700 (Applied Biosystems), the amount of the mouse G-CSF mRNA was quantitated (number of cycles: 40). Using GAPDH as an internal standard, the amount of each mRNA was corrected. The used primers are as follows:

```
mG-CSF forward:
CAGCAGACACAGTGCCTAAGC,              (SEQ ID NO: 13)

mG-CSF reverse:
AGTTGGCAACATCCAGCTGAA,              (SEQ ID NO: 14)

mGAPDH forward:
TGCACCACCAACTGCTTAG, and            (SEQ ID NO: 15)

mGAPDH reverse:
GGATGCAGGGATGATGTTC.                (SEQ ID NO: 16)
```

As a probe, SYBER GREEN® was used for mG-CSF, and Vic-CAGAAGACTGTGGATGGCCCCTC-Tamura (SEQ ID NO: 17) was used for mGAPDH.

Figure 17:
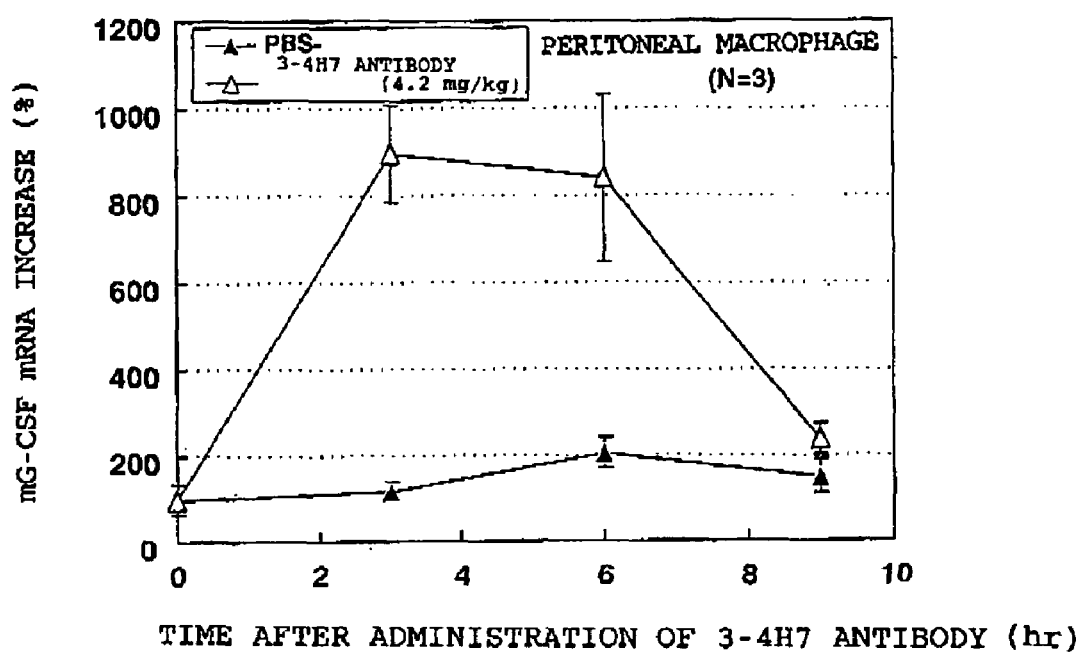
FIG. 17: The mouse G-CSF mRNA induction of the peritoneal macrophage cells by the administration of the 3-4H7 antibody. The 3-4H7 antibody (4.2 mg/kg) is intraperitoneally administered, and after 3, 6 and 9 hours, peritoneal macrophage cells are collected and followed by the extraction of RNA using an RNeasy kit. The amount of the mouse G-CSF mRNA is measured by quantitative RT-PCR (PRISM 7700). Moreover, the amount of GAPDH mRNA is measured as an internal standard so as to correct the amount of RNA.

As a result, at 3 hours after the administration of the 3-4H7 antibody, the amount of G-CSF mRNA in the peritoneal macrophage cells increased by approximately 9-fold of untreated cells (FIG. 17).

(6) Action of 3-4H7 Antibody on Cyclophosphamide-induced Myelosuppressive Mouse

Twenty-four BALB/c mice (male, 9-week old) were intraperitoneally administered with cyclophosphamide (25 mg/ml) at a ratio of 10 ml/kg (250 mg/kg). From 3 days after the administration of cyclophosphamide, the mice were intraperitoneally administered with PBS (a solvent of 3-4H7), a 3-4H7 antibody solution (0.42 mg/ml) and rhG-CSF (1 μg/ml)-at a ratio of 10 ml/kg once a day for 3 days. Moreover, the mice were subcutaneously administered with 10 ml/kg rhG-CSF (1 μg/ml) once a day. Seven days later, the blood (about 40 μl) was collected from the ocular vein of each mouse, using a heparin blood collecting tube, and the number of blood cells was counted with Sysmex F-800 (Sysmex). Moreover, a blood smear was prepared from the same blood, and it was subjected to May-Grünwald Giemsa stain. After staining, 5 classes of 200 leukocytes were counted with a microscope. For detection of significant difference, the implementation of variance analysis was confirmed by 1-way ANOVA, and then LSD test was carried out.

Figure 18:
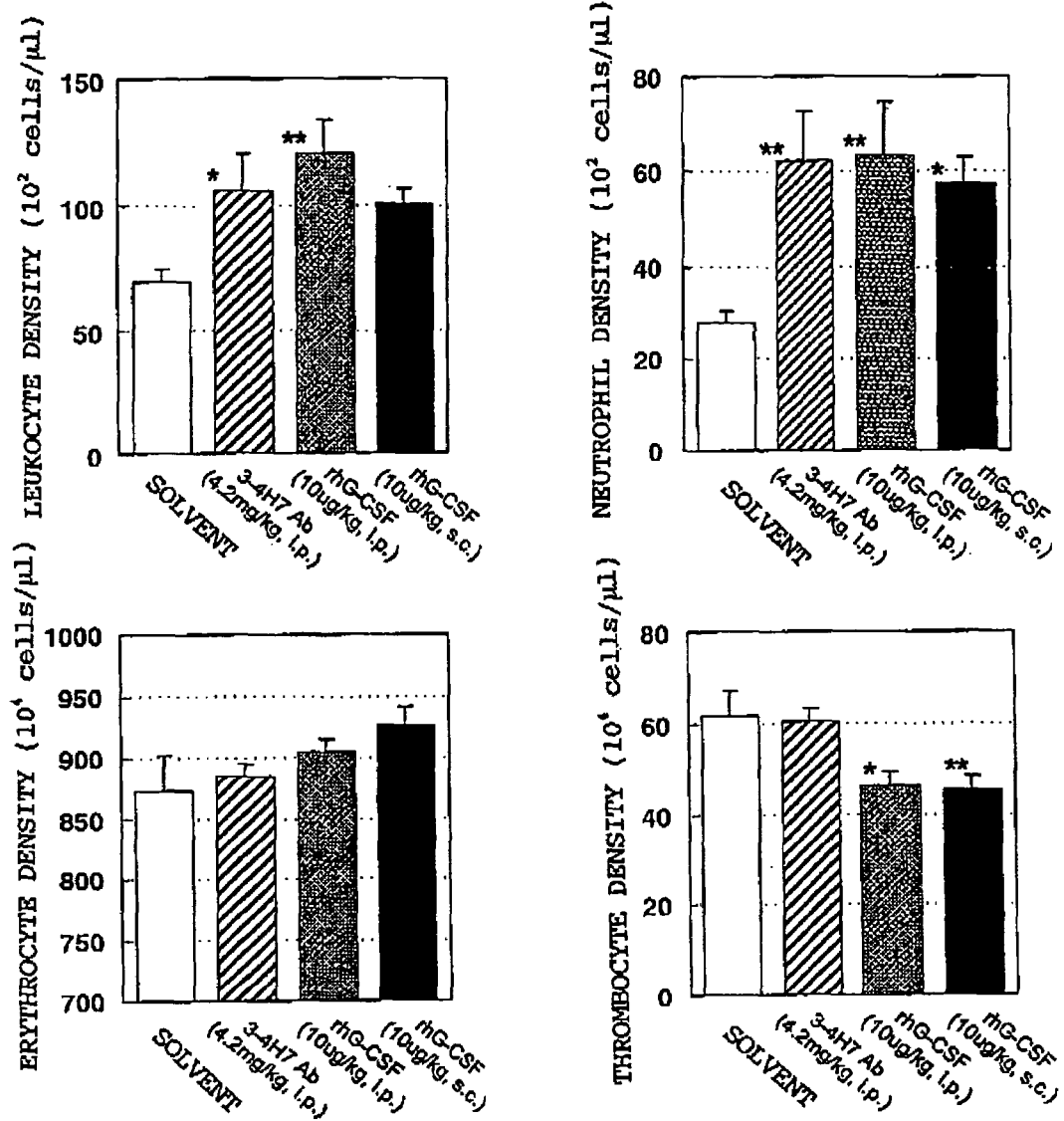
FIG. 18: The effect of the 3-4H7 antibody on cyclophosphamide induced myelosuppressed mice. Cyclophosphamide (250 mg/kg) is intraperitoneally administered to the mice. On the third day after the initiation of the administration of cyclophosphamide, a solvent, the 3-4H7 antibody (4.2 mg/kg) is intraperitoneally administered for 3 days. As a positive control, rhG-CSF (10 μg/kg) is subcutaneously administered (N=6). Seven days after the initiation of the administration of cyclophosphamide, the blood is collected from the orbital venous plexus of the mice, and then the number of each of peripheral leukocytes, erythrocytes and thrombocytes is counted using Sysmex F-800. The smear of the same blood sample is subjected to stain with May-Grünwald-Giemsa solution to count the percentage of neutrophils. Statistical analysis is performed using the one way analysis of variance (one way ANOVA), LSD test is carried out.

As a result, the number of leukocytes and neutrophils significantly increased on the $7^{th}$ day after the administration of cyclophosphamide (FIG. 18). When human G-CSF (10 mg/kg) as a positive control was intraperitoneally administered to the mice for 3 days in the same manner as described above, the number of leukocytes and neutrophils significantly increased on the $7^{th}$ day after the administration, and the increased amount was almost equivalent to the amount increased by the administration of the 3-4H7 antibody (FIG. 18).

INDUSTRIAL APPLICABILITY

The inventive gene protein encoded by the gene (including a fragment of the above gene and a fragment of the above protein), antibody (including a fragment thereof), receptor, and substance (including a low molecular substance) are novel, and these are useful as pharmaceuticals.

Moreover, the inventive gene, protein encoded by the gene (including a fragment of the above gene and a fragment of the above protein), antibody (including a fragment thereof), receptor are also useful as analytic reagents, when a substance capable of inducing and secreting a G-CSF (e.g. a monoclonal antibody, a protein, other low molecular substances, etc.) or the like is screened. Furthermore, since the G-CSF enhances the formation of erythroblasts by erythropoietin or the formation of blast cell colonies by interleukin-3, or promotes (reinforces and increases) blood cells such as leukocytes, erythrocytes or thrombocytes, the above substances Inducing the G-CSF can be used as agents promoting the generation of the G-CSF or agents controlling the biological activity regarding the factor. Specifically, it is expected that the above substances can be used for treatment, diagnosis and others of neutropenia, aplastic anemia and/or cytopenia regarding the reduction of the number of leukocytes, erythrocytes, thrombocytes or the others, while preventing the side effect caused by the direct administration of the G-CSF as an agent.

In addition, the gene fragment of the present invention is useful also as a probe for screening of homologue genes derived from other organisms.

The invention claimed is:

1. An isolated gene encoding a protein having the amino acid sequence shown in SEQ ID NO: 2.

2. An isolated gene having the nucleotide sequence shown in SEQ ID NO: 1.

3. An isolated gene encoding
   (a) a protein having the amino sequence shown in SEQ ID NO: 4; or
   (b) a protein having at least 95% identity with the amino acid sequence shown in SEQ ID NO: 4 through the conservative substitution of one or more acids and also binding to an antibody or an antibody fragment that is produced by the hybridoma cell line deposit as FERM BP-6103.

4. An isolated gene having
   (a) the nucleotide sequence shown in SEQ ID NO: 3;
   (b) a nucleotide sequence encoding a protein having at least 95% identity with the amino acid sequence shown in SEQ ID NO: 4 through the conservative substitution of one or more amino acids and also binding to an antibody or an antibody fragment that is produced by the hybridoma cell line deposited as FERM BP-6103; or
   (c) a nucleotide sequence hybridizing with DNA hiving the nucleotide sequence shown in SEQ ID NO: 3 under stringent conditions of 6×SSC, 5× Denhardt's solution, 0.5% SDS, 25-68° C. or 0-50% formamide, 6×SSC, 0.5% SDS, 25-68° C. and which encodes a protein that can bind to an antibody or antibody fragment that is produced by the hybridoma cell line deposited as FERM BP-6103.

5. The isolated gene according to any one of claims 1 to 4, which is a mouse gene or a human gene.

6. An isolated gene comprising any one of the following nucleotide sequences:
   (a) a nucleotide sequence consisting of nucleotides 519 to 736, nucleotides 666 to 689, nucleotides 381 to 403, or nucleotides 709 to 727 with respect to the nucleotide sequence shown in SEQ ID NO: 1; or
   (b) a nucleotide sequence having at least 95% identity with the nucleotide sequence of (a) above, and also encoding a protein that binds to an antibody or an antibody fragment that is produced by the hybridoma cell line deposited as FERM BP-6103.

7. A purified protein having the amino acid sequence shown in SEQ ID NO: 2.

8. Any of the following purified proteins:
   (a) a protein having the amino acid sequence shown in SEQ ID NO: 4;
   (b) a protein having at least 95% identity with the amino acid sequence shown in SEQ ID NO: 4 through the conservative substitution of one or more amino acids and also binding to an antibody or an antibody fragment that is produced by the hybridoma cell line deposited as FERM BP-6103; or
   (c) a protein encoded by DNA which hybridizes with DNA having the nucleotide sequence shown in SEQ ID NO: 3 under stringent conditions of 6×SSC, 5× Denhardt's solution, 0.05% SDS, 2.5-68° C. or 0-50% formamide, 6×SSC, 0.5% SDS, 25-68° C. and which encodes a protein unit can bind to an antibody or antibody fragment that is produced by the hybridoma cell line deposited as FERM BP-6103.

9. The purified protein according to claim 7 or 8, which is mouse or human protein.

10. A purified protein having any one of the following amino acid sequences:

(a) an amino acid sequence consisting of amino acids 1 to 91, amino acids 50 to 146, ammo acids 1 to 78, amino acids 200 to 241, amino acids 172 to 241, amino acids 103 to 150, or (b) an amino acid sequence having at least 95% identity with the amino acid sequence of (a) above, and also binding to an antibody or an antibody fragment that is produced by the hybridoma cell line deposited as FERM BP-6103.

11. A recombinant vector comprising the gene according to any one or claims 1 to 4.

12. A transformed cell comprising a recombinant vector that contains the gene according to any one of claims 1 to 4.

13. An isolated receptor for a substance that can induce the production of a granulocyte colony-stimulating factor which comprises a monoclonal antibody or an antibody fragment produced front hybridoma cells deposited under Accession No. FERM BP-6103, wherein said receptor comprising the protein according to any one of claims 7 or 8, and is present in a cell which can produce granulocyte colony-stimulating factor.

14. A method of screening for a substance that can bind to the protein of claim 7 or 8, which comprises i) providing a potential substance;

ii) exposing the potential substance to said protein, and iii) testing for specific bindine.

15. A method of screening for a substance that can bind to the receptor according to claim 13, which comprises i) providing a potential substance;

ii) exposing the potential substance to said receptor, and iii) testing for specific binding.

* * * * *